US009296698B2

(12) United States Patent
Cheng et al.

(10) Patent No.: US 9,296,698 B2
(45) Date of Patent: Mar. 29, 2016

(54) AMINO HETEROARYL COMPOUNDS AS BETA-SECRETASE MODULATORS AND METHODS OF USE

(75) Inventors: Yuan Cheng, Newbury Park, CA (US); Timothy Powers, Malibu, CA (US); Kate Ashton, Westlake Village, CA (US); James Brown, Moorpark, CA (US); Scott Harried, Woodland Hills, CA (US); Stephen A. Hitchcock, Juniper, FL (US); Ted Judd, Simi Valley, CA (US); Patricia Lopez, West Hills, CA (US); Thomas Nixey, Newbury Park, CA (US); Nick A. Paras, San Francisco, CA (US); Steve F. Poon, Woodland Hills, CA (US); David J. St. Jean, Jr., Camarillo, CA (US); Qiufen Xue, Newbury Park, CA (US); Wenge Zhong, Thousand Oaks, CA (US)

(73) Assignee: Amgen Inc., Thousand Oaks, CA (US)

(*) Notice: Subject to any disclaimer, the term of this patent is extended or adjusted under 35 U.S.C. 154(b) by 450 days.

(21) Appl. No.: 13/511,359

(22) PCT Filed: Nov. 19, 2010

(86) PCT No.: PCT/US2010/057428
§ 371 (c)(1),
(2), (4) Date: Sep. 12, 2012

(87) PCT Pub. No.: WO2011/063233
PCT Pub. Date: May 26, 2011

(65) Prior Publication Data
US 2012/0329830 A1 Dec. 27, 2012

Related U.S. Application Data

(60) Provisional application No. 61/263,720, filed on Nov. 23, 2009.

(51) Int. Cl.
| | |
|---|---|
| *C07D 215/38* | (2006.01) |
| *C07D 401/04* | (2006.01) |
| *C07D 401/10* | (2006.01) |
| *C07D 401/12* | (2006.01) |
| *C07D 405/12* | (2006.01) |
| *C07D 417/04* | (2006.01) |

(52) U.S. Cl.
CPC ............ *C07D 215/38* (2013.01); *C07D 401/04* (2013.01); *C07D 401/10* (2013.01); *C07D 401/12* (2013.01); *C07D 405/12* (2013.01); *C07D 417/04* (2013.01)

(58) Field of Classification Search
None
See application file for complete search history.

(56) References Cited

U.S. PATENT DOCUMENTS

| 5,441,870 A | 8/1995 | Seubert et al. |
| 5,712,130 A | 1/1998 | Hajko et al. |
| 5,942,400 A | 8/1999 | Anderson et al. |
| 2010/0041698 A1 | 2/2010 | Amberg et al. |

FOREIGN PATENT DOCUMENTS

| WO | 2005009969 A1 | 2/2005 |
| WO | 2006/017836 A2 | 2/2006 |
| WO | 2006/017844 A1 | 2/2006 |
| WO | 2006/024932 A1 | 3/2006 |
| WO | 2007022946 A1 | 3/2007 |
| WO | 2007/050612 A1 | 5/2007 |
| WO | 2007/092839 A2 | 8/2007 |

(Continued)

OTHER PUBLICATIONS

Joachim et al., *Alz. Dis. Assoc. Dis.*, 6:7-34 (1992).
Selkoe, *Neuron*, 6:487 (1991).
Seubert et al., *Nature*, 359:325-327 (1992).
Citron, *Trends in Pharmacological Sciences*, 25(2):92-97 (2004).

(Continued)

*Primary Examiner* — Sreeni Padmanabhan
*Assistant Examiner* — Jody Karol
(74) *Attorney, Agent, or Firm* — G. Prabhakar Reddy; Markus Bergauer

(57) ABSTRACT

The present invention comprises a new class of compounds useful for the modulation of Beta-secretase enzyme activity and for the treatment of Beta-secretase mediated diseases, including Alzheimer's disease (AD) and related conditions. In one embodiment, the compounds have a general Formula I wherein ring A, $B^1$, $B^2$, $B^3$, L, $R^1$, $R^4$, $R^5$ and m of Formula I are defined herein. The invention also includes use of these compounds in pharmaceutical compositions for treatment, prophylactic or therapeutic, of disorders and conditions related to the activity of beta-secretase protein. Such disorders include, for example, Alzheimer's Disease (AD), cognitive deficits, cognitive impairment, schizophrenia and other central nervous system conditions related to and/or caused by the formation and/or deposition of plaque on the brain. The invention also comprises further embodiments of Formula I, intermediates and processes useful for the preparation of compounds of Formula I.

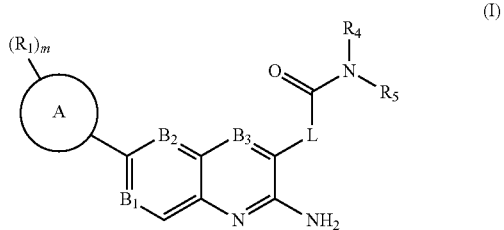

14 Claims, No Drawings

(56) References Cited

FOREIGN PATENT DOCUMENTS

| | | |
|---|---|---|
| WO | 2007/092846 A2 | 8/2007 |
| WO | 2007092846 A2 | 8/2007 |
| WO | 2007092854 A2 | 8/2007 |
| WO | 2009/007300 A2 | 1/2009 |
| WO | 2009097278 A1 | 8/2009 |
| WO | 2009097401 A1 | 8/2009 |
| WO | WO 2009097401 A1 * | 8/2009 |

OTHER PUBLICATIONS

*Nature Medicine* (Jun. 22, 2008) online doi 10:1038 nm 1782, Town, T.
Sinha et al., *Nature*, 402:537-554 (1999) (p. 510).
Sabbagh, M. et al., *Alz. Dis. Rev.* 3:1-19 (1997).
Cole, S.L., Vasser, R., *Molecular Degeneration* 2:22, 2007.
Luo et al., *Nature Neuroscience*, 4:231-232 (2001).
*Bulletin of Experimental Biology and Medicine* 129 (6): 544-546), Levermontova et al.

* cited by examiner

AMINO HETEROARYL COMPOUNDS AS BETA-SECRETASE MODULATORS AND METHODS OF USE

RELATED APPLICATIONS

This application is a national stage application under 35 U.S.C. §371 of International Application No. PCT/US2010/057428, having an international filing date of Nov. 19, 2010, which claims the benefit of, and priority to, U.S. Provisional Patent Application No. 61/263,720, filed on Nov. 23, 2009, which is hereby incorporated herein by reference in its entirety.

FIELD OF THE INVENTION

The invention relates generally to new compounds, pharmaceutical compositions and methods of use thereof, to treat Beta-Secretase mediated diseases and conditions, including, without limitation, Alzheimer's disease, plaque formation in the brain as well as in the peripheral central nervous system and disorders related thereto.

BACKGROUND OF THE INVENTION

Alzheimer's disease (AD) affects greater than 12 million people worldwide. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenisis of AD and can precede cognitive symptoms by years or even decades. Selkoe, *Neuron*, 6:487 (1991). Release of A-beta from neuronal cells grown in culture and the presence of A-beta in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acid residues. A-beta 40 and 42 (42 amino acids long) are thought to be the major component of these plaque deposits in the brains of Alzheimer's Disease patients. Citron, *Trends in Pharmacological Sciences*, 25(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the two-molecule, soluble form of the peptide is a causative agent in the development of Alzheimer's and that the two-molecule form is the smallest synaptotoxic species of soluble amyloid beta oligomer. Shnakar, G. M., *Nature Medicine* (Jun. 22, 2008) online doi 10:1038 nm 1782.

Several aspartyl proteases are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP was also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compares with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities.

Recently Dimebon has attracted renewed interest after being shown to have positive effects on persons suffering from Alzheimer's disease. Animal studies showing potential beneficial effects on Alzheimer's disease models were shown in Russian research in 2000 (Lermontova N N, Lukoyanov N V, Serkova T P, Lukoyanova E A, Bachurin S O (June 2000). "Dimebon improves learning in animals with experimental Alzheimer's disease". *Bulletin of Experimental Biology and Medicine* 129 (6): 544-546). Preliminary results from human trials have also been promising. In an initial six-month phase II trial, results have shown that at 12 months there was significant improvement over placebo. Dimebon appears to operate through multiple mechanisms of action, both blocking the action of neurotoxic beta amyloid proteins and inhibiting L-type calcium channels modulating the action of AMPA and NMDA glutamate receptors. To this end, inhibition of cleavage or fragmentation of beta amyloid protein via the beta secretase pathway may provide a therapeutic method for treating AD and other beta amyloid or plaque related disorders.

Several approaches have been taken to potentially treat AD and plaque-related disorders. One approach has been to attempt to reduce the formation of plaque on the brain, by inhibiting or reducing the activity of BACE. For example, each of the following PCT publications: WO 03/045913, WO 04/043916, WO 03/002122, WO 03/006021, WO 03/002518, WO 04/024081, WO 03/040096, WO 04/050619, WO 04/080376, WO 04/099376, WO 05/004802, WO 04/080459, WO 04/062625, WO 04/042910, WO 05/004803, WO 05/005374, WO 03/106405, WO 03/062209, WO 03/030886, WO 02/002505, WO 01/070671, WO 03/057721, WO 03/006013, WO 03/037325, WO 04/094384, WO 04/094413, WO 03/006423, WO 03/050073, WO 03/029169 and WO 04/000821, describe inhibitors of BACE, potentially useful for treating AD and other beta-secretase mediated disorders. Despite these efforts, there is always a need to find new compounds which may effectively treat such plaque-related conditions and disorders, such as AD.

BRIEF DESCRIPTION OF THE INVENTION

The present invention provides a new class of compounds useful for the modulation of beta secretase activity. To that end, the compounds of the invention are useful for the regulation or reduction of the formation of A-beta peptide and, consequently, the regulation and/or reduction of beta amyloid plaque formation on the brain. Accordingly, the compounds are useful for the treatment of Alzheimer's disease and other beta secretase and/or plaque mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, solvates, pharmaceutically acceptable salts, derivatives or prodrugs thereof, are generally defined by Formula I

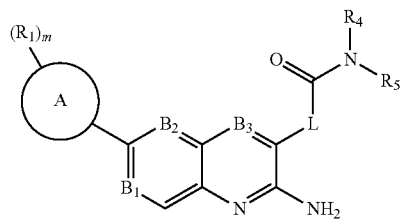

wherein ring A, $B^1$, $B^2$, L, $R^1$, $R^4$, $R^5$ and m of Formula I are described below. The invention also provides compounds of sub-formulas of Formula I, as well as procedures for making compounds of Formula I and intermediates useful in such procedures.

The invention further provides pharmaceutical compositions, which comprise one or more compounds of the invention, methods for the treatment of beta secretase mediated diseases, such as AD, using the compounds and compositions of the invention. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts, derivatives or prodrugs thereof, are generally defined by

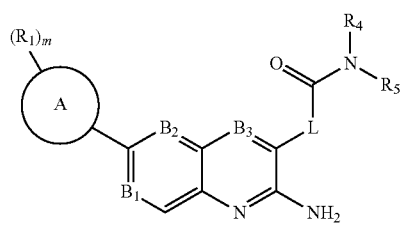

wherein
A is a cyclopropyl or a 5- or 6-membered aryl or heteraryl ring;
each of $B^1$, $B^2$ and $B^3$, independently, is N, —CF, —CCH$_3$ or CH;
L is —CR$^2$R$^2$—(CR$^3$R$^3$)$_o$— wherein each $R^2$ independently is H or halo; and
each $R^3$ independently is H, $C_{1-6}$alkyl, $C_{3-6}$cycloalkyl, —OH, —OC$_{1-4}$alkyl,
halo, haloalkyl, CN, —NH$_2$ or —NHC$_{1-6}$alkyl and o is 1 or 2;
each $R^1$ independently, is F, Cl, Br, CF$_3$, OCF$_3$, $C_{1-6}$-alkyl, CN, OH, —OC$_{1-6}$-alkyl, $C_{1-6}$-alkenyl, $C_{1-6}$-alkynyl, —S(O)$_n$C$_{1-6}$-alkyl, —NH$_2$, CN, —NHC$_{1-6}$-alkyl, —C(O)C$_{1-6}$-alkyl, —C(O)-aryl, —C(O)-heteroaryl, —C(O)-heterocyclyl, —C(O)—C$_{3-8}$-cycloalkyl or —C(O)NR$^a$R$^b$ wherein R$^a$ is H or C$_{1-6}$alkyl and R$^b$ is R$^6$;

alternatively, $R^a$ and $R^b$ taken together with the nitrogen atom to which they are attached form a 4-7 membered monocyclic or 6-10 membered bicyclic heterocycle, wherein the $C_{1-6}$-alkyl, and $C_{1-6}$-alkyl portion of the —$OC_{1-6}$-alkyl, $C_{3-8}$-cycloalkyl of the —C(O)—$C_{3-8}$-cycloalkyl, and monocyclic and bicyclic heterocycle are optionally substituted with 1-3 substituents of $R^6$;

$R^4$ is H or $CH_3$;

$R^5$ is H, $C_{1-6}$-alkyl, $C_{2-6}$alkenyl, $C_{2-6}$-alkynyl, $C_{3-8}$-cycloalkyl, $C_{4-8}$-cycloalkenyl or a fully saturated or partially or fully unsaturated 3-, 4-, 5- or 6-membered monocyclic or a 7-11 membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^6$;

alternatively, $R^4$ and $R^5$ taken together with the nitrogen atom to which they are attached form a 4-7 membered monocyclic heterocycle, optionally substituted with 1-3 substituents of $R^6$;

each $R^6$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

m is 0, 1, 2, 3, 4 or 5; and n is 0, 1 or 2.

In another embodiment, the compounds of Formula I includes compounds wherein ring A is an optionally substituted 5- or 6-membered aryl or heteroaryl or a 3- to 8-membered cycloalkyl or heterocyclyl, in conjunction with any of the above or below embodiments.

In another embodiment, the compounds of Formula I includes compounds wherein ring A is an optionally substituted 5- or 6-membered aryl or heteroaryl, in conjunction with any of the above or below embodiments.

In another embodiment, the compounds of Formula I includes compounds wherein ring A is an optionally substituted 5-membered heteroaryl, in conjunction with any of the above or below embodiments.

In another embodiment, the compounds of Formula I includes compounds wherein ring A is an optionally substituted 6-membered heteroaryl, in conjunction with any of the above or below embodiments.

In another embodiment, the compounds of Formula I includes compounds wherein ring A is an optionally substituted 6-membered aryl, in conjunction with any of the above or below embodiments.

In another embodiment, the compounds of Formula I includes compounds wherein ring A is an optionally substituted phenyl, pyridine, pyrimidine, triazine, pyrazine, pyridazine, imidazole, pyrazole, thiazole, oxazole, isoxazole, isothiazole, pyrrole, furan, thiophene, cyclopropane, cyclobutane, cyclopentane, cyclohexane, morpholine, piperidine or piperazine ring, in conjunction with any of the above or below embodiments.

In another embodiment, the compounds of Formula I includes compounds wherein ring A is an optionally substituted phenyl, pyridine, pyrimidine, triazine, cyclopropane or thiophene, in conjunction with any of the above or below embodiments.

In another embodiment, the compounds of Formula I includes compounds wherein ring A is a phenyl, pyridine, pyrimidine, triazine or thiophene, in conjunction with any of the above or below embodiments.

In another embodiment, the compounds of Formula I includes compounds wherein ring A is a phenyl, 2-pyridyl, 3-pyridyl or 4-pyridyl ring, in conjunction with any of the above or below embodiments.

In another embodiment, the compounds of Formula I includes compounds wherein $B^1$ is $CR^2$, in conjunction with any of the above or below embodiments.

In another embodiment, the compounds of Formula I includes compounds wherein $B^1$ is N, in conjunction with any of the above or below embodiments.

In another embodiment, the compounds of Formula I includes compounds wherein $B^2$ is $CR^2$, in conjunction with any of the above or below embodiments.

In another embodiment, the compounds of Formula I includes compounds wherein $B^2$ is N, in conjunction with any of the above or below embodiments.

In another embodiment, the compounds of Formula I includes compounds wherein $B^2$ is CH, in conjunction with any of the above or below embodiments.

In another embodiment, the compounds of Formula I includes compounds wherein $B^1$ is CH, in conjunction with any of the above or below embodiments.

In another embodiment, the compounds of Formula I includes compounds wherein $B^1$ is $CR^2$ and $B^2$ is $CR^2$, in conjunction with any of the above or below embodiments.

In another embodiment, the compounds of Formula I includes compounds wherein $B^1$ is $CR^2$ and $B^2$ is CH, in conjunction with any of the above or below embodiments.

In another embodiment, the compounds of Formula I includes compounds wherein $B^1$ is N and $B^2$ is $CR^2$, in conjunction with any of the above or below embodiments.

In another embodiment, the compounds of Formula I includes compounds wherein $B^1$ is N and each of $B^2$ and $B^3$, independently, is $CR^2$, in conjunction with any of the above or below embodiments.

In another embodiment, the compounds of Formula I includes compounds wherein $B^3$ is N and each of $B^1$ and $B^2$, independently, is $CR^2$, in conjunction with any of the above or below embodiments.

In another embodiment, the compounds of Formula I includes compounds wherein $B^1$ is $CR^2$ and $B^2$ is N, in conjunction with any of the above or below embodiments.

In another embodiment, the compounds of Formula I includes compounds wherein one of $B^1$ and $B^3$ is N and the other of $B^1$ and $B^3$ is $CR^2$, in conjunction with any of the above or below embodiments.

In another embodiment, the compounds of Formula I includes compounds wherein $B^1$ is N and $B^2$ is N, in conjunction with any of the above or below embodiments.

In another embodiment, the compounds of Formula I includes compounds wherein L is —$CR^2R^2$—$(CR^3R^3)_o$— wherein o is 1 or 2, and each $R^3$ independently is H, $C_{1-6}$alkyl, $C_{3-6}$cycloalkyl, —OH, —$OC_{1-4}$alkyl, halo, haloalkyl, CN, —NH₂ or —NHC₁₋₆alkyl, in conjunction with any of the above or below embodiments.

In another embodiment, the compounds of Formula I includes compounds wherein L is —CR³R³—CR³R³—CH₂— wherein each R³ independently is H, C₁₋₆alkyl, C₃₋₆cycloalkyl, —OH, —OC₁₋₄alkyl, halo, haloalkyl, CN, —NH₂ or —NHC₁₋₆alkyl, in conjunction with any of the above or below embodiments.

In another embodiment, the compounds of Formula I includes compounds wherein L is —CHR³—CHR³— wherein each R³ independently is H, C₁₋₆alkyl, C₃₋₆cycloalkyl, —OH, —OC₁₋₄alkyl, halo, haloalkyl, CN, —NH₂ or —NHC₁₋₆alkyl, in conjunction with any of the above or below embodiments.

In another embodiment, the compounds of Formula I includes compounds wherein L is —CH₂—CHR³— wherein R³ is H, C₁₋₆alkyl, C₃₋₆cycloalkyl, —OH, —OC₁₋₄alkyl, halo, haloalkyl, CN, —NH₂ or —NHC₁₋₆alkyl, in conjunction with any of the above or below embodiments.

In another embodiment, the compounds of Formula I includes compounds wherein L is —CH₂—CHR³— wherein R³ is C₁₋₆alkyl, C₃₋₆cycloalkyl, —OH, —OC₁₋₄alkyl, halo, haloalkyl, CN, —NH₂ or —NHC₁₋₆alkyl, in conjunction with any of the above or below embodiments.

In another embodiment, the compounds of Formula I includes compounds wherein L is —CH₂—CHR³— wherein R³ is methyl, ethyl, propyl, cyclopropyl, cyclobutyl, cyclopentyl, cyclohexyl, —OH, —OCH₃, F, Cl, Br, —OCF₃, CN, —NH₂ or —NHC₁₋₃alkyl, in conjunction with any of the above or below embodiments.

In another embodiment, the compounds of Formula I includes compounds wherein L is —CH₂—CHR³— wherein R³ is methyl, ethyl, propyl or F, in conjunction with any of the above or below embodiments.

In another embodiment, the compounds of Formula I includes compounds wherein L is —CH₂—CHR³— wherein R³ is methyl, in conjunction with any of the above or below embodiments.

In another embodiment, the compounds of Formula I includes compounds wherein L is —(CR³R³)ₒ— wherein o is 2 or 3 and each R³ independently is H, methyl, ethyl, propyl, cyclopropyl, cyclobutyl, cyclopentyl, cyclohexyl, —OH, —OCH₃, F, Cl, Br, —OCF₃, CN, —NH₂ or —NHC₁₋₃alkyl, in conjunction with any of the above or below embodiments.

In one embodiment of the invention, the compounds, including stereoisomers, tautomers, solvates, pharmaceutically acceptable salts, derivatives or prodrugs thereof, are generally defined by Formula I-A each R¹, independently, is H, F, Cl, Br, CF₃, OCF₃, C₁₋₆-alkyl, CN, OH, —OC₁₋₆-alkyl, C₁₋₆-alkenyl, C₁₋₆-alkynyl, —S(O)ₙC₁₋₆-alkyl, —NH₂, CN, —NHC₁₋₆-alkyl, —C(O)C₁₋₆-alkyl, —C(O)-aryl, —C(O)-heteroaryl, —C(O)-heterocyclyl, —C(O)—C₃₋₈-cycloalkyl or —C(O)NRᵃRᵇ wherein Rᵃ is H or C₁₋₆alkyl and Rᵇ is R⁶, wherein the C₁₋₆-alkyl, and C₁₋₆-alkyl portion of the —OC₁₋₆-alkyl, C₃₋₈-cycloalkyl of the —C(O)—C₃₋₈-cycloalkyl are optionally substituted with 1-3 substituents of R⁶;

each R², independently, is H or F;

R³ is H, C₁₋₆alkyl, C₃₋₆cycloalkyl, —OH, —OC₁₋₄alkyl, halo, haloalkyl, CN, —NH₂ or —NHC₁₋₆alkyl;

R⁴ is H or methyl;

R⁵ is C₁₋₆-alkyl, C₂₋₆alkenyl, C₂₋₆-alkynyl, C₃₋₈-cycloalkyl, C₄₋₈-cycloalkenyl or a fully saturated or partially or fully unsaturated 3-, 4-, 5- or 6-membered monocyclic or a 7-11 membered bicyclic ring formed of carbon atoms, said ring optionally including 1-4 heteroatoms selected from O, N, or S, wherein the C₁₋₆-alkyl, C₂₋₆-alkenyl, C₂₋₆-alkynyl, C₃₋₈-cycloalkyl, C₄₋₈-cycloalkenyl and ring are optionally substituted, independently, with 1-5 substituents of R⁶;

alternatively, R⁴ and R⁵ taken together with the nitrogen atom to which they are attached form a 4-7 membered monocyclic heterocycle, optionally substituted with 1-3 substituents of R⁶; and each R⁶, independently, is H, halo, haloalkyl, CN, OH, NO₂, NH₂, acetyl, oxo, C₁₋₁₀-alkyl, C₂₋₁₀-alkenyl, C₂₋₁₀-alkynyl, C₃₋₁₀-cycloalkyl, C₄₋₁₀-cycloalkenyl, C₁₋₁₀-alkylamino-, C₁₋₁₀-dialkylamino-, C₁₋₁₀-alkoxyl, C₁₋₁₀-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C₁₋₁₀-alkyl, C₂₋₁₀-alkenyl, C₂₋₁₀-alkynyl, C₃₋₁₀-cycloalkyl, C₄₋₁₀-cycloalkenyl, C₁₋₁₀-alkylamino-, C₁₋₁₀-dialkylamino-, C₁₋₁₀-alkoxyl, C₁₋₁₀-thioalkoxyl and ring of said ring system is optionally substituted independently with 1-5 substituents of halo, haloalkyl, haloalkoxyl, CN, NO₂, NH₂, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C₁₋₁₀-alkylamino-, C₁₋₁₀-dialkylamino-, C₁₋₁₀-thioalkoxyl, benzyl or phenyl.

In one embodiment of the invention, the compounds, including stereoisomers, tautomers, solvates, pharmaceutically acceptable salts thereof, are generally defined by Formula I-B

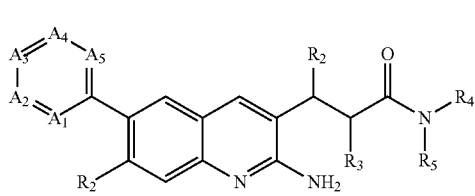

I-A

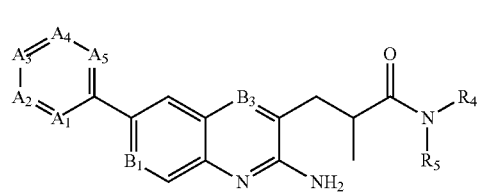

I-B wherein
A¹ is CR¹ or N;
A² is CR¹ or N;
A³ is CR¹ or N;
A⁴ is CR¹ or N;
A⁵ is CR¹ or N, provided no more than two of A¹, A², A³, A⁴ and A⁵ is N;

wherein
A¹ is CR¹ or N;
A² is CR¹ or N;
A³ is CR¹ or N;
A⁴ is CR¹ or N;
A⁵ is CR¹ or N, provided no more than two of A¹, A², A³, A⁴ and A⁵ is N;

each of $B^1$ and $B^3$, independently, is N, —CF, —CCH$_3$ or CH;

each $R^1$, independently, is H, F, Cl, Br, CF$_3$, OCF$_3$, C$_{1-6}$-alkyl, CN, OH, —OC$_{1-6}$-alkyl, C$_{1-6}$-alkenyl, C$_{1-6}$-alkynyl, —S(O)$_n$C$_{1-6}$-alkyl, —NH$_2$, CN, —NHC$_{1-6}$-alkyl, —C(O)C$_{1-6}$-alkyl, —C(O)-aryl, —C(O)-heteroaryl, —C(O)-heterocyclyl, —C(O)—C$_{3-8}$-cycloalkyl or —C(O)NR$^a$R$^b$ wherein R$^a$ is H or C$_{1-6}$alkyl and R$^b$ is R$^6$, wherein the C$_{1-6}$-alkyl, and C$_{1-6}$-alkyl portion of the —OC$_{1-6}$-alkyl, C$_{3-8}$-cycloalkyl of the —C(O)—C$_{3-8}$-cycloalkyl are optionally substituted with 1-3 substituents of R$^6$;

R$^4$ is H or methyl;

R$^5$ is C$_{1-6}$-alkyl, C$_{2-6}$alkenyl, C$_{2-6}$-alkynyl, C$_{3-8}$-cycloalkyl, C$_{4-8}$-cycloalkenyl or a fully saturated or partially or fully unsaturated 3-, 4-, 5- or 6-membered monocyclic or a 7-11 membered bicyclic ring formed of carbon atoms, said ring optionally including 1-4 heteroatoms selected from O, N, or S, wherein the C$_{1-6}$-alkyl, C$_{2-6}$-alkenyl, C$_{2-6}$-alkynyl, C$_{3-8}$-cycloalkyl, C$_{4-8}$-cycloalkenyl and ring are optionally substituted, independently, with 1-5 substituents of R$^6$;

alternatively, R$^4$ and R$^5$ taken together with the nitrogen atom to which they are attached form a 4-7 membered monocyclic heterocycle, optionally substituted with 1-3 substituents of R$^6$; and each R$^6$, independently, is H, halo, haloalkyl, CN, OH, NO$_2$, NH$_2$, acetyl, oxo, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, haloalkoxyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C$_{1-10}$-alkylamino-, C$_{1-10}$-dialkylamino-, C$_{1-10}$-thioalkoxyl, benzyl or phenyl.

In another embodiment, the compounds of Formula I-A and I-B include compounds wherein A$^1$ is CR$^1$, in conjunction with any of the above or below embodiments.

In another embodiment, the compounds of Formula I-A and I-B include compounds wherein A$^1$ is N, in conjunction with any of the above or below embodiments.

In another embodiment, the compounds of Formula I-A and I-B include compounds wherein A$^2$ is CR$^1$, in conjunction with any of the above or below embodiments.

In another embodiment, the compounds of Formula I-A includes compounds wherein A$^2$ is N, in conjunction with any of the above or below embodiments.

In another embodiment, the compounds of Formula I-A and I-B include compounds wherein A$^3$ is CR$^1$, in conjunction with any of the above or below embodiments.

In another embodiment, the compounds of Formula I-A and I-B include compounds wherein A$^3$ is N, in conjunction with any of the above or below embodiments.

In another embodiment, the compounds of Formula I-A and I-B include compounds wherein A$^4$ is CR$^1$, in conjunction with any of the above or below embodiments.

In another embodiment, the compounds of Formula I-A and I-B include compounds wherein A$^4$ is N, in conjunction with any of the above or below embodiments.

In another embodiment, the compounds of Formula I-A and I-B include compounds wherein A$^5$ is CR$^1$, in conjunction with any of the above or below embodiments.

In another embodiment, the compounds of Formula I-A and I-B include compounds wherein A$^5$ is N, in conjunction with any of the above or below embodiments.

In another embodiment, the compounds of Formula I-A and I-B include compounds wherein one of A$^1$, A$^2$, A$^3$, A$^4$ and A$^5$ is N and the other four of A$^1$, A$^2$, A$^3$, A$^4$ and A$^5$ is CR$^1$ as defined in Formula I, in conjunction with any of the above or below embodiments.

In another embodiment, the compounds of Formula I-A and I-B include compounds wherein one of A$^1$ and A$^2$ is N and the other of A$^1$ and A$^2$ is CR$^1$, A$^3$ is CR$^1$, A$^4$ is CR$^1$ and A$^5$ is CR$^1$, in conjunction with any of the above or below embodiments.

In another embodiment, the compounds of Formula I-A and I-B include compounds wherein each of A$^1$, A$^2$, A$^3$, A$^4$ and A$^5$ is CR$^1$ as defined in Formula I, in conjunction with any of the above or below embodiments.

In another embodiment, the compounds of Formula I and I-B include compounds wherein each of A$^1$, A$^2$, A$^3$, A$^4$ and A$^5$, independently, is CR$^1$ wherein each R$^1$, independently, is H, F, Cl, Br, CF$_3$, OCF$_3$, C$_{1-6}$-alkyl, CN, OH, —OC$_{1-6}$-alkyl, C$_{1-6}$-alkenyl, C$_{1-6}$-alkynyl, —S(O)$_n$C$_{1-6}$-alkyl, —NH$_2$, CN, —NHC$_{1-6}$-alkyl, —C(O)C$_{1-6}$-alkyl, —C(O)-aryl, —C(O)-heteroaryl, —C(O)-heterocyclyl, —C(O)—C$_{3-8}$-cycloalkyl or —C(O)NR$^a$R$^b$ wherein R$^a$ is H or C$_{1-6}$alkyl and R$^b$ is R$^6$, wherein the C$_{1-6}$-alkyl, and C$_{1-6}$-alkyl portion of the —OC$_{1-6}$-alkyl, C$_{3-8}$-cycloalkyl of the —C(O)—C$_{3-8}$-cycloalkyl are optionally substituted with 1-3 substituents of R$^6$, in conjunction with any of the above or below embodiments.

In another embodiment, the compounds of Formula I-A and I-B include compounds wherein each of A$^1$, A$^2$, A$^3$, A$^4$ and A$^5$, independently, is CR$^1$ wherein each R$^1$, independently, is H, F, Cl, Br, CF$_3$, OCF$_3$, C$_{1-6}$-alkyl, CN, OH, OC$_{1-6}$-alkyl, SC$_{1-6}$-alkyl, NHC$_{1-6}$-alkyl or C(O)C$_{1-6}$-alkyl, in conjunction with any of the above or below embodiments.

In another embodiment, the compounds of Formulas I, I-A and I-B include compounds wherein each R$^1$ independently, is F, Cl, Br, CF$_3$, OCF$_3$, C$_{1-6}$-alkyl, CN, OH, —OC$_{1-6}$-alkyl, C$_{1-6}$-alkenyl, C$_{1-6}$-alkynyl, —S(O)$_n$C$_{1-6}$-alkyl, —NH$_2$, CN, —NHC$_{1-6}$-alkyl, —C(O)C$_{1-6}$-alkyl, —C(O)-aryl, —C(O)-heteroaryl, —C(O)-heterocyclyl, —C(O)—C$_{3-8}$-cycloalkyl or —C(O)NR$^a$R$^b$ wherein R$^a$ is H or C$_{1-6}$alkyl and R$^b$ is R$^6$;

alternatively, R$^a$ and R$^b$ taken together with the nitrogen atom to which they are attached form a 4-7 membered monocyclic or 6-10 membered bicyclic heterocycle, wherein the C$_{1-6}$-alkyl, and C$_{1-6}$-alkyl portion of the —OC$_{1-6}$-alkyl, C$_{3-8}$-cycloalkyl of the —C(O)—C$_{3-8}$-cycloalkyl, and monocyclic and bicyclic heterocycle are optionally substituted with 1-3 substituents of R$^6$, in conjunction with any of the above or below embodiments.

In another embodiment, the compounds of Formulas I, I-A and I-B include compounds wherein each R$^1$ independently, F, Cl, Br, CF$_3$, OCF$_3$, C$_{1-6}$-alkyl, CN, OH, —OC$_{1-6}$-alkyl, —S(O)$_n$C$_{1-6}$-alkyl, —NH$_2$, CN, —NHC$_{1-6}$-alkyl, —C(O)C$_{1-6}$-alkyl, —C(O)—C$_{3-8}$-cycloalkyl or —C(O)NR$^a$R$^b$ wherein R$^a$ is H or C$_{1-6}$alkyl and R$^b$ is R$^6$;

alternatively, R$^a$ and R$^b$ taken together with the nitrogen atom to which they are attached form a 4-7 membered monocyclic heterocycle, wherein the C$_{3-8}$-cycloalkyl of the —C(O)—C$_{3-8}$-cycloalkyl and monocyclic heterocycle are optionally substituted with 1-3 substituents of $R^6$, in conjunction with any of the above or below embodiments.

In another embodiment, the compounds of Formulas I, I-A and I-B include compounds wherein each $R^1$ independently, is F, Cl, $CF_3$, $OCF_3$, methyl, ethyl, CN, OH, —$OCH_3$, —$OCF_3$, —$NH_2$, $NHCH_3$ or —$C(O)CH_3$, in conjunction with any of the above or below embodiments.

In another embodiment, the compounds of Formulas I, I-A and I-B include compounds wherein each of $R^1$ is F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the compounds of Formulas I, I-A and I-B include compounds wherein each $R^1$ independently, is F, Cl, Br, $CF_3$, $OCF_3$, $C_{1-6}$-alkyl, CN, OH, —$OC_{1-6}$-alkyl, —$S(O)_nC_{1-6}$-alkyl, —$NH_2$, CN, —$NHC_{1-6}$-alkyl, —$C(O)C_{1-6}$-alkyl, —$C(O)C_{1-6}$-cycloalkyl, —C(O)-tetrahydropyrrole, in conjunction with any of the above or below embodiments.

In another embodiment, the compounds of Formulas I and I-A include compounds wherein each $R^2$, independently, is H, $C_{1-3}$alkyl or halo, in conjunction with any of the above or below embodiments.

In another embodiment, the compounds of Formulas I and I-A include compounds wherein each $R^2$, independently, is H, $CH_3$, $CH_2CH_3$, F or Cl, in conjunction with any of the above or below embodiments.

In another embodiment, the compounds of Formulas I and I-A include compounds wherein each $R^2$, independently, is H, in conjunction with any of the above or below embodiments.

In another embodiment, the compounds of Formulas I and I-A include compounds wherein each $R^3$ independently is H, $C_{1-6}$alkyl, $C_{3-6}$cycloalkyl, —OH, —$OC_{1-4}$alkyl, halo, haloalkyl, CN, —$NH_2$ or —$NHC_{1-6}$alkyl, in conjunction with any of the above or below embodiments.

In another embodiment, the compounds of Formula I or I-A includes compounds wherein each $R^3$ independently is H or methyl, in conjunction with any of the above or below embodiments.

In another embodiment, the compounds of Formula I, I-A and I-B include compounds wherein $R^4$ is H or methyl, in conjunction with any of the above or below embodiments.

In another embodiment, the compounds of Formula I, I-A and I-B include compounds wherein $R^4$ is H, in conjunction with any of the above or below embodiments.

In another embodiment, the compounds of Formula I, I-A and I-B include compounds wherein $R^5$ is a fully saturated or partially or fully unsaturated 5- or 6-membered monocyclic or bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^6$, in conjunction with any of the above or below embodiments.

In another embodiment, the compounds of Formula I, I-A and I-B include compounds wherein $R^5$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted, independently, with 1-5 substituents of $R^6$, in conjunction with any of the above or below embodiments.

In another embodiment, the compounds of Formula I, I-A and I-B include compounds wherein $R^5$ is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, or a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted, independently, with 1-5 substituents of $R^6$, in conjunction with any of the above or below embodiments.

In another embodiment, the compounds of Formula I or I-A includes compounds wherein $R^5$ is $C_{1-6}$-alkyl, $C_{3-8}$-cycloalkyl or a ring selected from cyclopropyl, cyclobutyl, cyclopentyl, cyclohexyl, phenyl, pyridyl, pyrimidyl, thienyl, furanyl, pyrrolidinyl, pyrazolyl, imidazolyl, triazolyl, tetrazolyl, thiazolyl, oxazolyl, isothiazolyl, isoxazolyl, diazolyl, thiodiazolyl, oxadiazolyl, oxazolinyl, isoxazolinyl, thiazolinyl, pyranyl, pyrazinyl, pyridazinyl, morpholinyl, piperidinyl and piperazinyl, wherein the $C_{1-6}$-alkyl, $C_{3-8}$-cycloalkyl and ring are optionally substituted, independently, with 1-5 substituents of $R^6$, in conjunction with any of the above or below embodiments.

In another embodiment, the compounds of Formula I, I-A and I-B include compounds wherein $R^5$ is $C_{1-4}$alkyl substituted with 1-3 substituents of F, Cl, Br, I, $CF_3$, $C_2F_5$, haloalkoxyl, $C_{1-6}$-alkyl, CN, OH, $OC_{1-6}$-alkyl, $SC_{1-6}$-alkyl, $SC_{1-6}$-alkyl, $S(O)_oC_{1-6}$-alkyl, cycloalkyl, aryl, heteroaryl or heterocyclyl wherein the cycloalkyl, aryl, heteroaryl or heterocyclyl is optionally substituted independently with 1-5 substituents of F, Cl, Br, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-4}$-alkylamino-, $C_{1-4}$-dialkylamino- or $C_{1-4}$-thioalkoxyl, in conjunction with any of the above or below embodiments.

In another embodiment, the compounds of Formula I, I-A and I-B include compounds wherein $R^5$ is a $C_{1-6}$alkyl substituted by a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted, independently, with 1-5 substituents of $R^6$, in conjunction with any of the above or below embodiments.

In another embodiment, the compounds of Formula I, I-A and I-B include compounds wherein $R^4$ and $R^5$ taken together with the nitrogen atom to which they are attached form a 4-7 membered monocyclic heterocycle, optionally substituted with 1-3 substituents of $R^6$, in conjunction with any of the above or below embodiments.

In another embodiment, the compounds of Formula I, I-A and I-B include compounds wherein $R^6$ is F, Cl, Br, I, $CF_3$, $C_2F_5$, haloalkoxyl, $C_{1-6}$-alkyl, CN, OH, $OC_{1-6}$-alkyl, $SC_{1-6}$-alkyl, $SC_{1-6}$-alkyl, $S(O)_oC_{1-6}$-alkyl wherein o is 0, 1 or 2, $NHC_{1-6}$-alkyl or $C(O)C_{1-6}$-alkyl, in conjunction with any of the above or below embodiments.

In another embodiment, the invention provides the compound of Formula I, I-A or I-B, or a stereoisomer or pharmaceutically acceptable salt thereof, selected from 3-(2-amino-6-o-tolylquinolin-3-yl)-N-cyclohexylpropanamide;

3-(2-amino-6-o-tolylquinolin-3-yl)-N-(3,3-dimethylbutyl) propanamide;

3-(2-amino-6-o-tolylquinolin-3-yl)-N-(cyclohexylmethyl)-2-methylpropanamide;
3-(2-amino-6-o-tolylquinolin-3-yl)-N-benzylpropanamide;
3-(2-amino-6-o-tolylquinolin-3-yl)-N-(2-cyclohexylethyl)propanamide;
3-(2-amino-6-(3-methylpyridin-2-yl)quinolin-3-yl)-N-(3,3-dimethylbutyl)-2-methylpropanamide;
3-(2-amino-6-o-tolylquinolin-3-yl)-2-methyl-N-(1-methylpiperidin-3-yl)propanamide;
3-(3-amino-7-o-tolylnaphthalen-2-yl)-2-methyl-N-(pyridin-3-ylmethyl)propanamide;
(R)-3-(2-amino-6-o-tolylquinolin-3-yl)-2-methyl-N-(pyrazin-2-ylmethyl)propanamide;
(R)-3-(2-amino-6-o-tolylquinolin-3-yl)-2-methyl-N-(pyridazin-3-ylmethyl)propanamide;
(R)-3-(2-amino-6-o-tolylquinolin-3-yl)-2-methyl-N-(pyrimidin-4-ylmethyl)propanamide;
(R)-3-(2-amino-6-o-tolylquinolin-3-yl)-2-methyl-N-(pyrimidin-2-ylmethyl)propanamide;
3-(2-amino-6-(3-methylpyridin-2-yl)quinolin-3-yl)-2-methyl-N—(((R)-tetrahydro-2H-pyran-3-yl)methyl)propanamide;
(R)-3-(2-amino-6-o-tolylquinolin-3-yl)-2-methyl-N-((tetrahydro-2H-pyran-4-yl)methyl)propanamide;
3-(2-amino-6-(3-methylpyridin-2-yl)quinolin-3-yl)-2-methyl-N-((tetrahydro-2H-pyran-4-yl)methyl)propanamide;
3-(2-amino-6-(3-methylpyridin-2-yl)quinolin-3-yl)-2-methyl-N-(((S)-tetrahydro-2H-pyran-3-yl)methyl)propanamide;
3-(2-amino-6-o-tolylquinolin-3-yl)-N-(3,3-dimethylbutyl)-2-methylpropanamide;
3-(2-amino-6-o-tolylquinolin-3-yl)-2-methyl-N-((tetrahydro-2H-pyran-3-yl)methyl)propanamide;
3-(2-amino-6-o-tolylquinolin-3-yl)-2-methyl-N-(thiazol-5-ylmethyl)propanamide;
3-(2-amino-7-fluoro-6-(3-methyl-2-pyridinyl)-3-quinolinyl)-N-(3,3-dimethylbutyl)-2-methylpropanamide;
N-(3-fluoro-3-methylbutyl)-2-methyl-3-(6-(3-methylpyridin-2-yl)quinolin-3-yl)propanamide;
3-(2-amino-6-(3-methylpyridin-2-yl)quinolin-3-yl)-2-methyl-N-(2-(1-methylcyclopropyl)ethyl)propanamide;
3-(2-amino-6-(2-butoxyphenyl)quinolin-3-yl)-N-(cyclohexylmethyl)-2-methylpropanamide;
3-(2-amino-6-(2-((dimethylamino)methyl)phenyl)quinolin-3-yl)-N-(cyclohexylmethyl)-2-methylpropanamide;
3-(2-amino-6-(3-methylpyridin-2-yl)quinolin-3-yl)-N-isopentyl-2-methylpropanamide;
3-(2-amino-6-(3-methylpyridin-2-yl)quinolin-3-yl)-2-methyl-N-(3,3,3-trifluoropropyl)propanamide;
3-(2-amino-6-(3-methylpyridin-2-yl)quinolin-3-O—N-((4,4-difluorocyclohexyl)methyl)-2-methylpropanamide;
3-(2-amino-6-(pyridin-2-yl)quinolin-3-yl)-N-(3,3-dimethylbutyl)-2-methylpropanamide;
3-(2-amino-6-(3-(2-morpholinoethyl)pyridin-2-yl)quinolin-3-yl)-N-(3,3-dimethylbutyl)-2-methylpropanamide;
3-(2-amino-6-(3-(2-(4-methylpiperazin-1-yl)ethyl)pyridin-2-yl)quinolin-3-yl)-N-(3,3-dimethylbutyl)-2-methylpropanamide;
3-(2-amino-6-(3-(2-(pyrrolidin-1-yl)ethyl)pyridin-2-yl)quinolin-3-yl)-N-(3,3-dimethylbutyl)-2-methylpropanamide;
(R)-3-(2-amino-6-(3-methylpyridin-2-yl)quinolin-3-yl)-N-(3,3-dimethylbutyl)-2-methylpropanamide;
3-(2-amino-6-(3-(2-(dimethylamino)ethyl)pyridin-2-yl)quinolin-3-yl)-N-(3,3-dimethylbutyl)-2-methylpropanamide;
(R)-3-(2-amino-6-(3-chloropyridin-2-yl)quinolin-3-yl)-N-(3,3-dimethylbutyl)-2-methylpropanamide;
3-(2-amino-6-o-tolyl-1,7-naphthyridin-3-yl)-N-(3,3-dimethylbutyl)-2-methylpropanamide;
3-(2-amino-6-(2-methylphenyl)-3-quinolinyl)-N-(3-hydroxy-3-methylbutyl)propanamide;
3-(2-amino-6-(2-cyanophenyl)-3-quinolinyl)-N-(2,2-dimethyltetrahydro-2H-pyran-4-yl)-2-methylpropanamide;
3-(6-(2-acetylphenyl)-2-amino-3-quinolinyl)-N-(2,2-dimethyltetrahydro-2H-pyran-4-yl)-2-methylpropanamide;
(2R)-3-(2-amino-6-o-tolylquinolin-3-yl)-N-(cis-2,6-dimethyltetrahydro-2H-pyran-4-yl)-2-methylpropanamide;
3-(2-amino-6-(2-methyl-6-(1-pyrrolidinylcarbonyl)phenyl)-3-quinolinyl)-N-(2,2-dimethyltetrahydro-2H-pyran-4-yl)-2-methylpropanamide;
3-(2-amino-6-(2-((2-methoxyphenyl)carbonyl)phenyl)-3-quinolinyl)-N-(2,2-dimethyltetrahydro-2H-pyran-4-yl)-2-methylpropanamide;
3-(2-amino-6-(2-(cyclohexylcarbonyl)phenyl)-3-quinolinyl)-N-(2,2-dimethyltetrahydro-2H-pyran-4-yl)-2-methylpropanamide;
3-(2-Amino-6-(2-methyl-6-(pyrrolidine-1-carbonyl)phenyl)quinolin-3-yl)-N, 2-dimethylpropanamide;
3-(2-amino-6-(2-methyl-6-(pyrrolidine-1-carbonyl)phenyl)quinolin-3-yl)-2-methyl-N-(pyridin-2-ylmethyl)propanamide;
3-(2-amino-6-(2-methyl-6-(pyrrolidine-1-carbonyl)phenyl)quinolin-3-yl)-N-cyclopropyl-2-methylpropanamide;
3-(2-amino-6-(2-methyl-6-(pyrrolidine-1-carbonyl)phenyl)quinolin-3-yl)-N-benzyl-2-methylpropanamide;
3-(6-(2-acetylphenyl)-2-aminoquinolin-3-yl)-2-methyl-N-phenylpropanamide;
3-(2-amino-6-(2-methyl-6-(pyrrolidine-1-carbonyl)phenyl)quinolin-3-yl)-2-methyl-N-phenylpropanamide;
(2R)-3-(2-amino-6-o-tolylquinolin-3-yl)-2-methyl-N-(2-methyltetrahydro-2H-pyran-4-yl)propanamide;
3-(2-amino-6-(2,3-dichlorophenyl)quinolin-3-yl)-N-(2,2-dimethyltetrahydro-2H-pyran-4-yl)-2-methylpropanamide;
(R)-3-(2-amino-6-o-tolylquinolin-3-yl)-N-(cis-2-ethynyltetrahydro-2H-pyran-4-yl)-2-methylpropanamide;
3-(2-amino-6-(2,3-dichlorophenyl)quinolin-3-yl)-2-methyl-N-(5-oxaspiro[3.5]nonan-8-yl)propanamide;
(2R)-3-(2-amino-6-(2-methylphenyl)-3-quinolinyl)-N-(3,3-dimethylcyclohexyl)-2-methylpropanamide;
3-(2-amino-6-(2-methylphenyl)-3-quinolinyl)-N-(3,3-dimethylcyclohexyl)propanamide;
3-(2-amino-6-(2-methylphenyl)-3-quinolinyl)-N-(-2,2-dimethyltetrahydro-2H-pyran-4-yl)propanamide;
(2R)-3-(2-amino-6-o-tolylquinolin-3-yl)-N-(2,2-dimethyltetrahydro-2H-pyran-4-yl)-2-methylpropanamide;
3-(2-amino-6-(4-chlorophenyl)-3-quinolinyl)-N-(2,2-dimethyltetrahydro-2H-pyran-4-yl)-2-methylpropanamide;
3-(2-amino-6-(3-chlorophenyl)-3-quinolinyl)-N-(2,2-dimethyltetrahydro-2H-pyran-4-yl)-2-methylpropanamide;
(2R)-3-(2-amino-6-(2-methylphenyl)-3-quinolinyl)-2-methyl-N-(5-oxaspiro[3,5]non-8-yl)propanamide; and
3-(2-amino-6-(3-chlorophenyl)-3-quinolinyl)-2-methyl-N-(5-oxaspiro[3,5]non-8-yl)propanamide.

In another embodiment, the invention provides each of the Examplary compounds, and stereoisomers, tautomers, solvates, pharmaceutically acceptable salts, derivatives or prodrugs thereof, and related intermediates, described herein.

In another embodiment, the invention provides the exemplified compounds described herein, and stereoisomers and pharmaceutically acceptable salt forms of each thereof.

DEFINITIONS

The following definitions should assist in understanding the invention described herein.

The term "comprising" is meant to be open ended, i.e., all encompassing, all inclusive and non-limiting. It may be used herein synonymously with "having" or "including." "Comprising" is intended to include each and every indicated or recited component or element(s) while not excluding any other components or elements.

The term "$C_{\alpha\text{-}\beta}$alkyl", when used either alone or within other terms such as "haloalkyl" and "alkylamino", embraces linear or branched radicals having $\alpha$ to $\beta$ number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha\text{-}\beta}$alkenyl", when used alone or in combination, embraces linear or branched radicals having at least one carbon-carbon double bond in a moiety having a number of carbon atoms in the range from $\alpha$ and $\beta$. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha\text{-}\beta}$alkynyl", when used alone or in combination, denotes linear or branched radicals having at least one carbon-carbon triple bond in a moiety having a number of carbon atoms in the range from $\alpha$ and $\beta$. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha\text{-}\beta}$-alkyl", "$C_{\alpha\text{-}\beta}$-alkenyl" and "$C_{\alpha\text{-}\beta}$-alkynyl", when used with other terms such as "wherein 1, 2 or 3 carbon atoms of said $C_{\alpha\text{-}\beta}$-alkyl, $C_{\alpha\text{-}\beta}$-alkenyl or $C_{2\alpha\text{-}\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include —O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR$^7$ where R$^7$ may be defined as a $C_{\alpha\text{-}\beta}$-alkyl. Examples of such "alkenyl" radicals include —NH—CH$_2$CH=CH$_2$, —S—CH$_2$CH$_2$CH=CHCH$_3$ and the like. Similar examples exist for such "alkynyl" radicals, as appreciated by those skilled in the art.

The term "$C_{\alpha\text{-}\beta}$alkoxyl" when used alone or in combination, embraces linear or branched oxygen-containing alkyl radicals each having $\alpha$ to $\beta$ number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy, fluoropropoxy and cyclopropylmethoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "carbocyclic" or "carbocyclyl", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The phrase "a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S" as used herein is intended to encompass all monocyclic and bicyclic rings as small as three atoms to as large as 12 atoms in size, including both carbocyclic rings and heterocyclic, aromatic and non-aromatic rings. The non-aromatic rings may be partially or fully saturated in nature.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "aminocarbonyl" denotes an amide group of the formula —C(=O)NH$_2$.

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, (CH$_3$S—).

The term "Formula I" includes any sub formulas, such as Formulas I-A and Formulas I-B.

The term "pharmaceutically-acceptable" when used with reference to a compound of Formulas I, I-A and I-B is intended to refer to a form of the compound that is safe for administration. For example, a salt form, a solvate, a hydrate, a prodrug or derivative form of a compound of Formulas I, I-A and I-B, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I, I-A and I-B are the pharmaceutically acceptable salt forms of the free-base compounds. The term "pharmaceutically-acceptable salts"

embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I, I-A and I-B may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I, I-A and I-B include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I, I-A and I-B.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is intended to encompass any salt of a compound of this invention, any ester of a compound of this invention, or any other compound, which upon administration to a patient is capable of providing (directly or indirectly) a compound of this invention, or a metabolite or residue thereof, characterized by the ability of the derivative to modulate an enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formulas I, I-A and I-B. A "pharmaceutically-acceptable prodrug" as used herein, denotes a prodrug which is pharmaceutically acceptable. Pharmaceutically acceptable modifications to the compounds of Formula I, I-A and I-B are readily appreciated by those of ordinary skill in the art.

The compound(s) of Formulas I, I-A and I-B may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I, I-A and I-B. The compounds of Formulas I, I-A and I-B can be synthesized according to the procedures described in the following Schemes I-XI, wherein the substituents are as defined for Formulas I, I-A and I-B above, except where further noted. The synthetic methods described below are merely exemplary, and the compounds of the invention may also be synthesized by alternate routes utilizing alternative synthetic strategies, as appreciated by persons of ordinary skill in the art. The following list of abbreviations used throughout the specification represent the following and should assist in understanding the invention:

ACN, MeCN—acetonitrile
Aq., aq.—aqueous
Ar—argon (gas)
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide
DCC—dicyclohexylcarbodiimide
DIC—1,3-diisopropylcarbodiimide
DIEA, DIPEA—N,N-diisopropylethylamine
DME—dimethoxyethane
DMF—N,N-dimethylformamide
DMAP—4-dimethylaminopyridine
DMS—dimethylsulfide
DMSO—dimethylsulfoxide
EDC, EDCI—1-(3-dimethylaminopropyl)-3-ethylcarbodiimide
$Et_2O$—diethyl ether
EtOAc—ethyl acetate
FBS—fetal bovine serum
G, gm—gram
h, hr—hour
$H_2$—hydrogen
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol
$N_2$—nitrogen
$NaCNBH_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH—sodium hydroxide
$Na_2SO_4$—sodium sulfate
$NH_4Cl$—ammonium chloride
$NH_4OH$—ammonium hydroxide
NMP—N-methylpyrrolidine
$P(t-bu)_3$—tri(tert-butyl)phosphine
PBS phospate—buffered saline
Pd/C—palladium on carbon
$Pd(PPh_3)_4$—palladium(0)triphenylphosphine tetrakis
$Pd(dppf)Cl_2$—palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone)dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography
TBAF—Tetrabutylammonium flouride
TBTU—O-benzotriazol-1-yl-N,N,N,N'-tetramethyluronium tetrafluoroborate
TEA, $Et_3N$—triethylamine
TFA—trifluoroacetic acid
THF—tetrahydrofuran
UV—ultraviolet light

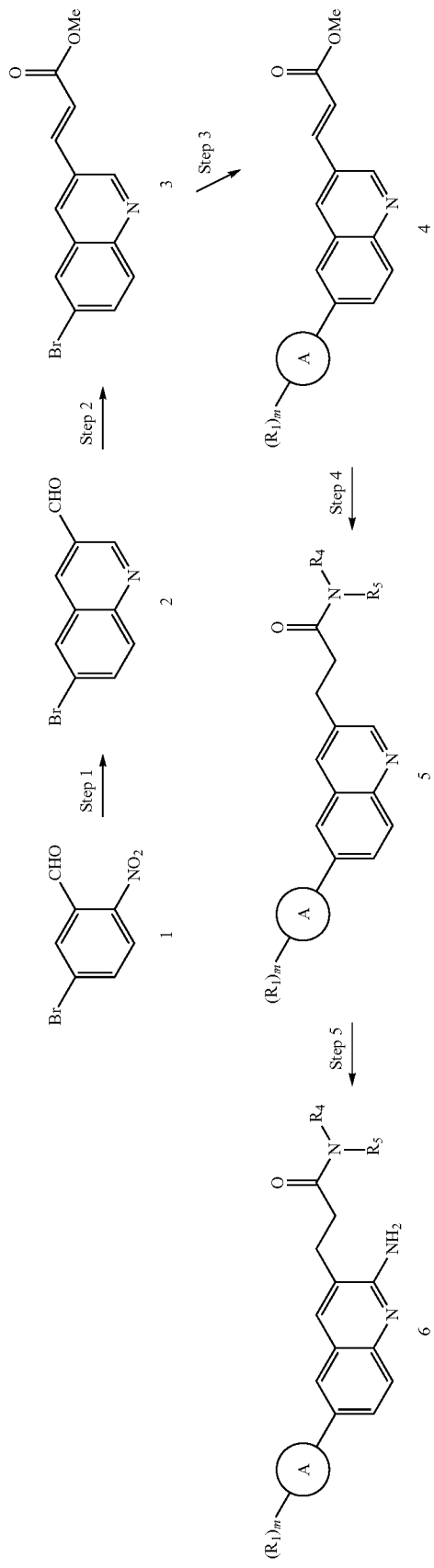

Compounds 6 of Formulas I, I-A and I-B may be prepared by the general method illustrated in scheme 1 above and described step-by-step below.

Step 1

5-Bromo-2-nitrobenzaldehyde 1 (6.03 g, 26.2 mmol) was dissolved in MeOH (200 mL) and treated with 5N HCl (10 mL). The mixture was heated to 70° C. and iron powder (7.32 g, 131 mmol) was added in five portions every 5 min. Upon completion (by TLC) the reaction was cooled and DCM (200 mL) was added before filtering through a pad of celite. The filtrate was concentrated under reduced pressure to 150 mL. To this material, a solution of 1,1,3,3-tetramethoxypropane (9.52 ml, 57.7 mmol) in 5N HCl (10 mL) pre-mixed for 45 min was added. The reaction mixture was stirred at 80° C. for 60 min. Toluene (100 mL) and acetic acid (40 mL) were added and the solution was heated to 110° C. for 3 h, then cooled and evaporated to dryness under reduced pressure. The crude material was purified using silica chromatography (20-60% ethyl acetate in hexane gradient) to give 6-bromo-quinoline-3-carbaldehyde 2.

Step 2

6-Bromoquinoline-3-carbaldehyde 2 (2.8 g, 12.0 mmol) and methyl(triphenylphosphoranylidene)acetate (4.0 g, 12.0 mmol) were dissolved in dry THF (50 mL) and heated to 50° C. After 40 min the solution was evaporated to dryness under reduced pressure. Purification using silica chromatography (hexane to 60% ethyl acetate in hexane gradient) gave methyl 3-(6-bromoquinolin-3-yl)acrylate 3 as a mixture of E and Z isomers.

Step 3

Methyl 3-(6-bromoquinolin-3-yl)acrylate 3 (0.91 g, 3.1 mmol), 2-methylphenyl boronic acid ($R^1$ substituted ring A in 4 above; 0.61 g), potassium acetate (1.0 g) and bis(4-(di-tert-butylphosphino)-N,N-dimethylbenzenamine)dichloropalladium (II) (0.19 g) were suspended in ethanol (70 mL) and water (5 mL) and heated to reflux for 90 min. LC/MS showed the bromoquinoline had been consumed the reaction was evaporated to dryness under reduced pressure. The crude was partitioned between ethyl acetate and water. The organic layer was separated and dried with magnesium sulfate, evaporated to dryness under reduced pressure and purified using silica chromatography (hexane to ethyl acetate gradient) to give methyl 3-(6-o-tolylquinolin-3-yl)acrylate 4 (representative compound 4 wherein ring A is ortho-toluene).

The boronic acid, and ester, intermediates may be prepared by methods described in the following references: (1) PCT Int. Patent Appl. No. WO 2005073189, titled "Preparation of fused heteroaryl derivatives as p38 kinase inhibitors" or (2) PCT Int. Patent Appl. No. WO 2006094187, titled "Preparation of phthalazine, aza- and diaza-phthalazine compounds as protein kinase, especially p38 kinase, inhibitors for treating inflammation and related conditions". Also, desired boronic acids may be commercially purchased or internally prepared as needed.

Step 3 involves a boronic acid coupling reaction, similar to classic Suzuki reactions using a borane reagent and a suitable aromatic bromide, such as the Br-quinoline 3 (Br is a suitable halogen leaving group "LG"). As appreciated to one of ordinary skill in the art, Suzuki and Suzuki-like reactions also utilize a palladium catalyst. Suitable palladium catalysts include, without limitation, $Pd(PPh_3)_4$, $Pd(OAc)_2$ or $Pd(dppf)Cl_2$. Where LG is a halide, the halide may be an iodide, a bromide or even a chloride. Chloro-pyridyl rings (where $A^1$=N) undergo Suzuki reactions in the presence of $Pd(OAc)_2$. Other LGs are also suitable. For example, Suzuki couplings are known to occur with a sulfonate, such as trifluoromethanesulfonate, as the leaving group.

The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Alternatively, the reaction may simply require solvent and heat depending upon the particular bromide 3 and/or boronic acid or ester, as appreciated by those skilled in the art.

Other alternative methods of preparing the desired aromatic ring are also known. For example metal coupling chemistry, such Stille, Kumada, Negishi coupling methods, and the like, may be employed to prepare desired products 6.

Step 4

Lithium hydroxide monohydrate (0.42 g) (solution in water, 10 mL) was added to a solution of methyl 3-(6-o-tolylquinolin-3-yl)acrylate 4 (0.32 g, 1.05 mmol) in methanol (50 mL) and heated to 50° C. The reaction was monitored by TLC and once the ester had been consumed, 5N HCl (2 mL) was added and the mixture was concentrated to dryness under reduced pressure. The crude acid was dried under high vac then dissolved in thionyl chloride (30 mL) and heated to 80° C. for 1 h. The solution was evaporated to dryness under reduced pressure and the crude acid chloride dissolved in DCM (50 mL). A solution of N-methylcyclohexylamine (660 uL) and N,N-diisopropylethylamine (850 uL) in DCM (10 mL) was added slowly and the mixture stirred for 15 min. Additional DCM (50 mL) and water (80 mL) were added and the phases were separated. The organic layer was dried with magnesium sulfate and evaporated to dryness under reduced pressure. Purification using silica chromatography (hexane to ethyl acetate gradient) gave the desired amide. This material was dissolved in methanol (50 mL) and treated with 10 wt % palladium on carbon (0.12 g). The mixture was hydrogenated at 50 psi for 30 min until the reduction was complete by LC/MS. The mixture was filtered through a pad of celite and evaporated to dryness under reduced pressure. Purification using silica chromatography (hexane to ethyl acetate gradient) gave N-cyclohexyl-N-methyl-3-(6-O— tolylquinolin-3-yl)propanamide (representative compound 5).

Step 5

N-Cyclohexyl-N-methyl-3-(6-o-tolylquinolin-3-yl)propanamide (0.13 g) and m-chloroperbenzoic acid (0.11 g) were dissolved in chloroform and heated to reflux for 10 min. DCM (30 mL) and 1N NaOH (70 mL) were added and the phases mixed and separated. The organic layer was dried with magnesium sulfate and evaporated to dryness under reduced pressure. The crude N-oxide was dissolved in a mixture of trifluoromethylbenzene (20 mL) and tert-butylamine (0.20 mL), then p-toluenesulfonic anhydride (0.15 g) was added. The mixture was stirred until LC/MS analysis showed the desired amine had formed. Water (100 mL), 5N NaOH (30 mL), and DCM (70 mL) were added and the phases were separated. The organic layer was dried with magnesium sulfate before evaporating to dryness. Purification using silica chromatography (hexane to ethyl acetate gradient) gave the 2-(tert-butylamino)-quinoline. This material was dissolved in TFA (30 mL) and heated to reflux. After the deprotection was complete by LC/MS, the solution was evaporated to dryness under reduced pressure and the crude material was basified using saturated sodium bicarbonate and dichloromethane. Silica purification (0-10% MeOH in DCM gradient) gave 3-(2-amino-6-o-tolylquinolin-3-yl)-N-cyclohexyl-N-methylpropanamide (representative compound 6 of Formulas I, I-A and I-B). MS (ESI, pos. ion) m/z: 402 (M+1).

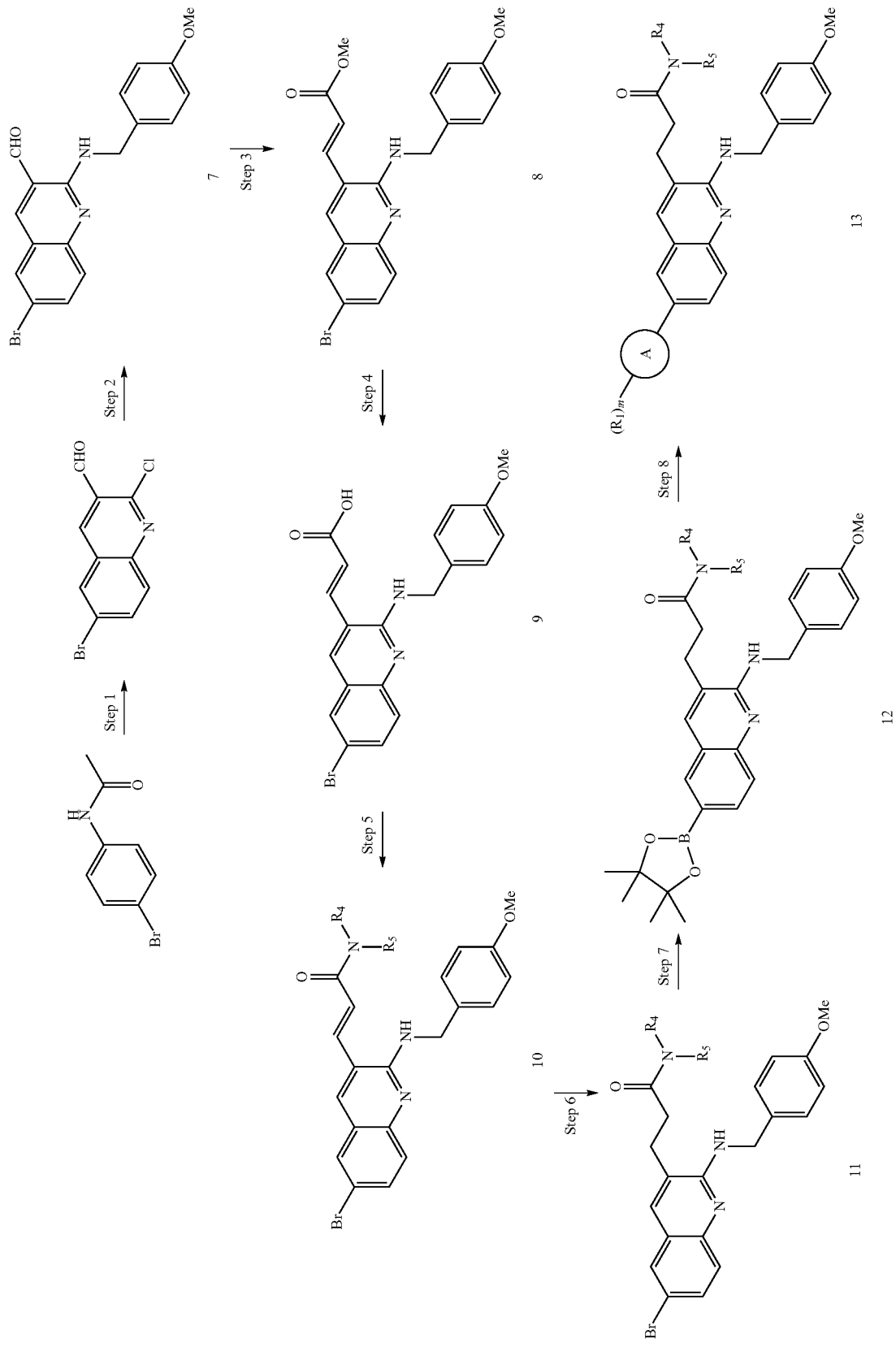

-continued
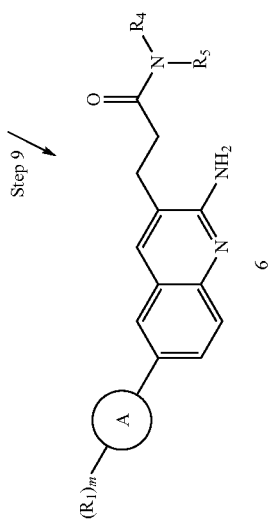

Compounds 6 of formulas I, I-A and I-B may also be prepared by the method illustrated in scheme II and described step-by-step below.

Step 1

DMF (54 ml, 701 mmol, 2.5 eq.) was added dropwise (via a syringe pump) to phosphoryl trichloride (179 ml, 1962 mmol, 7.0 eq.) in a 350 mL sealed tube in an ice bath under nitrogen. After the addition, the water bath was removed and N-(4-bromophenyl)acetamide (60 g, 280 mmol) was added in one portion and the resulting mixture was stirred until a homogenous solution was observed (approx. 30 min.). The reaction vessel was sealed and heated at 75° C. for 48 h. The reaction was allowed to cool and slowly poured onto ice (final volume of 2 L) and stirred for 25 min. The solid was filtered and washed with water until the filtrate was no longer acidic (~3 L) and the product was dried in an oven vacuum overnight at 50° C. to afford a light tan/gold colored solid, 6-bromo-2-chloroquinoline-3-carbaldehyde.

Step 2

6-Bromo-2-chloroquinoline-3-carbaldehyde (10.0 g, 37.0 mmol) and 4-methoxybenzylamine (14.4 ml, 110.9 mmol) in EtOH (200 mL) was heated at 125° C. in a sealed tube for 2.5 hours. The reaction mixture was cooled and poured into 1N HCl (200 mL) and stirred 2 h. The mixture was extracted with chloroform and the combined organic layers was washed with 1N HCl and brine, dried over sodium sulfate, filtered and concentrated to afford 2-(4-methoxybenzylamino)-6-bromoquinoline-3-carbaldehyde 7.

Step 3

Methyl(triphenylphosphoranylidene)acetate (13.4 g, 40.0 mmol) was added to a solution of 2-(4-methoxybenzylamino)-6-bromoquinoline-3-carbaldehyde 7 (12.4 g, 33.4 mmol) in THF (200 mL) and the reaction was heated to 70° C. for 2.5 h. The reaction was concentrated and dissolved in a minimal amount of DCM and loaded onto a filter plug of silica washed with hexanes. The product was eluted with 4:1 Hex/EtOAc to give (E)-methyl 3-(2-(4-methoxybenzylamino)-6-bromoquinolin-3-yl)acrylate 8.

Step 4

A 1M aqueous solution of LiOH (8.9 mL, 8.9 mmol) was added to a solution of (E)-methyl 3-(2-(4-methoxybenzylamino)-6-bromoquinolin-3-yl)acrylate 8 (3.8 g, 8.9 mmol) in MeOH (9 mL) and THF (30 mL) at RT. The reaction was stirred 45 min before the organics were removed in vacuo and the remaining aqueous solution was brought to a pH ~1 with 1N HCl aq and the solution was extracted with a 2:1 chloroform/i-PrOH mixture. The combined organics were washed with brine, dried over sodium sulfate, filtered, and concentrated to afford compound 9, which was used without further purification.

Step 5

O-(Benzotriazol-1-yl)-N,N,N' N'-tetramethyluronium tetrafluoroborate (0.15 g, 0.47 mmol) was added to a solution of (E)-3-(2-(4-methoxybenzylamino)-6-bromoquinolin-3-yl) acrylic acid 9 (0.15 g, 0.36 mmol), cyclohexylmethanamine (0.14 ml, 1.1 mmol), and N,N-diisopropylethylamine (0.25 mL, 1.5 mmol) in NMP (1.2 mL) and the reaction was stirred 1 h before being poured into a vigorously stirred solution of saturated aqueous sodium bicarbonate. After 30 min, the mixture was diluted with ethyl acetate. The layers were separated and the aqueous layer was extracted with ethyl acetate. The combined organic layers were washed with water, brine, dried over sodium sulfate, filtered, and concentrated to afford (E)-3-(2-(4-methoxybenzylamino)-6-bromoquinolin-3-yl)-N-(cyclohexylmethyl)acrylamide (representative compound 10).

Step 6

Platinum, 5 wt. % on activated carbon, (1.8 g, 9.0 mmol) was added to a degassed solution of (E)-3-(2-(4-methoxybenzylamino)-6-bromoquinolin-3-yl)-N-(cyclohexylmethyl)acrylamide (4.6 g, 9.0 mmol) in EtOH (100 mL). The flask was degassed with hydrogen gas and then stirred under a balloon of hydrogen 18 h. The reaction was purged with nitrogen and filtered through a pad of celite with ethanol and concentrated. The crude product was purified by silica gel chromatography with 1.5:1 Hexene/EtOAc to afford 3-(2-(4-methoxybenzylamino)-6-bromoquinolin-3-yl)-N-(cyclohexylmethyl)propanamide (representative compound 11).

Step 7

Dichloro 1,1'-bis(diphenylphosphino)ferrocene palladium (0.096 g, 0.12 mmol) was added to a solution of (E)-3-(2-(4-methoxybenzylamino)-6-bromoquinolin-3-yl)-N-(3,3-dimethylbutyl)-2-methylacrylamide (1.2 g, 2.4 mmol), potassium acetate (0.69 g, 7.1 mmol), and 4,4,5,5-tetramethyl-2-(4,4,5,5-tetramethyl-1,3,2-dioxaborolan-2-yl)-1,3,2-dioxaborolane (0.72 g, 2.8 mmol) in dioxane (20 mL). The solution was heated at 85° C. for 4 h. The reaction was cooled and concentrated. The crude product was diluted with ethyl acetate and filtered. The filtrate was concentrated to afford 3-(2-(4-methoxybenzylamino)-6-(4,4,5,5-tetramethyl-1,3,2-dioxaborolan-2-yl)quinolin-3-yl)-N-(cyclohexylmethyl) propanamide (representative compound 12), which was used without further purification.

Step 8

Bis(4-(di-tert-butylphosphino)-N,N-dimethylbenzenamine) dichloropalladium (II) (0.0064 g, 0.0090 mmol) was added to a degassed solution of 3-(2-(4-methoxybenzylamino)-6-(4,4,5,5-tetramethyl-1,3,2-dioxaborolan-2-yl)quinolin-3-yl)-N-(cyclohexylmethyl)propanamide (0.10 g, 0.18 mmol), potassium acetate (0.035 g, 0.36 mmol), and 4-bromothiazole (0.024 mL, 0.27 mmol) in EtOH (1.7 mL) and water (0.30 mL). The reaction was refluxed 5 h until determined to be complete by LC/MS. After cooling, the reaction was partitioned between DCM and a 9:1 saturated aqueous ammonium chloride/ammonium hydroxide solution. The aqueous layer was extracted with DCM and the combined organics were washed with a 9:1 saturated ammonium chloride/ammonium hydroxide solution, water, brine, dried over sodium sulfate, filtered, and concentrated to afford 3-(2-amino-6-(thiazol-4-yl)quinolin-3-yl)-N-(cyclohexylmethyl)propanamide (representative compound 13).

Step 9

3-(2-(4-Methoxybenzylamino)-6-(thiazol-4-yl)quinolin-3-yl)-N-(cyclohexylmethyl)propanamide (0.070 g, 0.14 mmol) was refluxed in TFA (5.0 mL, 65 mmol) for 3 hours. The reaction was concentrated and the crude material was purified by reversed phase HPLC (10:100, 20 minutes) to afford the desired compound (representative compound 6). MS (ESI, pos. ion) m/z: 395 (M+1).

Scheme III

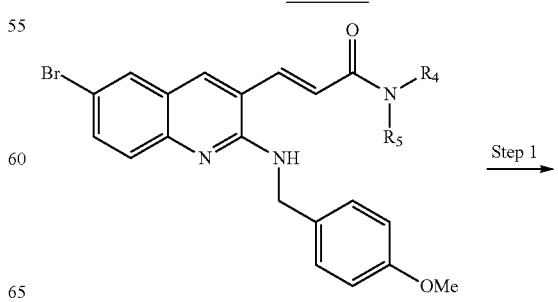

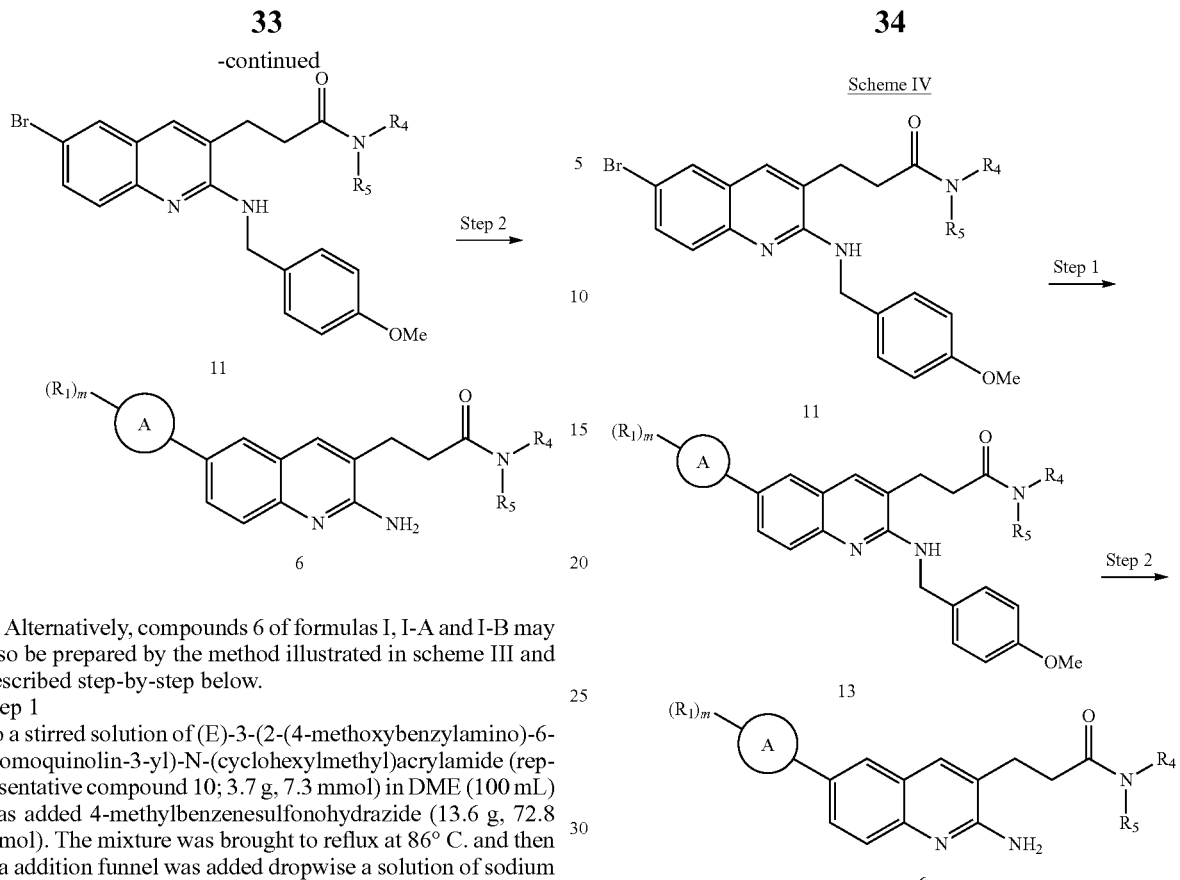

Alternatively, compounds 6 of formulas I, I-A and I-B may also be prepared by the method illustrated in scheme III and described step-by-step below.

Step 1

To a stirred solution of (E)-3-(2-(4-methoxybenzylamino)-6-bromoquinolin-3-yl)-N-(cyclohexylmethyl)acrylamide (representative compound 10; 3.7 g, 7.3 mmol) in DME (100 mL) was added 4-methylbenzenesulfonohydrazide (13.6 g, 72.8 mmol). The mixture was brought to reflux at 86° C. and then via addition funnel was added dropwise a solution of sodium acetate (10.4 g, 127 mmol) in water (60 mL) over 1.5 h. Once the addition was complete, the reaction was refluxed for an additional 30 min, and then cooled to RT and concentrated to remove organic solvent. The crude material was dissolved in DCM (150 mL) and washed sequentially with 1N NaOH, 1N HCl, and then water. The organic layer was dried over MgSO$_4$, filtered and concentrated to give a yellow oil. Purification via flash chromatography (5% EtOAc/dichloromethane) afforded 3-(2-(4-methoxybenzylamino)-6-bromoquinolin-3-yl)-N-(cyclohexylmethyl)propanamide (representative compound 11).

Step 2

In a sealed tube was combined 3-(2-(4-methoxybenzylamino)-6-bromoquinolin-3-yl)-N-(cyclohexylmethyl)propanamide (0.16 g, 0.31 mmol), 2-chlorophenylboronic acid (0.074 g, 0.47 mmol), bis(di-tert-butyl(4-dimethylaminophenyl)phosphine)dichloropalladium(II) (0.0044 g, 0.0063 mmol), potassium acetate (0.062 g, 0.63 mmol), EtOH (6.0 ml) and water (0.41 mL). The flask was sealed and heated in an oil bath at 85° C. for 16 h. The reaction mixture was cooled to RT, adsorbed onto silica and purified by flash chromatography (5% MeOH/dichloromethane) to afford 3-(2-(4-methoxybenzylamino)-6-(2-chlorophenyl)quinolin-3-yl)-N-(cyclohexylmethyl)propanamide.

Step: 3

Following the same procedure as in Step 9 of Scheme II, 3-(2-amino-6-(2-chlorophenyl)quinolin-3-yl)-N-(cyclohexylmethyl)propanamide (representative compound 6) was obtained after 3 hours of refluxing in TFA. MS (ESI, pos. ion) m/z: 422 (M+1).

Alternatively, compounds 6 of formulas I, I-A and I-B may also be prepared by the method illustrated in scheme IV and described step-by-step below.

Step 1

In a sealed tube was combined 3-(2-(4-methoxybenzylamino)-6-bromoquinolin-3-yl)-N-(cyclohexylmethyl)propanamide (0.32 g, 0.63 mmol, prepared as in Example 5), copper (II) acetate monohydrate (0.025 g, 0.13 mmol), cesium carbonate (0.61 g, 1.9 mmol), hippuric acid (0.016 ml, 0.13 mmol), 2-methyl-/H-imidazole (0.062 g, 0.75 mmol) and DMF (5 mL). The tube was sealed and heated to 140° C. for 48 h. The mixture was cooled to RT, transferred to a flask and concentrated to remove the DMF. Adsorbtion onto silica and purification via flash chromatography (slow gradient, 2-10% MeOH/DCM) provided 3-(2-(4-methoxybenzylamino)-6-(2-methyl-1H-imidazol-1-yl) quinolin-3-yl)-N-(cyclohexylmethyl)propanamide (representative compound 13).

Step 2

A solution of 3-(2-(4-methoxybenzylamino)-6-(2-methyl-1H-imidazol-1-yl)quinolin-3-yl)-N-(cyclohexylmethyl)propanamide in TFA (10 mL) was heated at 45° C. for 30 min until complete by LC/MS. After concentrating under reduced pressure to remove the TFA, the oil was dissolved in MeOH and purified by reverse phase HPLC to afford 3-(2-amino-6-(2-methyl-1H-imidazol-1-yl)quinolin-3-yl)-N-(cyclohexylmethyl)propanamide (representative compound 6). MS (ESI, pos. ion) m/z: 392 (M+1).

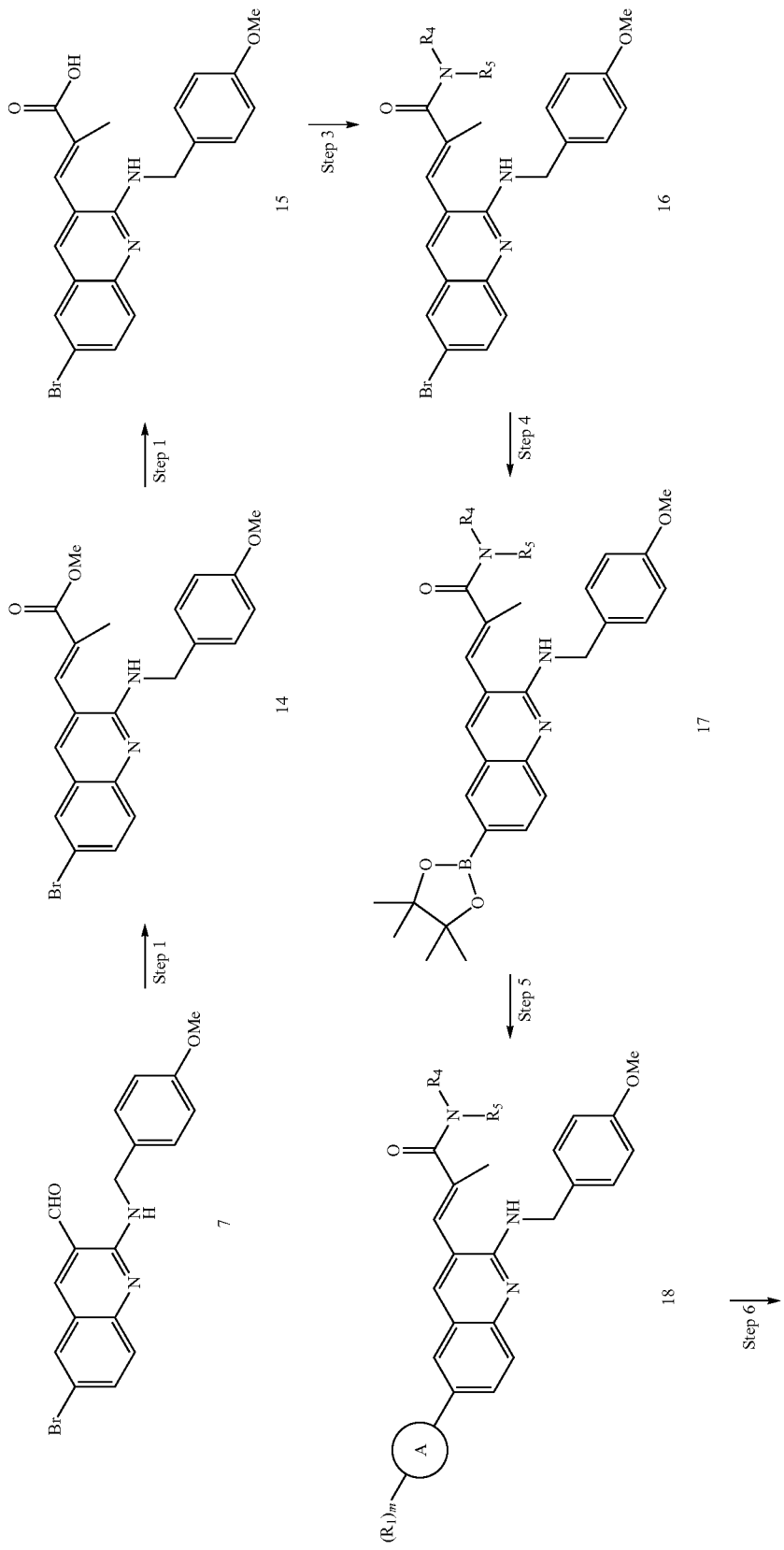

-continued
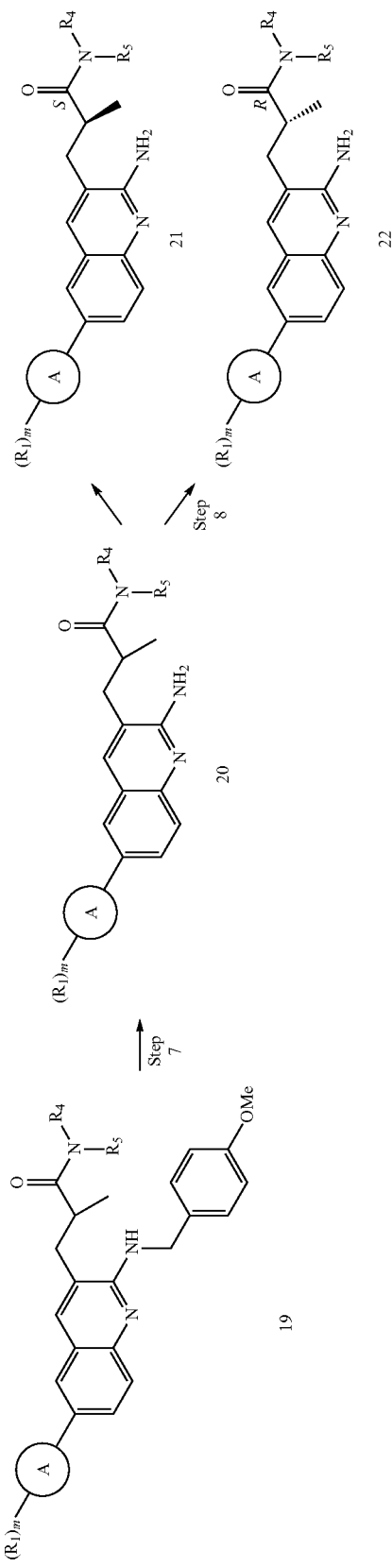

Representative compounds 21 and 22 (wherein $L^1$ is —$CH_2$—$C(CH_3)$—) of formulas I, I-A and II may be prepared by the method illustrated in scheme V and described step-by-step below.

Step 1

Lithium chloride (2.41 g, 56.7 mmol) is stirred 4 h in MeCN (300 mL). To the cloudy solution was added 2-(4-methoxybenzylamino)-6-bromoquinoline-3-carbaldehyde 7 (10.5 g, 28.4 mmol, prepared as in scheme II), ethyl 2-(diethoxyphosphoryl)propanoate (7.4 L, 34.0 mmol) and 2,3,4,6,7,8,9,10-octahydropyrimido[1,2-a]azepine (4.3 ml, 28.4 mmol) and the reaction is stirred 12 h. The reaction is partitioned between 10% sodium carbonate solution and EtOAc. The aqueous layer is extracted with EtOAc and the combined organic layers are washed with 10% sodium carbonate, brine, dried over sodium sulfate, filtered, and concentrated. The crude mixture is purified by silica gel chromatography eluted with 4:1 Hexanes/EtOAc to afford (E)-ethyl 3-(2-(4-methoxybenzylamino)-6-bromoquinolin-3-yl)-2-methylacrylate (representative compound 14).

Step 2

A 1M aqueous solution of LiOH (10.0 ml, 10.0 mmol) was added to a solution of (E)-ethyl 3-(2-(4-methoxybenzylamino)-6-bromoquinolin-3-yl)-2-methylacrylate ((representative compound 14; 3.6 g, 7.9 mmol) in MeOH (10 mL) and THF (30 mL) at RT. The reaction was stirred 1 h. The organic solvent was removed in vacuo and the remaining aqueous solution was brought to a pH ~1 with 1N HCl and the solution was extracted with a 2:1 chloroform/i-PrOH mixture. The combined organics were washed with brine, dried over sodium sulfate, filtered, and concentrated to afford (E)-3-(2-(4-methoxybenzylamino)-6-bromoquinolin-3-yl)-2-methylacrylic acid (representative compound 15) which was used without further purification.

Step 3

TBTU (1.2 g, 3.7 mmol) was added to (E)-3-(2-(4-methoxybenzylamino)-6-bromoquinolin-3-yl)-2-methylacrylic acid (1.2 g, 2.8 mmol), 3,3-dimethylbutylamine (1.1 ml, 8.4 mmol), and DIEA (2.0 ml, 11 mmol) in NMP (10 mL) and the reaction was stirred 1 h. The reaction was poured into a vigorously stirred solution of saturated aqueous sodium bicarbonate and after 30 min was diluted with ethyl acetate. The layers were separated and the aqueous layer was extracted with ethyl acetate. The combined organics were washed with water, brine, and dried over sodium sulfate, filtered, and concentrated to afford (E)-3-(2-(4-methoxybenzylamino)-6-bromoquinolin-3-yl)-N-(3,3-dimethylbutyl)-2-methylacrylamide (representative compound 16) which was used without further purification.

Step 4

(E)-3-(2-(4-methoxybenzylamino)-6-(4,4,5,5-tetramethyl-1,3,2-dioxaborolan-2-yl)quinolin-3-yl)-N-(3,3-dimethylbutyl)-2-methylacrylamide (representative compound 17) was prepared as in Step 7 of Scheme II.

Step 5

Bis(4-(di-tert-butylphosphino)-N,N-dimethylbenzenamine) dichloropalladium (II) (0.041 g, 0.058 mmol) was added to a degassed solution of (E)-3-(2-(4-methoxybenzylamino)-6-(4,4,5,5-tetramethyl-1,3,2-dioxaborolan-2-yl)quinolin-3-yl)-N-(3,3-dimethylbutyl)-2-methylacrylamide (0.65 g, 1.2 mmol), potassium acetate (0.23 g, 2.3 mmol), and 2-bromo-3-methylpyridine (0.20 mL, 1.8 mmol) in EtOH (12 mL) and water (2 mL). The resulting solution was refluxed for 12 h. Then the reaction mixture was cooled and partitioned between DCM and 9:1 saturated ammonium chloride/ammonium hydroxide aqueous solution. The aqueous layer was extracted with DCM and the combined organics were washed with a 9:1 saturated ammonium chloride/ammonium hydroxide solution, water, brine, dried over sodium sulfate, filtered and concentrated. The crude product was purified by silica gel column chromatography (1:1 Hex/EtOAc) to afford (E)-3-(2-(4-methoxybenzylamino)-6-(3-methylpyridin-2-yl)quinolin-3-yl)-N-(3,3-dimethylbutyl)-2-methylacrylamide (representative compound 18).

Step 6

Palladium on carbon (0.71 g, 0.67 mmol) was added to a solution of (E)-3-(2-(4-methoxybenzylamino)-6-(3-methylpyridin-2-yl)quinolin-3-yl)-N-(3,3-dimethylbutyl)-2-methylacrylamide (0.35 g, 0.67 mmol) in EtOH (6 mL). The flask was degassed with hydrogen gas and then stirred under a balloon of hydrogen 12 h. The reaction was filtered through celite and washed with ethanol and ethyl acetate. The filtrate was concentrated to afford 3-(2-(4-methoxybenzylamino)-6-(3-methylpyridin-2-yl)quinolin-3-yl)-N-(3,3-dimethylbutyl)-2-methylpropanamide (representative compound 19) which was used without further purification.

Step 7

TFA (6.0 mL, 78 mmol) was added to 3-(2-(4-methoxybenzylamino)-6-(3-methylpyridin-2-yl)quinolin-3-yl)-N-(3,3-dimethylbutyl)-2-methylpropanamide (0.30 g, 0.57 mmol) and the reaction was heated to 65° C. After 5 h, the reaction was concentrated and the crude material dissolved in DCM. The organic layers were washed with 1N NaOH and the aqueous layer was again extracted with DCM. The combined organic layers were washed with brine, dried over sodium sulfate, and concentrated. The crude product was purified by silica gel column chromatography (20:1 DCM/MeOH with 2M $NH_3$) to afford 3-(2-amino-6-(3-methylpyridin-2-yl)quinolin-3-yl)-N-(3,3-dimethylbutyl)-2-methylpropanamide (representative compound 20). MS (ESI, pos. ion) m/z: 405 (M+1).

Step 8

The product of step 7, a racemic mixture, was purified via preparative Supercritical Fluid Chromatography (SFC), to afford the individual enantiomers. SFC was conducted using 12% isopropanol with 0.2% diethylamine in supercritical carbon dioxide, which provided peak 1 at approximately 4.59 minutes elution time and peak 2 at approximately 5.55 minutes elution time. Peak 1 was identified as the S isomer 21, while peak number 2 was identified as the R isomer, compound 22.

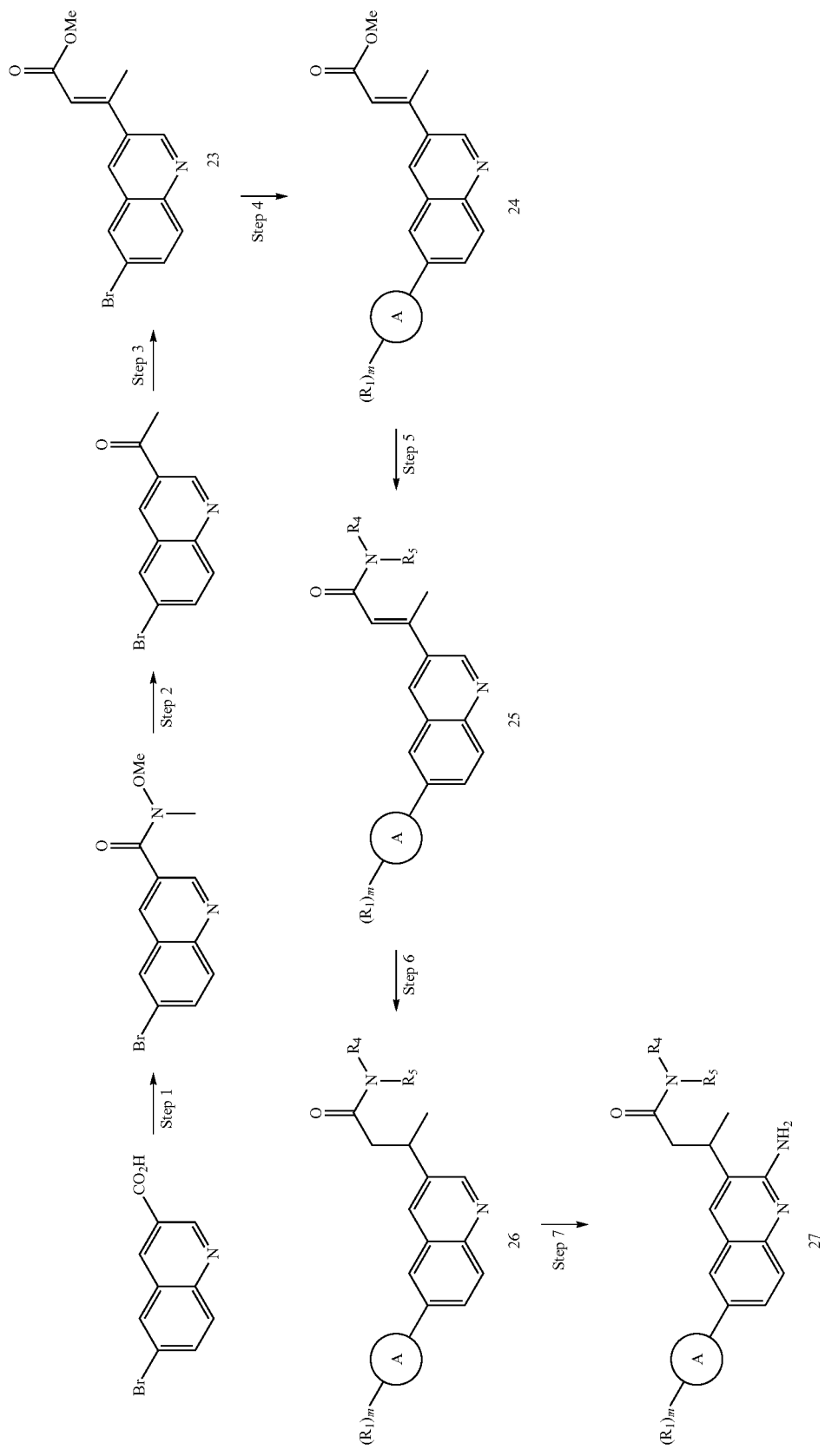

Representative compounds 27, wherein R² is methyl, of formulas I, I-A and I-B may be prepared by the method illustrated in scheme VI and described step-by-step below.

Step 1

To a 500 mL RBF containing 6-bromoquinoline-3-carboxylic acid (1.0 g, 4.0 mmol) was added THF (15 mL) and the mixture was allowed to stir at 23° C. for 2 min. At this time, 4-methylmorpholine (1.3 ml, 12 mmol) and 2-chloro-4,6-dimethoxy-1,3,5-triazine (1.0 g, 6.0 mmol) were added in single portions. The reaction was allowed to stir for 1 h and then N,O-dimethylhydroxylamine HCl (0.43 g, 4.4 mmol) was added in one portion. The reaction was allowed to stir overnight and the diluted with water. It was extracted with EtOAc (3×). The combined organics were washed with sodium carbonate (3× 10%), ammonium chloride (2× sat.), sodium bicarbonate and brine. It was dried with magnesium sulfate, filtered and concentrated to give an off white solid. The reaction was repeated on a 3.0 g scale of 6-bromoquinoline-3-carboxylic acid. The combined yield material was purified by column chromatography on a 120 g Isco column (eluting with 30 to 60% EtOAc in hexanes) to give 6-bromo-N-methoxy-N-methylquinoline-3-carboxamide Step 2

To a 500 mL RBF containing 6-bromo-N-methoxy-N-methylquinoline-3-carboxamide (4.00 g, 13.6 mmol) was added THF (50 mL) and the mixture was allowed to stir at 0° C. for 5 min. At this time, methyl magnesium bromide (3 M in ether) (4.5 mL, 13.6 mmol) was added in a fast dropwise manner. After 1 h the material was quenched with the addition sodium bicarbonate (sat 100 mL) and extracted with EtOAc (3×100 mL). The combined organics were washed with brine, dried with sodium sulfate, filtered, concentrated and subjected to 80 g Isco column to give 1-(6-bromoquinolin-3-yl)ethanone as a white solid.

Step 3

1-(6-bromoquinolin-3-yl)ethanone (170 mg, 680 μmol) was placed in a microwave tube and toluene (2 mL) was added before the addition of methyl(triphenylphosphoranylidene)acetate (227 mg, 680 μmol) in one portion. The tube was irradiated in the microwave at 140° C. for 10 min. An additional portion of (triphenylphosphoranylidene)acetate (80 mg) was added to the tube and it was then irradiated in the microwave at 160° C. for 60 min. The crude reaction material was loaded directly to a 40 g Isco column and purified to give methyl 3-(6-bromoquinolin-3-yl)but-2-enoate (representative compound 23) as a mixture of E and Z isomers.

Step 4

A microwave tube (25 mL) was charged with 1,4-dioxane (4 mL) and methyl 3-(6-bromoquinolin-3-yl)but-2-enoate (320 mg, 1045 μmol). O-tolylboronic acid (242 mg, 1777 μmol) was added to the tube followed by sodium carbonate (1045 μl, 2090 μmol) and tetrakis(triphenylphosphine)palladium(0) (60 mg). The tube was irradiated in a microwave at 90° C. for 20 min. The crude mixture was diluted with sodium bicarbonate (75 mL, sat) and extracted with EtOAc (3×30 mL). The combined organics were washed with brine, dried with sodium sulfate, filtered and concentrated to give methyl 3-(6-o-tolylquinolin-3-yl)but-2-enoate (representative compound 24) as a yellow oil. The material was taken directly to the next reaction.

Step 5

To a 500 mL RBF containing methyl 3-(6-o-tolylquinolin-3-yl)but-2-enoate (325 mg, 1024 μmol) was added THF (6 mL) and water (2 mL) the mixture was allowed to stir at 23° C. for 2 min. At this time, LiOH (245 mg, 10240 μmol) and the reaction was allowed to stir for 48 h. The material was poured into EtOAc (50 mL) and HCl (0.5 M, 100 mL) was added to the flask. The layers were separated and the aqueous layer was extracted with dichloromethane (4×30 ml). The combined organic layers were washed with brine, dried with sodium sulfate, filtered and concentrated to give carboxylic acid (369 mg). The crude acid was dissolved in NMP (4928 μL, 51200 μmol) and DIPEA (715 μL, 4096 μmol) was added before the addition of cyclohexanemethylamine (348 μL, 3072 μmol) and tbtu coupling reagent (493 mg, 1536 μmol). The reaction was allowed to stir for 12 h and then poured into sodium bicarbonate. The aqueous layer was extracted with EtOAc (3×25 mL). The combined organics were washed the brine, dried with sodium sulfate, filtered and purified on a 40 g Isco chromatography column to give (N-(cyclohexylmethyl)-3-(6-o-tolylquinolin-3-yl)but-2-enamide (representative compound 25).

Step 6

A RBF (25 mL) was charged with (cyclohexylmethyl)-3-(6-o-tolylquinolin-3-yl)but-2-enamide (184 mg), MeOH (15 mL) and palladium on carbon (10% by weight, 50 mg). Hydrogen gas was bubbled through the reaction for 15 min and then it was allowed to stir for 2 h under 1.0 atm of hydrogen. The crude mixture was passed though a plug of silica gel under a pad of celite and eluted with EtOAc. The volatiles were removed by rotary evaporation to give N-(cyclohexylmethyl)-3-(6-o-tolylquinolin-3-yl)butanamide (representative compound 26). The material was used directly in the next reaction with no further purification.

Step 7

To a RBF (50 mL) containing N-(cyclohexylmethyl)-3-(6-o-tolylquinolin-3-yl)butanamide (185 mg) was added DCM (15 mL) and the flask was placed on an ice bath. After 10 min, mCPBA (239 mg, 3 eq) was added in one portion, and the reaction was allowed to stir for 30 min and then diluted with DCM (75 mL). The organic layer was washed with sodium bicarbonate (sat, 3×50 mL), brine and dried with sodium sulfate. The dried solution was filtered, concentrated and diluted with 1-(trifluoromethyl)benzene (10 mL). To the RBF containing the N-oxide was added tert-butylamine (338 mg, 10 eq) followed by p-toluenesulfonic anhydride (196 mg, 1.3 eq) portion wise over 3 min. After 5 min, the crude reaction was diluted with DCM (50 ml), washed with NaOH (1N, 2×50 mL), sodium bicarbonate (sat, 1×50 mL), brine, dried with sodium sulfate. The dried solution was filtered and concentrated to give 300 mg crude brown oil. This material was chromatographed on a 40 g Isco column (5 to 35% EtOAc in hexanes) to give 3-(2-(tert-butylamino)-6-o-tolylquinolin-3-yl)-N-(cyclohexylmethyl)butanamide. A portion of this material was treated with TFA (5 mL) at 72° C. for 1 h. The TFA was removed by rotary evaporator and the residue diluted with DCM. The organic layer was washed with NaOH (1N, 50 mL). The aqueous layer was back extracted with DCM, washed with brine, dried with sodium sulfate, filtered and concentrated to give 3-(2-amino-6-o-tolylquinolin-3-yl)-N-(cyclohexylmethyl)butanamide (representative compound 27) of a slightly brown oil. MS (ESI, pos. ion) m/z: 412 (M+1).

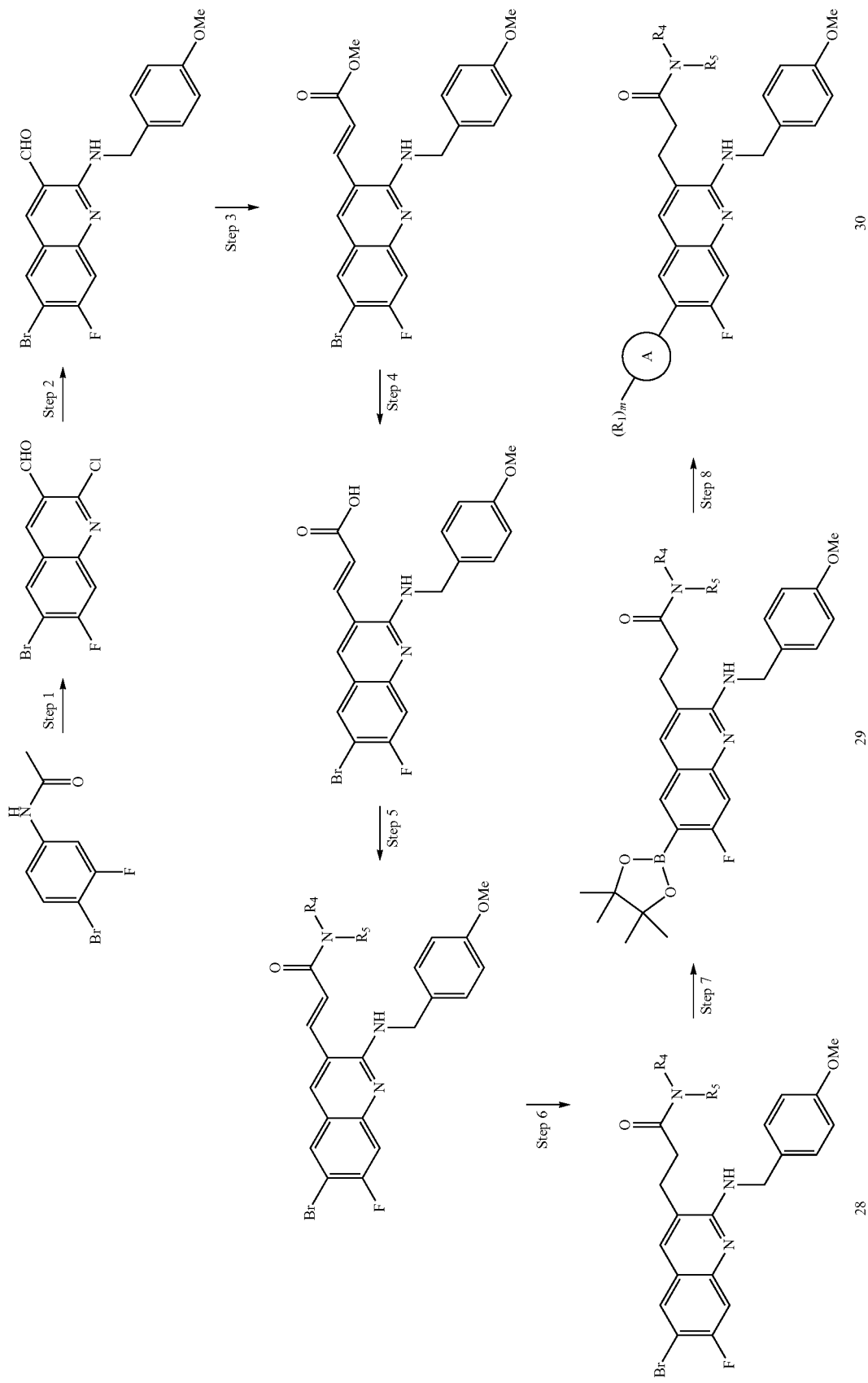

-continued
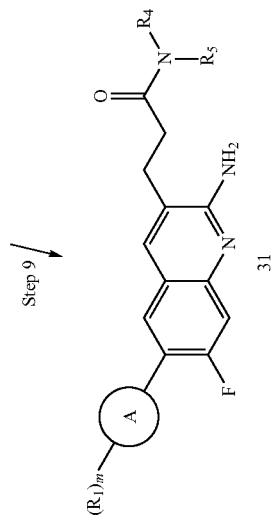

Representative compounds 31, wherein $B^1$ is —CF, of formulas I, I-A and I-B may be prepared by the method illustrated in scheme VII and described step-by-step below.

Step 1

DMF (54 ml, 701 mmol, 2.5 eq.) was added dropwise (via a syringe pump) to phosphoryl trichloride (179 ml, 1962 mmol, 7.0 eq.) in a 350 mL sealed tube in an ice bath under nitrogen. After the addition, the water bath was removed and N-(3-fluoro-4-bromophenyl)acetamide (65 g, 280 mmol) was added in one portion and stirred until a homogenous solution was observed (approx. 30 min.). The reaction vessel was sealed and heated at 75° C. for 48 h. The reaction was allowed to cool and slowly poured onto ice (final volume of 2 L) and stirred for 25 min. The solid was filtered and washed with water until the filtrate was no longer acidic (~3 L) and the product was dried in an oven vacuum overnight at 50° C. to afford a light tan/gold colored solid, 6-bromo-2-chloro-7-fluoroquinoline-3-carbaldehyde.

Step 2

6-Bromo-2-chloro-7-fluoroquinoline-3-carbaldehyde (10.6 g, 37.0 mmol) and 4-methoxybenzylamine (14.4 ml, 110.9 mmol) in EtOH (200 mL) were heated at 125° C. in a sealed tube for 2.5 hours. The reaction mixture was cooled and poured into 1N HCl (200 mL) and stirred 2 h. The mixture was extracted with chloroform and the combined organic layers were washed with 1N HCl and brine, dried over sodium sulfate, filtered and concentrated to afford 6-bromo-7-fluoro-2-(4-methoxybenzylamino)quinoline-3-carbaldehyde.

Step 3

Methyl(triphenylphosphoranylidene)acetate (13.4 g, 40.0 mmol) was added to a solution of 6-bromo-7-fluoro-2-(4-methoxybenzylamino)quinoline-3-carbaldehyde (12.9 g, 33.4 mmol) in THF (200 mL) and the reaction was heated to 70° C. for 2.5 h. The reaction was concentrated and dissolved in a minimal amount of DCM and loaded onto a filter plug of silica washed with hexanes. The product was eluted with 4:1 Hex/EtOAc to give (E)-methyl 3-(6-bromo-7-fluoro-2-(4-methoxybenzylamino)quinolin-3-yl)acrylate.

Step 4

A 1M aqueous solution of LiOH (8.9 mL, 8.9 mmol) was added to a solution of (E)-methyl 3-(6-bromo-7-fluoro-2-(4-methoxybenzylamino)quinolin-3-yl)acrylate (3.9 g, 8.9 mmol) in MeOH (9 mL) and THF (30 mL) at RT. The reaction was stirred 45 min before the organics were removed in vacuo and the remaining aqueous solution was brought to a pH ~1 with 1N HCl aq and the solution was extracted with a 2:1 chloroform/i-PrOH mixture. The combined organics were washed with brine, dried over sodium sulfate, filtered, and concentrated to afford the methyl acrylate adduct which was used without further purification.

Step 5

O-(Benzotriazol-1-yl)-N,N,N' N'-tetramethyluronium tetrafluoroborate (0.15 g, 0.47 mmol) was added to a solution of (E)-methyl 3-(6-bromo-7-fluoro-2-(4-methoxybenzylamino)quinolin-3-yl)acrylic acid (0.154 g, 0.36 mmol), cyclohexylmethanamine (0.14 ml, 1.1 mmol), and DIPEA (0.25 mL, 1.5 mmol) in NMP (1.2 mL) and the reaction was stirred 1 h before being poured into a vigorously stirred solution of saturated aqueous sodium bicarbonate. After 30 min, the mixture was diluted with EtOAc. The layers were separated and the aqueous layer was extracted with EtOAc. The combined organic layers were washed with water, brine, dried over sodium sulfate, filtered, and concentrated to afford (E)-3-(6-bromo-7-fluoro-2-(4-methoxybenzylamino)quinolin-3-yl)-N-(cyclohexylmethyl)acrylamide (representative compound 28).

Step 6

Platinum, 5 wt. % on activated carbon, (1.8 g, 9.0 mmol) was added to a degassed solution of (E)-3-(6-bromo-7-fluoro-2-(4-methoxybenzylamino)quinolin-3-yl)-N-(cyclohexylmethyl)acrylamide (4.7 g, 9.0 mmol) in EtOH (100 mL). The flask was degassed with hydrogen gas and then stirred under a balloon of hydrogen 18 h. The reaction was purged with nitrogen and filtered through a pad of celite with ethanol and concentrated. The crude product was purified by silica gel chromatography with 1.5:1 Hexene/EtOAc to afford 3-(6-bromo-7-fluoro-2-(4-methoxybenzylamino)quinolin-3-yl)-N-(cyclohexylmethyl)propanamide.

Step 7

Dichloro 1,1'-bis(diphenylphosphino)ferrocene palladium (0.096 g, 0.12 mmol) was added to a solution of 3-(6-bromo-7-fluoro-2-(4-methoxybenzylamino)quinolin-3-yl)-N-(cyclohexylmethyl)propanamide (1.3 g, 2.4 mmol), potassium acetate (0.69 g, 7.1 mmol), and 4,4,5,5-tetramethyl-2-(4,4,5,5-tetramethyl-1,3,2-dioxaborolan-2-yl)-1,3,2-dioxaborolane (0.72 g, 2.8 mmol) in dioxane (20 mL). The solution was heated at 85° C. for 4 h. The reaction was cooled and concentrated. The crude product was diluted with ethyl acetate and filtered. The filtrate was concentrated to afford N-(cyclohexylmethyl)-3-(7-fluoro-2-(4-methoxybenzylamino)-6-(4,4,5,5-tetramethyl-1,3,2-dioxaborolan-2-yl)quinolin-3-yl)propanamide which was used without further purification.

Step 8

Bis(4-(di-tert-butylphosphino)-N,N-dimethylbenzenamine) dichloropalladium (II) (0.0064 g, 0.0090 mmol) was added to a degassed solution of N-(cyclohexylmethyl)-3-(7-fluoro-2-(4-methoxybenzylamino)-6-(4,4,5,5-tetramethyl-1,3,2-dioxaborolan-2-yl)quinolin-3-yl)propanamide (0.10 g, 0.18 mmol), potassium acetate (0.035 g, 0.36 mmol), and 2-bromotoluene (0.046, 0.27 mmol) in EtOH (1.7 mL) and water (0.30 mL). The reaction was refluxed 5 h until determined to be complete by LC/MS. After cooling, the reaction was partitioned between DCM and a 9:1 saturated aqueous ammonium chloride/ammonium hydroxide solution. The aqueous layer was extracted with DCM and the combined organics were washed with a 9:1 saturated ammonium chloride/ammonium hydroxide solution, water, brine, dried over sodium sulfate, filtered, and concentrated to afford N-(cyclohexylmethyl)-3-(7-fluoro-2-(4-methoxybenzylamino)-6-o-tolylquinolin-3-yl)propanamide.

Step 9

N-(cyclohexylmethyl)-3-(7-fluoro-2-(4-methoxybenzylamino)-6-o-tolylquinolin-3-yl)propanamide (0.070 g, 0.14 mmol) was refluxed in TFA (5.0 mL, 65 mmol) for 3 hours. The reaction was concentrated and the crude material was purified by reversed phase HPLC (10:100, 20 minutes) to afford 3-(2-amino-7-fluoro-6-o-tolylquinolin-3-yl)-N-(cyclohexylmethyl)propanamide with MS (ESI, pos. ion) m/z: 420 (M+1).

Scheme VIII

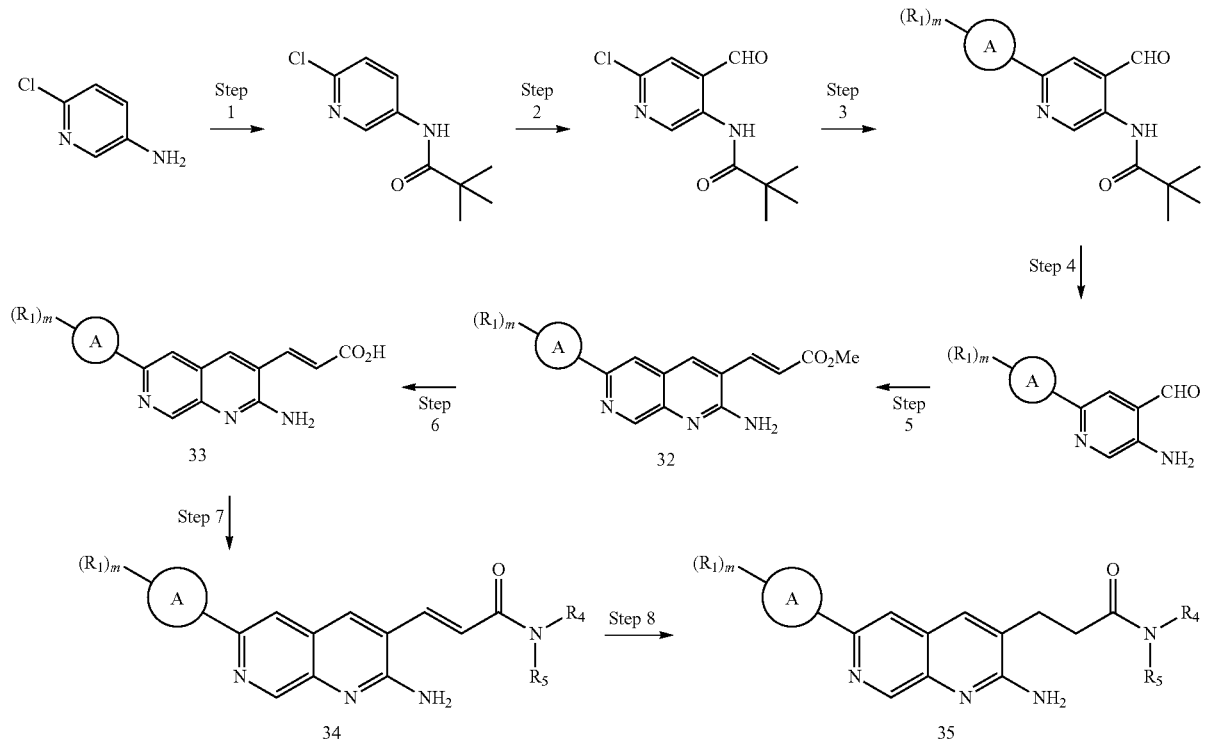

Representative compounds 35, wherein $B^1$ is —N—, of formulas I, I-A and I-B may be prepared by the method illustrated in VIII and described step-by-step below.

Step 1

To a cooled (ice bath) solution of 5-amino-2-chloropyridine (16.20 g, 126.0 mmol) and TEA (21.03 ml, 151.2 mmol) in DCM (100 ml) was added dropwise trimethyl acetyl chloride (15.91 ml, 132.3 mmol) DCM (100 ml). The addition was completed in 1.5 h. The reaction was then stirred at RT for 3 h. 1N NaOH (100 ml) was added to the mixture and the layers were separated. The organic layer was washed with 1N NaOH (100 ml), brine and dried over $Na_2SO_4$. After filtration, the filtrate was concentrated. The residue was dissolved in hot EtOAc and treated with charcoal. The solution was then filtered through celite. The filtrate was concentrated giving a pink solid. The solid was diluted with EtOAc and hexane resulted in the precipitation of the t-butyl amide adduct as light pink crystals. MS m/z: 213 (M+1).

Step 2

To a cooled (−78° C.) solution of N-(6-chloropyridin-3-yl) pivalamide (5.19 g, 24.4 mmol) in THF (100 ml) was added dropwise tert-butyllithium (31.6 ml, 53.7 mmol). The mixture was stirred for 1 h after the addition was completed. DMF (13.2 ml, 171 mmol) was then added and the reaction was stirred for 1 h. Saturated $NH_4Cl$ was added to quench the reaction, and the solution was allowed to warm to RT and the layers were separated. The aqueous layer was extracted with EtOAc. The organic layers were combined, dried over $Na_2SO_4$, filtered and concentrated. The residue was purified on silica gel (120 g) column (20-40% EtOAc/hexane) to afford the aldehyde product as orange color solid. MS m/z: 241 (M+1).

Step 3

A mixture of N-(6-chloro-4-formylpyridin-3-yl)pivalamide (0.475 g, 1.97 mmol), o-tolylboronic acid (0.402 g, 2.96 mmol), potassium acetate (1.36 g, 13.8 mmol) and Pd catalyst (0.0123 g, 0.0197 mmol) in $CH_3CN$ (3.0 ml) and water (1.0 ml) was heated at 100° C. in microwave for 15 min. The solvent was then removed under reduced pressure. The aqueous residue was extracted with EtOAc (2×). The organics were combined, washed with brine, dried over $Na_2SO_4$ and filtered. The filtrate was concentrated and dried in vacuum affording crude N-(4-formyl-6-o-tolylpyridin-3-yl)pivalamide as yellow solid. MS m/z: 297 (M+1). This material was carried forward without further purification.

Step 4

N-(4-formyl-6-o-tolylpyridin-3-yl)pivalamide (0.585 g, 2.0 mmol) and 3N aqueous HCl (5.0 ml, 15 mmol) was heated at 100° C. for 16 h. The resulted suspension was extracted with ethyl ether (2×). The organic layer was discarded. The aqueous suspension was filtered and the solid was found to be the desired product (MS+=204, 407). The solid was suspended in water and neutralized with $K_2CO_3$. The resulted aqueous solution was extracted with EtOAc (3×). The organic layers were combined, concentrated and dried in vacuum to afford 5-amino-2-o-tolylisonicotinaldehyde as yellow solid. MS m/z: 204 ((2M+2-18)/2). This material was carried on without further purification.

Step 5

To a solution of 2-amino-6-o-tolyl-1,7-naphthyridine-3-carbaldehyde (0.105 g, 0.399 mmol) in DMSO was added methyl(triphenylphosphoranylidene)acetate (0.147 g, 0.439 mmol) followed by potassium carbonate (0.0289 ml, 0.479 mmol). The mixture was heated at 70° C. and the conversion was completed in 2 h. EtOAc and water was added and the layers were separated. The organic layer was concentrated and purified by Shimadzu HPLC to afford methyl 3-(2-amino-6-o-tolyl-1,7-naphthyridin-3-yl)acrylate (32) as yellow oil. It was contaminated by methyl(triphenylphosphoranylidene)acetate (MS+=335) as they had same retention time on HPLC. MS m/z: 320 (M+1).

Step 6

Methyl 3-(2-amino-6-o-tolyl-1,7-naphthyridin-3-yl)acrylate (0.050 g, 0.16 mmol) in MeOH (5.0 ml) was treated with NaOH (0.60 ml, 3.0 mmol). The conversion was completed after stirred for 2 h at RT. Water (2.0 ml) was added, and then MeOH was removed under reduced pressure. The aqueous was neutralized with 2 N HCl and then filtered. The solid was dried in air and identified as the desired product (33). The filtrate was extracted with EtOAc (3x). The organic layers were combined, concentrated and dried in vacuum to afford additional product. The product was a light yellow solid. MS m/z: 306 (M+1).

Step 7

To a solution of 3-(2-amino-6-o-tolyl-1,7-naphthyridin-3-yl) acrylic acid (0.028 g, 0.092 mmol) in NMP (1.0 ml) was added N-ethyl-N-isopropylpropan-2-amine (0.064 ml, 0.37 mmol) followed by tbtu (0.038 g, 0.12 mmol). After stirred for 5 min, 3,3-dimethylbutan-1-amine (0.028 g, 0.28 mmol) was added. The stirring was continued for 1 h until the starting material was consumed. Saturated NaHCO$_3$ was added into the reaction mixture and the resulting precipitate 34 (solid) was filtered and dried to afford the desired product 34 as yellow solid. MS m/z: 389 (M+1).

Step 8

A mixture of 3-(2-amino-6-o-tolyl-1,7-naphthyridin-3-yl)-N-(3,3-dimethylbutyl)acrylamide and palladium on activated carbon, 10% Pd (0.011 g, 0.1 mmol) in EtOH (4.0 ml) was stirred under H2 balloon and monitored By LCMS. After stirred for 4 h, the conversion was completed. The resulted suspension was filtered through celite and eluted with EtOAc. The filtrate was concentrated and dried in vacuum giving the title compound 35 as off-white solid. MS m/z: 391 (M+1).

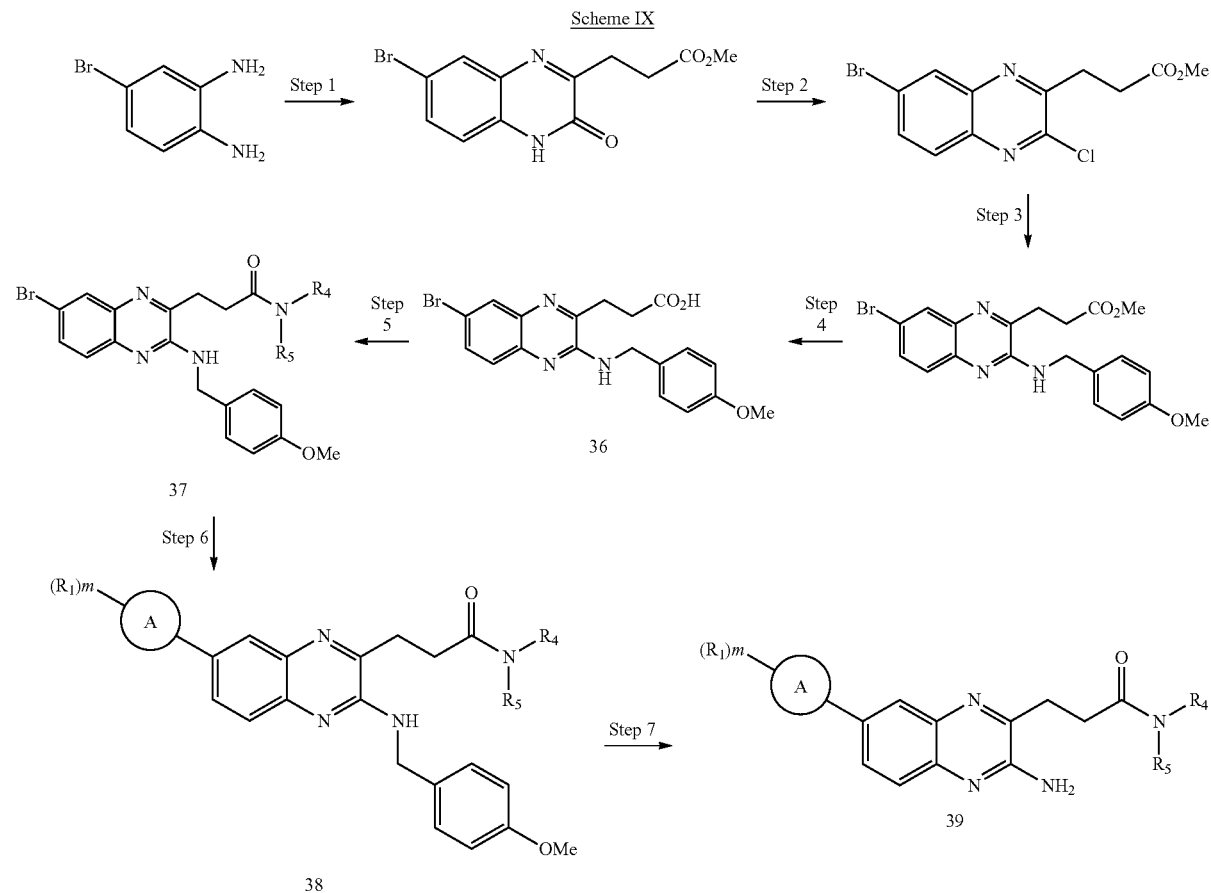

Representative compounds 35, wherein B$^3$ is —N—, of formulas I, I-A and I-B may be prepared by the method illustrated in scheme IX and described step-by-step below.

Step 1

To a 25 ml microwave synthesizer vial containing 4-bromobenzene-1,2-diamine (2.30 g, 12.3 mmol) in 15 ml of MeOH was added dimethyl 2-oxopentanedioate (2.14 g, 12.3 mmol). The mixture was heated in the microwave synthesizer at 140° C. for 12 min. Red precipitate formed, which was filtered, and washed successively with 10 ml of MeOH (1x), 10 ml of DCM (1x), and 15 ml of hexanes (2x) to give methyl 3-(7-bromo-3-oxo-3,4-dihydroquinoxalin-2-yl)propanoate as a light purple solid after drying. M+H+: 312.

Step 2

Methyl 3-(7-bromo-3-chloroquinoxalin-2-yl)propanoate from Step 1 (0.65 g, 1 mmol) was treated with phosphoryl trichloride (4 ml, 44 mmol) at about 102° C. for 1.5 h. An initial suspension became a black solution. The solution was cooled and pipetted over to 50 g of crushed ice. After the ice melted, 35 ml of DCM was added, and the reaction mixture was vigorously mixed and then the layers were separated. The DCM layer was dried (Na₂SO₄) and concentrated to give methyl 3-(7-bromo-3-chloroquinoxalin-2-yl)propanoate as an oil. M+H+: 329, 331.

Step 3
A solution of N-ethyl-N-isopropylpropan-2-amine (523 µl, 3004 µmol), (4-methoxyphenyl)methanamine (302 mg, 2203 µmol) and 3-(7-bromo-3-chloroquinoxalin-2-yl)propanoate (660 mg) in 10 ml of DMF was stirred at rt for 48 h. TLC showed incomplete reaction (~60% conversion). (4-Methoxyphenyl)methanamine (302 mg, 2203 µmol) was added and the solution was transferred to a microwave vial and heated at 100° C. for 10 min. The reaction was diluted with EtOAc 30 ml, washed with 30 ml of H₂O, and the aqueous layer was extracted with 20 ml of EtOAc. The organic layers were combined, washed with again with 2×30 ml of H₂O, dried (Na₂SO₄), and concentrated to give methyl 3-(7-bromo-3-(4-methoxybenzylamino)quinoxalin-2-yl)propanoate as an oil that was moved onto the next step without any further purification. M+H+: 430, 432.

Step 4
3-(7-Bromo-3-(4-methoxybenzylamino)quinoxalin-2-yl)propanoate from was dissolved in 5 ml of THF and 5 mL of MeOH. 10 ml of 1N NaOH solution was added and the resulting mixture was heated in a microwave synthesizer for 15 min at 110° C. Organic solvents were removed and the aqeuous solution was then treated with 30 ml of NaH₂PO₄ solution (10%) and extracted with 3×30 ml of DCM. The organic layers were combined, then dried (Na₂SO₄) and concentrated to give 3-(7-bromo-3-(4-methoxybenzylamino)quinoxalin-2-yl)propanoic acid (36) a brown solid.

Step 5
A solution of 3-(7-bromo-3-(4-methoxybenzylamino)quinoxalin-2-yl)propanoic acid (730 mg, 877 µmol), N-ethyl-N-isopropylpropan-2-amine (458 µl, 2631 µmol) and cyclohexylmethanamine (208 mg, 1841 µmol) in 10 ml of DCM was treated with HATU (733 mg, 1929 µmol) at rt for 30 min. The reaction was diluted with 30 ml of DCM, washed with 2×30 ml of H₂O, 1×30 ml of 1N NaOH, dried (Na₂SO₄) and concentrated to give a residue which was purified by ISCO using 0-30% EtOAc in hexanes. Desired fractions were concentrated to give 3-(7-bromo-3-(4-methoxybenzylamino)quinoxalin-2-yl)-N-(cyclohexylmethyl)propanamide 37. M+H+: 511, 513.

Step 6
To a microwave vial containing potassium acetate (154 mg, 1564 µmol), o-tolylboronic acid (133 mg, 978 µmol), and 3-(7-bromo-3-(4-methoxybenzylamino)quinoxalin-2-yl)-N-(cyclohexylmethyl)propanamide from Step 5 (400 mg, 391 µmol) in 3 ml of EtOH and 1 ml of H2O was added PdCl₂ (AmPhos)₂ (8.31 mg, 11.7 µmol) and the mixture was heated at 120° C. for 15 min. The mixture was then concentrated and diluted with 20 ml of EtOAc and washed with sat. NaHCO₃ (2×20 ml). The organic layer was then dried (Na₂SO₄) and concentrated to give compound 38 as an oil. M+H+: 523.

Step 7
The crude 3-(7-bromo-3-(4-methoxybenzylamino)quinoxalin-2-yl)-N-(cyclohexylmethyl)propanamide was dissolved in 3 ml of TFA and was transferred to a microwave vial and heated at 100° C. for 10 min. The excess TFA was removed under vacuum. The residue was partitioned between DCM and 1N NaOH. The DCM layer was separated and concentrated to give an oil, which was taken into a DMF solution (5 mL) and was purified by HPLC. The desired fractions were combined and basicified with 1N NaOH, extracted with 3×40 ml of DCM. The combined DCM layers were dried (Na₂SO₄) and concentrated. The residue was then further purified by prep TLC using 4% MeOH in DCM. The desired bands were eluted with 4% MeOH in DCM and vacuum dried to give 3-(3-amino-7-o-tolylquinoxalin-2-yl)-N-(cyclohexylmethyl)propanamide 39 as a white solid. M+H+: 403.

Scheme X

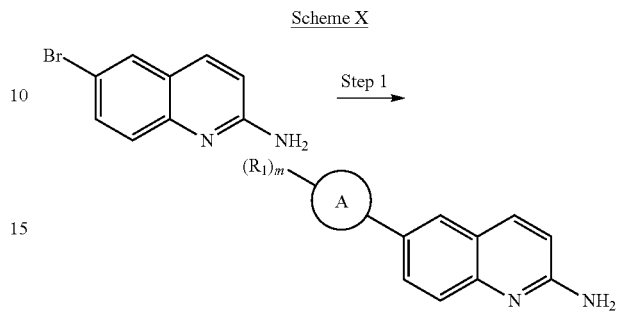

Representative compounds wherein ring A comprising desired R¹ groups, of formulas I, I-A and I-B, may be prepared by the method illustrated in scheme X and described below.

Step 1
A mixture of 1H-indol-6-ylboronic acid (43 mg, 0.27 mmol), 6-bromoquinolin-2-amine (40 mg, 0.22 mmol), K₂CO₃ (3M, 100 uL), PS—PPh₃-Pd (20 mg, 0.11 mmol/g), and DME/EtOH (50%, 1 mL) was heated in a microwave at 140° C. for 10 min. The resulting slurry was filtered and purified by HPLC (10-60% CH₃CN/water modified with 0.1% TFA) to give 6-(1H-indol-6-yl)quinolin-2-amine (31 mg). MS (ESI, pos. ion) m/z: 260 (M+1).

Scheme XI

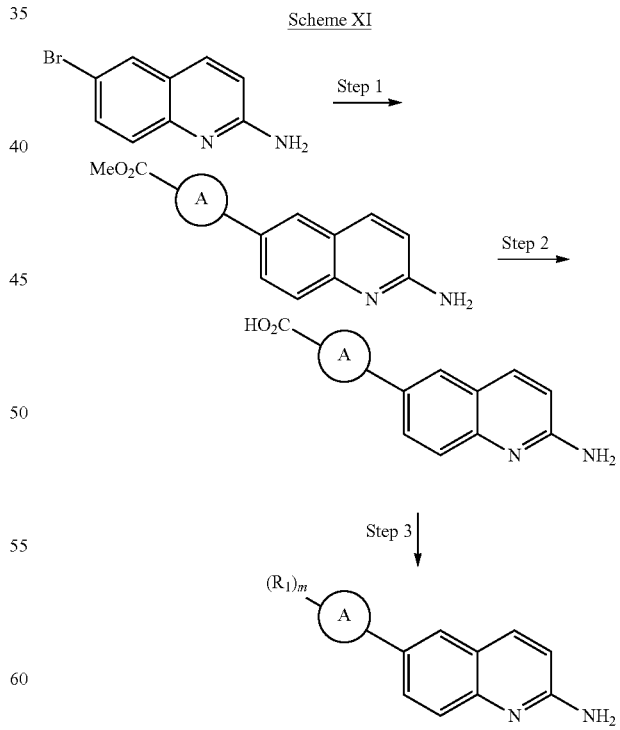

Alternatively, representative compounds wherein ring A comprising desired R¹ groups, of formulas I, I-A and I-B, may be prepared by the method illustrated in scheme XI and described below.

Step 1
To a microwave reaction vessel was added ethyl-2-(4,4,5,5-tetramethyl-1,3,2-dioxaborolan-2-yl)benzoate (3.7 g, 13 mmol), 6-bromoquinolin-2-amine (2.0 g, 9.0 mmol), PdCl$_2$(PPh(t-Bu)$_2$)$_2$ (0.084 g, 0.13 mmol), potassium acetate (1.8 g, 18 mmol), EtOH (9.9 ml, 170 mmol) and water (2.4 ml, 134 mmol). The reaction mixture was heated at 85° C. for 8 h, and was then partitioned between EtOAc and water. The organic layer was washed with water and brine and allowed to stand for 72 h. The supernatant was decanted from the resulting precipitate and the precipitate was dried in vacuo to give ethyl 2-(2-aminoquinolin-6-yl)benzoate.
Step 2
6-(2-Ethoxyphenyl)quinolin-2-amine (1.0 g, 3.8 mmol) was taken up in THF and then 5N NaOH was added and the solution was stirred for 72 h. DCM was added and the solid was filtered to give ethyl 2-(2-aminoquinolin-6-yl)benzoate.
Step 3
A solution of 2-(2-aminoquinolin-6-yl)benzoic acid (50 mg, 0.19 mmol), 4-fluoropiperidine (25 mg, 0.24 mmol), HATU (91 mg, 0.24 mmol), DIEA (100 uL, 0.57 mmol), and DMF (1 mL) was heated in a shaker oven at 60° C. for 1 h. The resulting solution was purified by HPLC (CH$_3$CN/water modified with 0.1% TFA) to give (2-(2-aminoquinolin-6-yl)phenyl)(4-fluoropiperidin-1-yl)methanone. MS (ESI, pos. ion) m/z: 350 (M+1).

Product compounds from schemes X and XI may be used as intermediates to install functionality of L$^1$-amido-R groups via conventional or methods known in the art, or a method similar to step 2 of scheme VIII.

To enhance the understanding and appreciation of the present invention, the following specific examples (starting reagents, intermediates and compounds of Formulas I, I-A and I-B) are set forth. The following analytical methods were used to purify and/or characterize the compounds, and intermediates, described in the examples below.

Chromatography:
Unless otherwise indicated, crude product-containing residues were purified by passing the crude material or concentrate through an ISCO brand silica gel column (pre-packed or individually packed with SiO$_2$) and eluting the product off the column with a solvent gradient as indicated. For example a description of (330 g SiO$_2$, 0-40% EtOAc/Hexane) means the product was obtained by elution from the column packed with 330 gms of silica, with a solvent gradient of 0% to 40% EtOAc in Hexanes.

Chiral Separation:
Unless otherwise indicated, the racemic compounds described herein were separated or purified via preparative Supercritical Fluid Chromatography (SFC), which typically involved using about 12% isopropanol with about 0.2% diethylamine in supercritical carbon dioxide. Such separation provided peak fractions which, upon collection and additional characterization (NMR, MS, X-ray diffraction, etc.), corresponding to pure S and R diasteromers.

Proton NMR Spectra:
Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)
Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument instrument or an Agilent 1100 series LC/MSD system. Compounds having an isotopic atom, such as bromine and the like, are generally reported according to the detected isotopic pattern, as appreciated by those skilled in the art.

EXAMPLES

The Examples, described herein below, represent various exemplary starting materials, intermediates and compounds of Formulas I, I-A and I-B, which should assist in a better understanding and appreciation of the scope of the present invention and of the various methods which may be used to synthesize compounds of Formulas I, I-A and I-B. It should be appreciated that the general methods above and specific examples below are illustrative only, for the purpose of assistance and of understanding the present invention, and should not be construed as limiting the scope of the present invention in any manner. The exemplary compounds disclosed herein have been named using either (1) the naming convention provided with Chem-Draw Ultra 8.0 software, available in Chem Office, or (2) by the ISIS database software (Advanced Chemistry Design Labs or ACD software).

Example 1

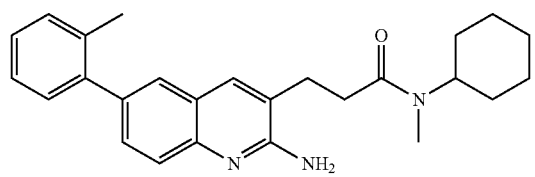 [SMILES: Cc1ccccc1-c1ccc2nc(N)c(CCC(=O)N(C)C3CCCCC3)cc2c1]

Synthesis of 3-(2-amino-6-o-tolylquinolin-3-yl)-N-cyclohexyl-N-methylpropanamide Step 1
5-Bromo-2-nitrobenzaldehyde (6.03 g, 26.2 mmol) was dissolved in MeOH (200 mL) and treated with 5N HCl (10 mL). The mixture was heated to 70° C. and iron powder (7.32 g, 131 mmol) was added in five portions every 5 min. The reaction was monitored by TLC, and upon completion, the reaction was cooled, DCM (200 mL) added and filtered through a pad of celite. The filtrate was concentrated under reduced pressure to about 150 mL. To this material, a solution of 1,1,3,3-tetramethoxypropane (9.52 ml, 57.7 mmol) in 5N HCl (10 mL) pre-mixed for 45 min was added. The reaction mixture was stirred at 80° C. for 60 min. Toluene (100 mL) and HOAc (40 mL) were added and the solution was heated to 110° C. for 3 h, then cooled and evaporated to dryness under reduced pressure. The crude material was purified using silica chromatography (20-60% ethyl acetate in hexane gradient) to provide 6-bromoquinoline-3-carbaldehyde.
Step 2
6-Bromoquinoline-3-carbaldehyde (2.8 g, 12.0 mmol) and methyl(triphenylphosphoranylidene)acetate (4.0 g, 12.0 mmol) were dissolved in dry THF (50 mL) and heated to 50° C. After 40 min the solution was evaporated to dryness under reduced pressure. Purification using silica chromatography (hexane to 60% EtOAc in hexane gradient) gave methyl 3-(6-bromoquinolin-3-yl)acrylate as a mixture of E and Z isomers.

Step 3

Methyl 3-(6-bromoquinolin-3-yl)acrylate (0.91 g, 3.1 mmol) 2-methylphenyl boronic acid (0.61 g), potassium acetate (1.0 g) and bis(4-(di-tert-butylphosphino)-N,N-dimethylbenzenamine)dichloropalladium (II) (0.19 g) were suspended in ethanol (70 mL) and water (5 mL) and heated to reflux for 90 min. LC/MS showed the bromoquinoline had been consumed the reaction was evaporated to dryness under reduced pressure. The crude was partitioned between EtOAc and water. The organic layer was dried with magnesium sulfate, evaporated to dryness under reduced pressure and purified using silica chromatography (hexane to EtOAc gradient) to give methyl 3-(6-o-tolylquinolin-3-yl)acrylate.

Step 4

LiOH monohydrate (0.42 g) (solution in water, 10 mL) was added to a solution of methyl 3-(6-o-tolylquinolin-3-yl)acrylate (0.32 g, 1.05 mmol) in MeOH (50 mL) and heated to 50° C. The reaction was monitored by TLC and once the ester had been consumed, 5N HCl (2 mL) was added and the mixture was concentrated to dryness under reduced pressure. The crude acid was dried under high vacuum then dissolved in thionyl chloride (30 mL) and heated to 80° C. for 1 h. The solution was evaporated to dryness under reduced pressure and the crude acid chloride dissolved in DCM (50 mL). A solution of N-methylcyclohexylamine (660 uL) and DIEA (850 uL) in DCM (10 mL) was added slowly and the mixture stirred for 15 min. Additional DCM (50 mL) and water (80 mL) were added and the phases were separated. The organic layer was dried with magnesium sulfate and evaporated to dryness under reduced pressure. Purification using silica chromatography (hexane to EtOAc gradient) gave the desired amide. This material was dissolved in MeOH (50 mL) and treated with 10 wt % palladium on carbon (0.12 g). The mixture was hydrogenated at 50 psi for 30 min until the reduction was complete by LC/MS. The mixture was filtered through a pad of celite and evaporated to dryness under reduced pressure. Purification using silica chromatography (hexane to EtOAc gradient) provided N-cyclohexyl-N-methyl-3-(6-o-tolylquinolin-3-yl)propanamide.

Step 5

N-Cyclohexyl-N-methyl-3-(6-o-tolylquinolin-3-yl)propanamide (0.13 g) and m-chloroperbenzoic acid (0.11 g) were dissolved in chloroform and heated to reflux for 10 min. DCM (30 mL) and 1N NaOH (70 mL) were added and the phases mixed and separated. The organic layer was dried with magnesium sulfate and evaporated to dryness under reduced pressure. The crude N-oxide was dissolved in a mixture of trifluoromethylbenzene (20 mL) and tert-butylamine (0.20 mL), then p-toluenesulfonic anhydride (0.15 g) was added. The mixture was stirred until LC/MS analysis showed the desired amine had formed. Water (100 mL), 5N NaOH (30 mL), and DCM (70 mL) were added and the phases were separated. The organic layer was dried with magnesium sulfate before evaporating to dryness. Purification using silica chromatography (hexane to EtOAc gradient) gave the 2-(tert-butylamino)-quinoline. This material was dissolved in TFA (30 mL) and heated to reflux. After the deprotection was complete by LC/MS, the solution was evaporated to dryness under reduced pressure and the crude material was basified using saturated sodium bicarbonate and DCM. Silica purification (0-10% MeOH in DCM gradient) gave 3-(2-amino-6-o-tolylquinolin-3-yl)-N-cyclohexyl-N-methylpropanamide. MS (ESI, pos. ion) m/z: 402 (M+1).

Example 2

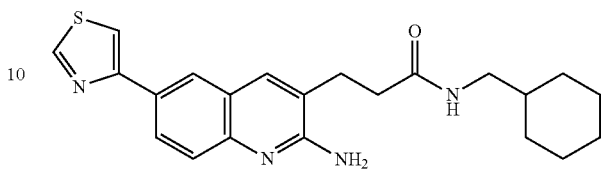

Synthesis of 3-(2-amino-6-(thiazol-4-yl)quinolin-3-yl)N(cyclohexylmethyl)propanamide Step 1

DMF (54 ml, 701 mmol, 2.5 eq.) was added dropwise (via a syringe pump) to phosphoryl trichloride (179 ml, 1962 mmol, 7.0 eq.) in a 350 mL sealed tube in an ice bath under nitrogen. After the addition, the water bath was removed and N-(4-bromophenyl)acetamide (60 g, 280 mmol) was added in one portion and the mixture was stirred until a homogenous solution was observed (approx. 30 min.). The reaction vessel was sealed and heated at 75° C. for 48 h. The reaction was allowed to cool and slowly poured onto ice (final volume of 2 L) and stirred for 25 min. The solid was filtered and washed with water until the filtrate was no longer acidic (~3 L) and the product was dried in an oven vacuum overnight at 50° C. to afford a light tan/gold colored solid, 6-bromo-2-chloroquinoline-3-carbaldehyde.

Step 2

6-Bromo-2-chloroquinoline-3-carbaldehyde (10.0 g, 37.0 mmol) and 4-methoxybenzylamine (14.4 ml, 110.9 mmol) in EtOH (200 mL) was heated at 125° C. in a sealed tube for 2.5 hours. The reaction mixture was cooled and poured into 1N HCl (200 mL) and stirred 2 h. The mixture was extracted with chloroform and the combined organic layers was washed with 1N HCl and brine, dried over sodium sulfate, filtered and concentrated to afford 2-(4-methoxybenzylamino)-6-bromoquinoline-3-carbaldehyde.

Step 3

Methyl(triphenylphosphoranylidene)acetate (13.4 g, 40.0 mmol) was added to a solution of 2-(4-methoxybenzylamino)-6-bromoquinoline-3-carbaldehyde (12.4 g, 33.4 mmol) in THF (200 mL) and the reaction was heated to 70° C. for 2.5 h. The reaction was concentrated and dissolved in a minimal amount of DCM and loaded onto a filter plug of silica washed with hexanes. The product was eluted with 4:1 Hex/EtOAc to give (E)-methyl 3-(2-(4-methoxybenzylamino)-6-bromoquinolin-3-yl)acrylate.

Step 4

A 1M aqueous solution of LiOH (8.9 mL, 8.9 mmol) was added to a solution of (E)-methyl 3-(2-(4-methoxybenzylamino)-6-bromoquinolin-3-yl)acrylate (3.8 g, 8.9 mmol) in MeOH (9 mL) and THF (30 mL) at RT. The reaction was stirred 45 min before the organics were removed in vacuo and the remaining aqueous solution was brought to a pH ~1 with 1N HCl aq and the solution was extracted with a 2:1 chloroform/i-PrOH mixture. The combined organics were washed with brine, dried over sodium sulfate, filtered, and concentrated to afford the desired compound which was used without further purification.

Step 5

O-(Benzotriazol-1-yl)-N,N,N',N'-tetramethyluronium tetrafluoroborate (0.15 g, 0.47 mmol) was added to a solution of (E)-3-(2-(4-methoxybenzylamino)-6-bromoquinolin-3-yl)acrylic acid (0.15 g, 0.36 mmol), cyclohexylmethanamine (0.14 ml, 1.1 mmol), and DIEA (0.25 mL, 1.5 mmol) in NMP (1.2 mL) and the reaction was stirred 1 h before being poured into a vigorously stirred solution of saturated aqueous sodium bicarbonate. After 30 min, the mixture was diluted with EtOAc. The layers were separated and the aqueous layer was extracted with EtOAc. The combined organic layers were washed with water, brine, dried over sodium sulfate, filtered, and concentrated to afford (E)-3-(2-(4-methoxybenzylamino)-6-bromoquinolin-3-yl)-N-(cyclohexylmethyl)acrylamide.

Step 6

Platinum, 5 wt. % on activated carbon, (1.8 g, 9.0 mmol) was added to a degassed solution of (E)-3-(2-(4-methoxybenzylamino)-6-bromoquinolin-3-yl)-N-(cyclohexylmethyl)acrylamide (4.6 g, 9.0 mmol) in EtOH (100 mL). The flask was degassed with hydrogen gas and then stirred under a balloon of hydrogen gas for 18 h. The reaction was purged with nitrogen and filtered through a pad of celite with EtOH and concentrated. The crude product was purified by silica gel chromatography with 1.5:1 Hexene/EtOAc to afford 3-(2-(4-methoxybenzylamino)-6-bromoquinolin-3-yl)-N-(cyclohexylmethyl)propanamide.

Step 7

Dichloro 1,1'-bis(diphenylphosphino)ferrocene palladium (0.096 g, 0.12 mmol) was added to a solution of (E)-3-(2-(4-methoxybenzylamino)-6-bromoquinolin-3-yl)-N-(3,3-dimethylbutyl)-2-methylacrylamide (1.2 g, 2.4 mmol), potassium acetate (0.69 g, 7.1 mmol), and 4,4,5,5-tetramethyl-2-(4,4,5,5-tetramethyl-1,3,2-dioxaborolan-2-yl)-1,3,2-dioxaborolane (0.72 g, 2.8 mmol) in dioxane (20 mL). The solution was heated at 85° C. for 4 h. The reaction was cooled and concentrated. The crude product was diluted with ethyl acetate and filtered. The filtrate was concentrated to afford 3-(2-(4-methoxybenzylamino)-6-(4,4,5,5-tetramethyl-1,3,2-dioxaborolan-2-yl)quinolin-3-yl)-N-(cyclohexylmethyl)propanamide, which was used without further purification.

Step 8

Bis(4-(di-tert-butylphosphino)-N,N-dimethylbenzenamine)dichloropalladium (II) (0.0064 g, 0.0090 mmol) was added to a degassed solution of 3-(2-(4-methoxybenzylamino)-6-(4,4,5,5-tetramethyl-1,3,2-dioxaborolan-2-yl)quinolin-3-yl)-N-(cyclohexylmethyl)propanamide (0.10 g, 0.18 mmol), potassium acetate (0.035 g, 0.36 mmol), and 4-bromothiazole (0.024 mL, 0.27 mmol) in EtOH (1.7 mL) and water (0.30 mL). The reaction was refluxed 5 h until determined to be complete by LC/MS. After cooling, the reaction was partitioned between DCM and a 9:1 saturated aqueous ammonium chloride/ammonium hydroxide solution. The aqueous layer was extracted with DCM and the combined organics were washed with a 9:1 saturated ammonium chloride/ammonium hydroxide solution, water, brine, dried over sodium sulfate, filtered, and concentrated to afford 3-(2-amino-6-(thiazol-4-yl)quinolin-3-yl)-N-(cyclohexylmethyl)propanamide.

Step 9

3-(2-(4-Methoxybenzylamino)-6-(thiazol-4-yl)quinolin-3-yl)-N-(cyclohexylmethyl)propanamide (0.070 g, 0.14 mmol) was refluxed in TFA (5.0 mL, 65 mmol) for 3 hours. The reaction was concentrated and the crude material was purified by reversed phase HPLC (10:100, 20 minutes) to afford the title compound. MS (ESI, pos. ion) m/z: 395 (M+1).

Example 3

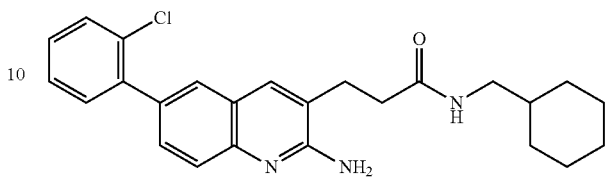

Synthesis of 3-(2-amino-6-(2-chlorophenyl)quinolin-3-yl)-N-(cyclohexylmethyl)propanamide Step 1

To a stirred solution of (E)-3-(2-(4-methoxybenzylamino)-6-bromoquinolin-3-yl)-N-(cyclohexylmethyl)acrylamide (3.7 g, 7.3 mmol, prepared as in Example 2) in DME (100 mL) was added 4-methylbenzenesulfonohydrazide (13.6 g, 72.8 mmol). The mixture was brought to reflux at 86° C. and then via addition funnel was added dropwise a solution of sodium acetate (10.4 g, 127 mmol) in water (60 mL) over 1.5 h. Once the addition was complete, the reaction was refluxed for an additional 30 min, and then cooled to RT and concentrated to remove organic solvent. The crude material was dissolved in DCM (150 mL) and washed sequentially with 1N NaOH, 1N HCl, and then water. The organic layer was dried over MgSO$_4$, filtered and concentrated to give a yellow oil, which upon purification via flash chromatography (5% EtOAc/DCM) afforded 3-(2-(4-methoxybenzylamino)-6-bromoquinolin-3-yl)-N-(cyclohexylmethyl)propanamide.

Step 2

In a sealed tube was combined 3-(2-(4-methoxybenzylamino)-6-bromoquinolin-3-yl)-N-(cyclohexylmethyl)propanamide (0.16 g, 0.31 mmol), 2-chlorophenylboronic acid (0.074 g, 0.47 mmol), bis(di-tert-butyl(4-dimethylaminophenyl)phosphine)dichloropalladium(II) (0.0044 g, 0.0063 mmol), potassium acetate (0.062 g, 0.63 mmol), ethanol (6.0 ml) and water (0.41 mL). The flask was sealed and heated in an oil bath at 85° C. for 16 h. The reaction mixture was cooled to RT, adsorbed onto silica and purified by flash chromatography (5% MeOH/DCM) to afford 3-(2-(4-methoxybenzylamino)-6-(2-chlorophenyl)quinolin-3-yl)-N-(cyclohexylmethyl)propanamide.

Step 3

The product of step 2 was carried through the same procedure as described in Step 9, Example 2, to afford 3-(2-amino-6-(2-chlorophenyl)quinolin-3-yl)-N-(cyclohexylmethyl)propanamide. MS (ESI, pos. ion) m/z: 422 (M+1).

Example 4

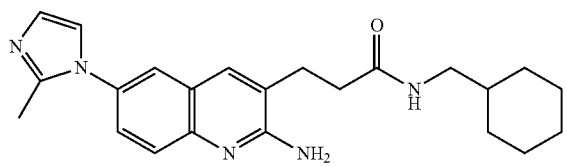 [SMILES: Cc1nccn1-c1ccc2nc(N)c(CCC(=O)NCC3CCCCC3)cc2c1]

Synthesis of 3-(2-amino-6-(2-methyl-1H-imidazol-1-yl)quinolin-3-yl)-N-(cyclohexylmethyl)propanamide Step 1
In a sealed tube was combined 3-(2-(4-methoxybenzylamino)-6-bromoquinolin-3-yl)-N-(cyclohexylmethyl)propanamide (0.32 g, 0.63 mmol, prepared as in Example 3), copper (II) acetate monohydrate (0.025 g, 0.13 mmol), cesium carbonate (0.61 g, 1.9 mmol), hippuric acid (0.016 ml, 0.13 mmol), 2-methyl-/H-imidazole (0.062 g, 0.75 mmol) and DMF (5 mL). The tube was sealed and heated to 140° C. for 48 h. The mixture was cooled to room temperature, transferred to a flask and concentrated to remove the DMF. Adsorbtion onto silica and purification via flash chromatography (slow gradient, 2-10% MeOH/DCM) provided 3-(2-(4-methoxybenzylamino)-6-(2-methyl-1H-imidazol-1-yl)quinolin-3-yl)-N-(cyclohexylmethyl)propanamide.
Step 2
A solution of 3-(2-(4-methoxybenzylamino)-6-(2-methyl-1H-imidazol-1-yl)quinolin-3-yl)-N-(cyclohexylmethyl)propanamide in TFA (10 mL) was heated at 45° C. for 30 min until complete by LC/MS. After concentrating under reduced pressure to remove the TFA, the oil was dissolved in MeOH and purified by reverse phase HPLC to afford 3-(2-amino-6-(2-methyl-1H-imidazol-1-yl)quinolin-3-yl)-N-(cyclohexylmethyl)propanamide. MS (ESI, pos. ion) m/z: 392 (M+1).

Example 5

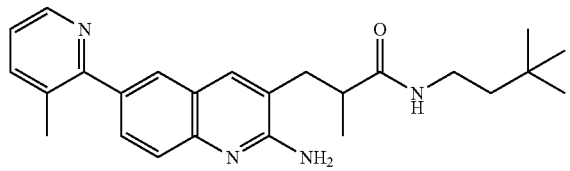 [SMILES: Cc1cccnc1-c1ccc2nc(N)c(CC(C)C(=O)NCCC(C)(C)C)cc2c1]

Synthesis of 3-(2-amino-6-(3-methylpyridin-2-yl)quinolin-3-yl)-N-(3,3-dimethylbutyl)-2-methylpropanamide Step 1
Lithium chloride (2.41 g, 56.7 mmol) is stirred 4 h in MeCN (300 mL). To the cloudy solution was added 2-(4-methoxybenzylamino)-6-bromoquinoline-3-carbaldehyde (10.5 g, 28.4 mmol, prepared as in Example 2), ethyl 2-(diethoxyphosphoryl)propanoate (7.4 L, 34.0 mmol) and 2,3,4,6,7,8,9,10-octahydropyrimido[1,2-a]azepine (4.3 ml, 28.4 mmol) and the reaction is stirred 12 h. The reaction is partitioned between 10% sodium carbonate solution and EtOAc. The aqueous layer is extracted with EtOAc and the combined organic layers are washed with 10% sodium carbonate, brine, dried over sodium sulfate, filtered, and concentrated. The crude mixture is purified by silica gel chromatography eluted with 4:1 Hexanes/EtOAc to afford (E)-ethyl 3-(2-(4-methoxybenzylamino)-6-bromoquinolin-3-yl)-2-methylacrylate.
Step 2
A 1M aqueous solution of LiOH (10.0 ml, 10.0 mmol) was added to a solution of (E)-ethyl 3-(2-(4-methoxybenzylamino)-6-bromoquinolin-3-yl)-2-methylacrylate (3.6 g, 7.9 mmol) in MeOH (10 mL) and THF (30 mL) at RT. The reaction was stirred 1 h. The organic solvent was removed in vacuo and the remaining aqueous solution was brought to a pH ~1 with 1N HCl and the solution was extracted with a 2:1 chloroform/i-PrOH mixture. The combined organics were washed with brine, dried over sodium sulfate, filtered, and concentrated to afford (E)-3-(2-(4-methoxybenzylamino)-6-bromoquinolin-3-yl)-2-methylacrylic acid, which was used without further purification.
Step 3
TBTU (1.2 g, 3.7 mmol) was added to (E)-3-(2-(4-methoxybenzylamino)-6-bromoquinolin-3-yl)-2-methylacrylic acid (1.2 g, 2.8 mmol), 3,3-dimethylbutylamine (1.1 ml, 8.4 mmol), and DIEA (2.0 ml, 11 mmol) in NMP (10 mL) and the reaction was stirred 1 h. The reaction was poured into a vigorously stirred solution of saturated aqueous sodium bicarbonate and after 30 min was diluted with ethyl acetate. The layers were separated and the aqueous layer was extracted with EtOAc. The combined organics were washed with water, brine, and dried over sodium sulfate, filtered, and concentrated to afford (E)-3-(2-(4-methoxybenzylamino)-6-bromoquinolin-3-yl)-N-(3,3-dimethylbutyl)-2-methylacrylamide which was used without further purification.
Step 4
(E)-3-(2-(4-methoxybenzylamino)-6-(4,4,5,5-tetramethyl-1,3,2-dioxaborolan-2-yl)quinolin-3-yl)-N-(3,3-dimethylbutyl)-2-methylacrylamide was prepared in a manner similar to that described in Step 7 of Example 2.
Step 5
Bis(4-(di-tert-butylphosphino)-N,N-dimethylbenzenamine) dichloropalladium (II) (0.041 g, 0.058 mmol) was added to a degassed solution of (E)-3-(2-(4-methoxybenzylamino)-6-(4,4,5,5-tetramethyl-1,3,2-dioxaborolan-2-yl)quinolin-3-yl)-N-(3,3-dimethylbutyl)-2-methylacrylamide (0.65 g, 1.2 mmol), potassium acetate (0.23 g, 2.3 mmol), and 2-bromo-3-methylpyridine (0.20 mL, 1.8 mmol) in EtOH (12 mL) and water (2 mL). The resulting solution was refluxed for 12 h. Then the reaction mixture was cooled and partitioned between dichromethane and 9:1 saturated ammonium chloride/ammonium hydroxide aqueous solution. The aqueous layer was extracted with DCM and the combined organics were washed with a 9:1 saturated ammonium chloride/ammonium hydroxide solution, water, brine, dried over sodium sulfate, filtered and concentrated. The crude product was purified by silica gel column chromatography (1:1 Hex/EtOAc) to afford (E)-3-(2-(4-methoxybenzylamino)-6-(3-methylpyridin-2-yl)quinolin-3-yl)-N-(3,3-dimethylbutyl)-2-methylacrylamide.
Step 6
Palladium on carbon (0.71 g, 0.67 mmol) was added to a solution of (E)-3-(2-(4-methoxybenzylamino)-6-(3-methylpyridin-2-yl)quinolin-3-yl)-N-(3,3-dimethylbutyl)-2-methylacrylamide (0.35 g, 0.67 mmol) in EtOH (6 mL). The flask was degassed with hydrogen gas and then stirred under a balloon of hydrogen gas for 12 h. The reaction was filtered through celite and washed with EtOH and EtOAc. The filtrate was concentrated to afford 3-(2-(4-methoxybenzylamino)-6-(3-methylpyridin-2-yl)quinolin-3-yl)-N-(3,3-dimethylbutyl)-2-methylpropanamide which was used without further purification.
Step 7
TFA (6.0 mL, 78 mmol) was added to 3-(2-(4-methoxybenzylamino)-6-(3-methylpyridin-2-yl)quinolin-3-yl)-N-(3,3-dimethylbutyl)-2-methylpropanamide (0.30 g, 0.57 mmol) and the reaction was heated to 65° C. After 5 h, the reaction was concentrated and the crude material dissolved in dichloromethane. The organic layers were washed with 1N NaOH and the aqueous layer was again extracted with DCM. The combined organic layers were washed with brine, dried over sodium sulfate, and concentrated. The crude product was purified by silica gel column chromatography (20:1 DCM/

MeOH with 2M NH₃) to afford 3-(2-amino-6-(3-methylpyridin-2-yl)quinolin-3-yl)-N-(3,3-dimethylbutyl)-2-methylpropanamide. MS (ESI, pos. ion) m/z: 405 (M+1).

Example 6

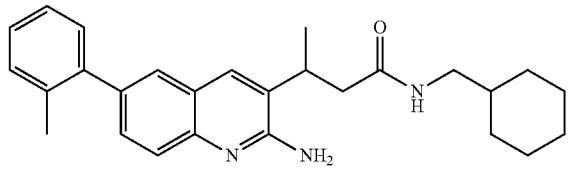 [SMILES: Cc1ccccc1-c1ccc2nc(N)c(C(C)CC(=O)NCC3CCCCC3)cc2c1]

Synthesis of 3-(2-amino-6-o-tolylquinolin-3-yl)-N-(cyclohexylmethyl)butanamide

Step 1:
To a 500 mL RBF containing 6-bromoquinoline-3-carboxylic acid (1.0 g, 4.0 mmol) was added THF (15 mL) and the mixture was allowed to stir at 23° C. for 2 min. At this time, 4-methylmorpholine (1.3 ml, 12 mmol) and 2-chloro-4,6-dimethoxy-1,3,5-triazine (1.0 g, 6.0 mmol) were added in single portions. The reaction was allowed to stir for 1 h and then N,O-dimethylhydroxylamine hydrochloride (0.43 g, 4.4 mmol) was added in one portion. The reaction was allowed to stir overnight and the diluted with water. It was extracted with EtOAc (3×). The combined organics were washed with sodium carbonate (3×10%), ammonium chloride (2× sat.), sodium bicarbonate and brine. It was dried with magnesium sulfate, filtered and concentrated to give an off white solid. The reaction was repeated on a 3.0 g scale of 6-bromoquinoline-3-carboxylic acid. The combined theoretical yield=4.71 g (135%)) was subjected to a 120 g Isco column (30 to 60% EtOAc in hexanes) to give 6-bromo-N-methoxy-N-methylquinoline-3-carboxamide Step 2:
To a 500 mL RBF containing 6-bromo-N-methoxy-N-methylquinoline-3-carboxamide (4.00 g, 13.6 mmol) was added THF (50 mL) and the mixture was allowed to stir at 0° C. for 5 min. At this time, methyl magnesium bromide (3 M in ether) (4.5 mL, 13.6 mmol) was added in a fast dropwise manner. After 1 h the material was quenched with the addition sodium bicarbonate (sat 100 mL) and extracted with EtOAc (3×100 mL). The combined organics were washed with brine, dried with sodium sulfate, filtered, concentrated and subjected to 80 g Isco column to give 1-(6-bromoquinolin-3-yl)ethanone as a white solid.

Step 3:
1-(6-Bromoquinolin-3-yl)ethanone (170 mg, 680 μmol) was placed in a microwave tube and toluene (2 mL) was added before the addition of methyl(triphenylphosphoranylidene) acetate (227 mg, 680 μmol) in one portion. The tube was irradiated in the microwave at 140° C. for 10 min. An additional portion of (triphenylphosphoranylidene)acetate (80 mg) was added to the tube and it was then irradiated in the microwave at 160° C. for 60 min. The crude reaction material was loaded directly to a 40 g Isco column to give methyl 3-(6-bromoquinolin-3-yl)but-2-enoate (150 mg) as a mixture of E and Z isomers.

Step 4:
A microwave tube (25 mL) was charged with 1,4-dioxane (4 mL) and methyl 3-(6-bromoquinolin-3-yl)but-2-enoate (320 mg, 1045 μmol). O-tolylboronic acid (242 mg, 1777 μmol) was added to the tube followed by sodium carbonate (1045 μl, 2090 μmol) and tetrakis(triphenylphosphine)palladium(0) (60 mg). The tube was irradiated in a microwave at 90° C. for 20 min. The crude mixture was diluted with sodium bicarbonate (75 mL, sat) and extracted with EtOAc (3×30 mL). The combined organics were washed with brine, dried with sodium sulfate, filtered and concentrated to give methyl 3-(6-o-tolylquinolin-3-yl)but-2-enoate (325 mg, 98%) as a yellow oil. The material was taken directly to the next reaction.

Step 5:
To a 500 mL RBF containing methyl 3-(6-o-tolylquinolin-3-yl)but-2-enoate (325 mg, 1024 μmol) was added THF (6 mL) and water (2 mL) the mixture was allowed to stir at 23° C. for 2 min. At this time, lithium hydroxide (245 mg, 10240 μmol) and the reaction was allowed to stir for 48 h. The material was poured into EtOAc (50 mL) and HCl (0.5 M, 100 mL) was added to the flask. The layers were separated and the aqueous layer was extracted with DCM (4×30 ml). The combined organic layers were washed with brine, dried with sodium sulfate, filtered and concentrated to give carboxylic acid (369 mg). The crude acid was dissolved in NMP (4928 μL, 51200 μmol) and DIPEA (715 μL, 4096 μmol) was added before the addition of cyclohexanemethylamine (348 μL, 3072 μmol) and tbtu coupling reagent (493 mg, 1536 μmol). The reaction was allowed to stir for 12 h and then poured into sodium bicarbonate. The aqueous layer was extracted with EtOAc (3×25 mL). The combined organics were washed the brine, dried with sodium sulfate, filtered and subjected to a 40 g Isco columns to give (N-(cyclohexylmethyl)-3-(6-o-tolylquinolin-3-yl)but-2-enamide (300 mg, 74% yield).

Step 6:
A RBF (25 mL) was charged with (cyclohexylmethyl)-3-(6-o-tolylquinolin-3-yl)but-2-enamide (184 mg), MeOH (15 mL) and palladium on carbon (10% by weight, 50 mg). Hydrogen was bubbled through the reaction for 15 min and then it was allowed to stir for 2 h under 1.0 atm of hydrogen. The crude mixture was passed though a plug of silica gel under a pad of celite and eluted with EtOAc. The volatiles were removed by rotary evaporation to give N-(cyclohexylmethyl)-3-(6-o-tolylquinolin-3-yl) butanamide.

Step 7:
To a RBF (50 mL) containing N-(cyclohexylmethyl)-3-(6-o-tolylquinolin-3-yl) butanamide (185 mg) was added DCM (15 mL) and the flask was placed on an ice bath. After 10 min, mCPBA (239 mg, 3 eq) were added in one portion. The reaction was allowed to stir for 30 min and then diluted with DCM (75 mL). The organic layer was washed with sodium bicarbonate (sat, 3×50 mL), brine and dried with sodium sulfate. The dried solution was filtered, concentrated and diluted with 1-(trifluoromethyl)benzene (10 mL). To the RBF containing the N-oxide was added tert-butylamine (338 mg, 10 eq) followed by p-toluenesulfonic anhydride (196 mg, 1.3 eq) portion wise over 3 min. After 5 min, the crude reaction was dilute with DCM (50 ml), washed with NaOH (1N, 2×50 mL), sodium bicarbonate (sat, 1×50 mL), brine, dried with sodium sulfate. The dried solution was filtered and concentrated to give 300 mg crude brown oil. This material was purified by chromatography on a 40 g Isco column (5 to 35% EtOAc in hexanes) to give 3-(2-(tert-butylamino)-6-o-tolylquinolin-3-yl)-N-(cyclohexylmethyl) butanamide (105 mg, 48% yield). A portion of this material was subjected to TFA (5 mL) at 72° C. for 1 h. The TFA was removed by rotary evaporator and then diluted with dichloromethane. The organic layer was washed with NaOH (1N, 50 mL). The aqueous layer was back extracted with DCM, washed with brine, dried with sodium sulfate, filtered and concentrated to give 3-(2-amino-6-o-tolylquinolin-3-yl)-N-(cyclohexylmethyl)butanamide of a slightly brown oil. MS (ESI, pos. ion) m/z: 412 (M+1).

Example 7

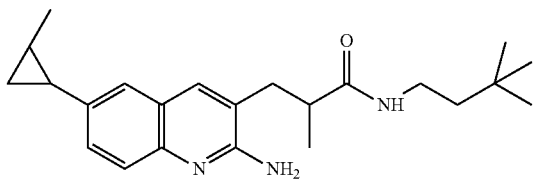 [SMILES: CC(Cc1cc2cc(C3CC3C)ccc2nc1N)C(=O)NCCC(C)(C)C]

Synthesis of 3-(2-amino-6-(2-methylcyclopropyl)quinolin-3-yl)-N-(3,3-dimethylbutyl)-2-methylpropanamide Step 1:
(Z)-Prop-1-enylboronic acid (3.00 g, 34.9 mmol) and pinacol (4.13 g, 34.9 mmol) in ether (80 mL) was stirred for 12 h with magnesium sulfate. The reaction mixture was filtered and carefully concentrated. The crude oil was diluted with pentane and filtered. The filtrate was concentration to afford (Z)-4,4,5,5-tetramethyl-2-(prop-1-enyl)-1,3,2-dioxaborolane.
Step 2:
Diethylzinc (1.1 M Toluene) (38 ml, 41 mmol) was added to (Z)-4,4,5,5-tetramethyl-2-(prop-1-enyl)-1,3,2-dioxaborolane (5.8 g, 35 mmol) dissolved in toluene (10 mL) followed by diiodomethane (3.9 mL, 48 mmol) at 0° C. The reaction was heated at 50° C. and monitored by TLC (30:1 Hex/EtOAc). After 12 h the reaction was cooled, diluted with diethyl ether, and poured into ice cold 1 N HCl. The layers are separated and the organic layer was washed with water, 10% sodium carbonate, brine, dried over magnesium sulfate, filtered, and concentrated to afford (Z)-4,4,5,5-tetramethyl-2-(2-methylcyclopropyl)-1,3,2-dioxaborolane as a racemic mixture. The compound was used directly for the next reaction without further purification.
Step 3:
Sodium periodate (7.05 g, 33.0 mmol) was added to a RT solution of (Z)-4,4,5,5-tetramethyl-2-(2-methylcyclopropyl)-1,3,2-dioxaborolane (2.0 g, 11.0 mmol) in THF/H$_2$O (4:1, 100 mL). The mixture was stirred 5 min and then 2 N HCl (3.63 ml, 7.25 mmol) was added. The reaction was stirred for 12 h and then diluted with water. The reaction was extracted with EtOAc and the combined organic extracts were washed with water, brine, dried (Na$_2$SO$_4$), filtered, and concentrated in vacuo to afford (Z)-2-methylcyclopropylboronic acid.
Step 4:
Palladium Acetate (0.0061 g, 0.027 mmol) and 2-Dicyclohexylphosphino-2,6-dimethoxy-1,1-biphenyl (S-Phos) (0.022 g, 0.054 mmol) were added to a degassed (N$_2$) solution of (Z)-2-methylcyclopropylboronic acid, (E)-3-(2-(4-methoxybenzylamino)-6-bromoquinolin-3-yl)-N-(3,3-dimethylbutyl)-2-methylacrylamide (0.13 g, 0.25 mmol, prepared as in Step 3 of Example 9), and potassium phosphate (0.18 g, 0.86 mmol) in 10:1 toluene/water (0.4 mL). The reaction was heated at 100° C. for 12 hours, cooled, diluted with EtOac, and washed with water and 10:1 saturated ammonium chloride/ammonium hydroxide solution. The aqueous layer was back extracted with EtOAc and the combined organic layers were washed with water, brine, dried over sodium sulfate, filtered, and concentrated. The crude product was purified by silica gel chromatography (2.5:1 Hexanes/EtOAc) to afford (E)-3-(2-(4-methoxybenzylamino)-6-(2-methylcyclopropyl)quinolin-3-yl)-N-(3,3-dimethylbutyl)-2-methylacrylamideas a racemic mixture.

The title compound was prepared by following a method analogous to that described in steps 6 and 7 of Example 6. MS (ESI, pos. ion) m/z: 368 (M+1).

Example 8

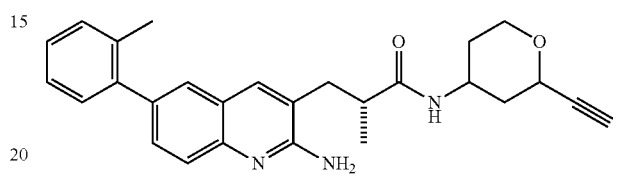

Synthesis of (R)-3-(2-amino-6-o-tolylquinolin-3-yl)-N-((2R,4S)-2-ethynyltetrahydro-2H-pyran-4-yl)-2-methylpropanamide Step 1:
To a solution of but-3-en-1-ol (5.0 g, 69.3 mmol) and propiolaldehyde (4.12 g, 76 mmol) in acetonitrile (108 mL, 2080 mmol) at RT was added bismuth(III) trifluoromethanesulfonate (6.83 g, 10.4 mmol). The reaction was stirred overnight. The reaction was quenched with water and the aqueous layer was extracted with EtOAc. The organic layer was then washed with water and brine (3× ea.), dried over Na$_2$SO$_4$ and concentrated in vacuo to remove the solvent. The crude material was purified by column chromatography (0-100% (10% (MeOH/DCM)/DCM) to yield N-(2-ethynyltetrahydro-2H-pyran-4-yl)acetamide as a clear oil.
Step 2:
A solution of N-(2-ethynyltetrahydro-2H-pyran-4-yl)acetamide (1.0 g, 5.98 mmol) in 4N HCl (20 mL, 80 mmol) in dioxane was heated to 70° C. for one week. The reaction was concentrated and purified by column chromatography (0-100% (10% MeOH/DCM—100% DCM) to yield cis-2-ethynyltetrahydro-2H-pyran-4-amine as a clear oil.
Step 3:
6-Bomo-2-chloroquinoline-3-carbaldehyde (10 g, 37.0 mmol) was dissolved in NMP 200 mL in a 350 mL sealable flask. 2-Methylpropan-2-amine (23 mL, 217 mmol) was added and the reaction mixture was sealed to heated at 130° C. for 24 h. After cooling, the mixture was poured into 1N HCl 200 mL and stirred for 1.5 h. The reaction was completed. The precipitates was isolated by filtration and washed with water. The solid was collected and dried on vacuum pump overnight to give 6-bromo-2-(tert-butylamino)quinoline-3-carbaldehyde as a yellow solid.
Step 4:
Lithium chloride (3 g, 66 mmol) was stirred overnight in MeCN (300 mL). To the cloudy solution was added 6-bromo-2-(tert-butylamino)quinoline-3-carbaldehyde (10.21 g, 33 mmol), ethyl 2-(diethoxyphosphoryl)propanoate (9 ml, 40 mmol) and 2,3,4,6,7,8,9,10-octahydropyrimido[1,2-a]azepine (5 ml, 33 mmol). The reaction mixture was stirred at RT for 10 h. Then the reaction mixture was added saturated sodium bicarbonate solution and extracted with EtOAc three times. The combined organic layers were washed with brine and dried on sodium sulfate, filtered and concentrated. The crude material was purified by column chromatography with 30-60% DCM/hexane to give (E)-ethyl 3-(6-bromo-2-(tert-butylamino)quinolin-3-yl)-2-methylacrylate.

Step 5:

(E)-ethyl 3-(6-bromo-2-(tert-butylamino)quinolin-3-yl)-2-methylacrylate (4.43 g, 11 mmol), o-tolylboronic acid (2 g, 17 mmol), bis(di-tert-butyl(4-dimethylaminophenyl)phosphine)dichloropalladium(II) (0.2 g, 0.2 mmol), potassium acetate (2 g, 23 mmol) and water (4 ml, 226 mmol) were combined in EtOH 100 mL and heated at 80° C. for 2 h. The solvent was removed and the crude material was taken in saturated sodium bicarbonate solution and extracted with EtOAc. The combined organic layers were washed with brine, dried on sodium sulfate, filtered and concentrated. The crude material was purified by column chromatography with 0-100% EtOAc/hexane. The purified material was dissovled in methanol and Pd/C (2 g) was added. The reaction mixture was stirred under hydrogen atmosphere overnight. The mixture was filtered through a pad of celite. The filtrate was collected and concentrated. The crude material was purified by column chromatography with 40-60% DCM/hexane to give ethyl 3-(2-(tert-butylamino)-6-o-tolylquinolin-3-yl)-2-methylpropanoate.

Step 6

Ethyl 3-(2-(tert-butylamino)-6-o-tolylquinolin-3-yl)-2-methylpropanoate (5.45 g, 13 mmol) was dissolved in MeOH 100 mL and 1N NaOH (54 ml, 54 mmol) was added. The reaction mixture was refluxed for 3 h then cooled to RT. 5N HCl was added to neutralize the pH to 2-3 and the solvent was removed. The residue was taken in 1N HCl and extracted with DCM (3×). The combined organic layers were washed with water and brine, dried on sodium sulfate, filtered and concentrated to give 3-(2-(tert-butylamino)-6-o-tolylquinolin-3-yl)-2-methylpropanoic acid as a yellow solid. This material was subject to purification by chiral HPLC to give (R)-3-(2-(tert-butylamino)-6-o-tolylquinolin-3-yl)-2-methylpropanoic acid and (S)-3-(2-(tert-butylamino)-6-o-tolylquinolin-3-yl)-2-methylpropanoic acid.

Step 7:

A solution of (R)-3-(2-(tert-butylamino)-6-o-tolylquinolin-3-yl)-2-methylpropanoic acid (70 mg, 0.19 mmol), cis-2-ethynyltetrahydro-2H-pyran-4-amine (27.9 mg, 0.22 mmol), N-ethyl-N-isopropylpropan-2-amine (42.8 μL, 0.242 mmol) and 2-(3H-[1,2,3]triazolo[4,5-b]pyridin-3-yl)-1,1,3,3-tetramethylisouronium hexafluorophosphate(V) (92 mg, 0.24 mmol) in DMF (1.86 mL) was stirred at RT for 2 h. The reaction was quenched with water and the aqueous layer was extracted with EtOAc. The organic layer was then washed with water and brine (3× each), dried over Na$_2$SO$_4$ and concentrated in vacuo to remove the solvent. The crude material was purified by column chromatography (0-40% Hex/EtOAc) to yield the separated diastereomers (R)-3-(2-(tert-butylamino)-6-o-tolylquinolin-3-yl)-N-(cis-2-ethynyltetrahydro-2H-pyran-4-yl)-2-methylpropanamide as a clear oils.

Step 8:

A solution of (R)-3-(2-(tert-butylamino)-6-o-tolylquinolin-3-yl)-N-(cis-2-ethynyltetrahydro-2H-pyran-4-yl)-2-methylpropanamide (15 mg, 0.031 mmol) in neat TFA (5 ml, 64.9 mmol) was heated to 70° C. for 40 min. The reaction was concentrated and purified by HPLC to yield the title compound (R)-3-(2-amino-6-o-tolylquinolin-3-yl)-N-(cis-2-ethynyltetrahydro-2H-pyran-4-yl)-2-methylpropanamide. (ESI, pos. ion) m/z: 428 (M+1).

Example 9

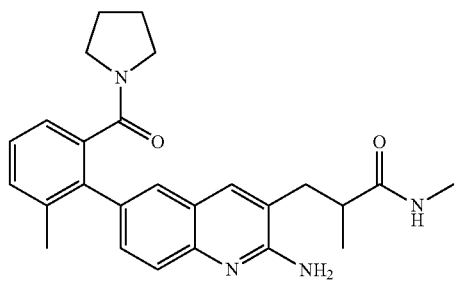 [SMILES: CNC(=O)C(C)Cc1cc2cc(-c3c(C)cccc3C(=O)N3CCCC3)ccc2nc1N]

Synthesis of 3-(2-amino-6-(2-methyl-6-(pyrrolidine-1-carbonyl)phenyl)quinolin-3-yl)-N,2-dimethylpropanamide Step 1:

2-Bromo-3-methylbenzoic acid (1.03 g, 4.79 mmol) was dissolved in thionyl chloride (15 mL, 206 mmol) and stirred at 80° C. for 30 min. The solution was evaporated to dryness under reduced pressure and the white solid residue dried under high vacuum. It was dissolved in DCM and added to a solution of pyrrolidine (0.80 mL, 9.58 mmol) and DIEA (1.67 mL, 9.58 mmol) in DCM (50 mL) and the reaction stirred overnight. Water (100 mL) and DCM (100 mL) were added and the phases mixed and separated. The organic was washed with 1N HCl (50 mL) then 1N sodium hydroxide (60 mL) before drying with magnesium sulfate and evaporating to dryness under reduced pressure. Purification using silica chromatography (hexane to ethyl acetate gradient) gave the (2-bromo-3-methylphenyl)(pyrrolidin-1-yl)methanone as a clear oil that solidified into a waxy solid on standing.

Step 2:

A mixture of (E)-ethyl 3-(6-bromo-2-(tert-butylamino)quinolin-3-yl)-2-methylacrylate (2.2 g, 5.62 mmol), potassium acetate (1.05 mL, 16.87 mmol), 1,1'-bis(diphenylphosphino)ferrocene-palladium dichloride (0.23 g, 0.28 mmol) and bis(pinacolato)diboron (1.71 g, 6.75 mmol) in degassed dioxane 40 mL was heated at 85° C. overnight. The mixture was cooled to RT and filtered through a pad of celite. The filtrate was collected and concentrated. The crude material was purified by column chromatography with 20-45% EtOAc/hexane to give (E)-ethyl 3-(2-(tert-butylamino)-6-(4,4,5,5-tetramethyl-1,3,2-dioxaborolan-2-yl)quinolin-3-yl)-2-methylacrylate.

Step 3:

(2-Bromo-3-methylphenyl)(pyrrolidin-1-yl)methanone (0.39 g, 1.44 mmol), 2-dicyclohexylphosphino-2',4',6%-triisopropylbiphenyl (0.057 g, 0.120 mmol), (E)-ethyl 3-(2-(tert-butylamino)-6-(4,4,5,5-tetramethyl-1,3,2-dioxaborolan-2-yl)quinolin-3-yl)-2-methylacrylate (0.53 g, 1.20 mmol), palladium diacetate (0.013 g, 0.060 mmol), and potassium acetate (0.35 g, 3.61 mmol) were suspended in a mixture of ethanol (2 mL) and water (0.5 mL) and heated to 145° C. for 30 min in the microwave. The crude was partitioned between ethyl acetate (60 mL) and water (50 mL) and the organic dried with magnesium sulfate before evaporating to dryness under reduced pressure. Purification using silica chromatography (hexane to ethyl acetate gradient) gave the desired (E)-ethyl 3-(2-(tert-butylamino)-6-(2-methyl-6-(pyrrolidine-1-carbonyl)phenyl)quinolin-3-yl)-2-methylacrylate. This material was dissolved in methanol (50 g, 12.02 mmol) in water (15 mL). The mixture was heated to reflux for 45 min after which 2N HCl (6 mL) was added and the solution concentrated under reduced pressure to ~25 mL. Water (100 mL) and DCM (100 mL) were added and the phases mixed and separated. The organic was dried with magnesium sulfate and evaporated to dryness to give (E)-3-(2-(tert-butylamino)-6-(2-methyl-6-(pyrrolidine-1-carbonyl)phenyl)quinolin-3-yl)-2-methylacrylic acid which was used without purification.

Step 4:
(E)-3-(2-(tert-butylamino)-6-(2-methyl-6-(pyrrolidine-1-carbonyl)phenyl)quinolin-3-yl)-2-methylacrylic acid (0.082 g, 0.17 mmol) was dissolved in N-methylpyrrolidinone (0.75 mL) and treated with methylamine (33% wt. solution in absolute ethyl alcohol, 0.050 mL, 0.48 mmol) and Knorr's reagent (0.081 g, 0.25 mmol). The mixture was stirred for 5 min then water (25 mL) and DCM (10 mL) were added and the phases mixed and separated. The organic was dried and evaporated to dryness under reduced pressure. Purification using silica chromatography (0-10% methanol in DCM gradient) gave (E)-3-(2-(tert-butylamino)-6-(2-methyl-6-(pyrrolidine-1-carbonyl)phenyl)quinolin-3-yl)-N, 2-dimethylacrylamide. This material was dissolved in methanol (30 mL) and DCM (10 mL) and palladium on carbon (10% by wt, 0.019 g, 0.017 mmol) was added. The slurry was stirred under hydrogen for 40 min after which the reaction was filtered through a pad of celite and evaporated to dryness under reduced pressure. The crude was dissolved in trifluoroacetic acid (40 mL) and heated to gentle reflux for 80 min. The solution was then evaporated to dryness under reduced pressure, free based with DCM and saturated sodium bicarbonate, and purified using silica chromatography (0-10% methanol in DCM gradient) to give 3-(2-amino-6-(2-methyl-6-(pyrrolidine-1-carbonyl)phenyl)quinolin-3-yl)-N,2-dimethylpropanamide. MS (ESI, pos. ion) m/z: 431 (M+1).

Example 10

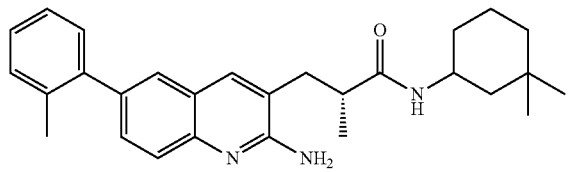 [SMILES: Cc1ccccc1-c1ccc2nc(N)c(C[C@@H](C)C(=O)NC3CCCC(C)(C)C3)cc2c1]

Synthesis of (2R)-3-(2-amino-6-o-tolylquinolin-3-yl)-N-(3,3-dimethylcyclohexyl)-2-methylpropanamide Step 1:
A 100 mL RBF was charged with 3,3-dimethylcyclohexanone (3.48 g, 27.6 mmol), hydroxylamine hydrochloride (2.01 g, 29.0 mmol), and 20 mL of MeOH. This mixture was heated to 60° C. for 1 h. To this solution was added Raney Nickel (approx 300 mg). This mixture was placed under a hydrogen atmosphere (1 atm) and heating was continued (60° C.) for 12 h. After that time, the solution was filtered, acidified with 1M HCl, and concentrated to give 3,3-dimethylcyclohexanamine HCl as an off-white solid.

Step 2:
A 20 mL vial was charged with (R)-3-(2-(tert-butylamino)-6-o-tolylquinolin-3-yl)-2-methylpropanoic acid (0.13 g, 0.33 mmol, prepared as in Example 8, Step 3-6), 3,3-dimethylcyclohexanaminium chloride (0.068 g, 0.42 mmol), TBTU (0.13 g, 0.42 mmol), and 2 mL of NMP. To this was added Hünig's base (0.11 g, 0.83 mmol). After stirring at RT for 2 h, the mixture was diluted with water and extracted with EtOAc. The combined organic layers were dried and concentrated to give an oil, which was purified via silica gel column chromatography to give the t-Bu protected amide intermediate. To this material, was added 3 mL of TFA and 3 mL of DCM. This mixture was heated at 40° C. for 12 h, then concentrated and purified by silica gel column chromatography (0-8% NH$_3$/MeOH in CH$_2$Cl$_2$) to give (2R)-3-(2-amino-6-o-tolylquinolin-3-yl)-N-(3,3-dimethylcyclohexyl)-2-methylpropanamide as a white solid. MS (ESI, pos. ion) m/z: 430 (M+1).

Example 11

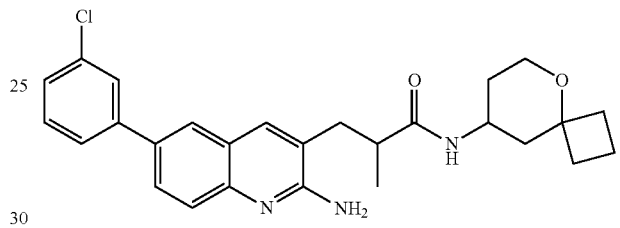

Synthesis of 3-(2-amino-6-(3-chlorophenyl)-3-quinolinyl)-2-methyl-N-(5-oxaspiro[3,5]non-8-yl)propanamide Step 1:
A 500 mL RBF was charged with but-3-en-1-ol (10.29 g, 143 mmol), cyclobutanone (10.0 g, 143 mmol), and 100 mL of CH$_2$Cl$_2$. To this was added methanesulfonic acid (19.44 mL, 300 mmol). The mixture was stirred at RT for 1 day then diluted with saturated aqueous NaHCO$_3$. The layers were separated and the organics were dried and concentrated to give an oil material. Purification via silica gel column chromatography (0-40% ethyl acetate in hexanes) gave 5-oxaspiro[3.5]nonan-8-yl methanesulfonate as a slightly yellow oil.

Step 2:
A 500 mL RBF was charged with 5-oxaspiro[3.5]nonan-8-yl methanesulfonate (20.5 g, 93 mmol), azidotrimethylsilane (16.08 g, 140 mmol), and 100 mL of THF. To this was added TBAF (1M in THF, 140 mL, 140 mmol). The mixture was heated at reflux for 2 d and then cooled to RT. The mixture was concentrated and purified via silica gel column chromatography (0-10% ethyl acetate in hexanes) to give 8-azido-5-oxaspiro[3.5]nonane as a colorless oil.

Step 3:
A 500 mL RBF was charged with 8-azido-5-oxaspiro[3.5]nonane (12.0 g, 71.8 mmol), 200 mL of EtOH, and 2.0 g of 10% Pd/C. The mixture was placed under a hydrogen atmosphere (1 atm) for 5 h, then filtered and concentrated. The oil was acidified with 4N HCl in dioxane to give 5-oxaspiro[3.5]nonan-8-aminium chloride as a gray solid.

Step 4:
A 500 mL RBF was charged with (1-ethoxy-1-oxopropan-2-yl)triphenylphosphonium bromide (13.75 g, 31.0 mmol) 6-bromo-2-(tert-butylamino)quinoline-3-carbaldehyde (8.58 g, 27.9 mmol, prepared as in Example 15, Step 3), potassium carbonate (6.43 g, 46.5 mmol), and 100 mL of EtOH. The mixture was heated to 80° C. for 1 h then cooled to RT and concentrated. The resulting oil was purified via silica gel column chromatography (0-15% EtOAc in hexanes) to give (E)-ethyl 3-(6-bromo-2-(tert-butylamino)quinolin-3-yl)-2-methylacrylate as a yellow solid.

Step 5:
A 250 mL RBF was charged with (E)-ethyl 3-(6-bromo-2-(tert-butylamino)quinolin-3-yl)-2-methylacrylate (6.80 g, 17.38 mmol) and 50 mL of MeOH. To this was added 5N NaOH (13.90 mL, 69.5 mmol). The yellow mixture was heated at 80° C. for 1 h, then cooled to RT and concentrated. The oil was diluted with water and acidified to pH 4 with concentrated HCl. The mixture was extracted with EtOAc, dried, and concentrated to give (E)-3-(6-bromo-2-(tert-butylamino)quinolin-3-yl)-2-methylacrylic acid as a yellow solid.

Step 6:
A 250 RBF was charged with (E)-3-(6-bromo-2-(tert-butylamino)quinolin-3-yl)-2-methylacrylic acid (6.10 g, 16.8 mmol), 2,2-dimethyltetrahydro-2H-pyran-4-aminium chloride (3.34 g, 20.2 mmol), HATU (7.01 g, 21.8 mmol), and 30 mL of DMF. To this was added Hünig's base (8.78 mL, 50.4 mmol). The resulting mixture was stirred at RT for 30 min then diluted with water and extracted with EtOAc. The organics were dried and concentrated to give an oil. This oil was purified to via silica gel column chromatography (0-70% ethyl acetate in hexanses) to give (E)-3-(6-bromo-2-(tert-butylamino)quinolin-3-yl)-N-(2,2-dimethyltetrahydro-2H-pyran-4-yl)-2-methylacrylamide as a yellow solid.

Step 7:
A 300 mL pressure tube was charged with (E)-3-(6-bromo-2-(tert-butylamino)quinolin-3-yl)-N-(2,2-dimethyltetrahydro-2H-pyran-4-yl)-2-methylacrylamide (5.0 g, 10.54 mmol) and 100 mL of MeOH. After purging with nitrogen for 3 min, 1,1'-bis(di-1-propylphosphino)ferrocene(1,5-cyclooctadiene)rhodium(tetrafluoroborate (0.12 g, 0.16 mmol) was added and the vessel was placed under a hydrogen atmosphere for 3 h (50 psi). The reaction was concentrated and purified via silica gel column chromatography (0-60% ethyl acetate in hexanes) to give 3-(6-bromo-2-(tert-butylamino)quinolin-3-yl)-2-methyl-N-(5-oxaspiro[3.5]nonan-8-yl)propanamide.

Step 8:
A 20 mL microwave compatible vial was charged with 3-(6-bromo-2-(tert-butylamino)quinolin-3-yl)-2-methyl-N-(5-oxaspiro[3.5]nonan-8-yl)propanamide (0.50 g, 1.02 mmol), 3-chlorophenylboronic acid (0.20 g, 1.28 mmol), potassium acetate (0.20 g, 2.05 mmol), bis(di-tert-butyl(4-dimethylaminophenyl)phosphine)dichloropalladium(II) (0.036 g, 0.051 mmol), and 6 mL of 6:1 EtOH/water. The tube was sealed was heated in a microwave at 100° C. for 20 min. The mixture was then concentrated and purified silica gel column chromatography to give the t-Bu protected intermediate. This material was dissolved in TFA then heated at 85° C. (thermal) for 45 min. The mixture was concentrated and purified via silica gel column chromatography (0-8% 2N $NH_3$ in MeOH/$CH_2Cl_2$) to give a white solid. This solid was recrystallized from MeOH to give 3-(2-amino-6-(3-chlorophenyl)-3-quinolinyl)-2-methyl-N-(5-oxaspiro[3,5]non-8-yl)propanamide. MS (ESI, pos. ion) m/z: 464 (M+1).

Example 12

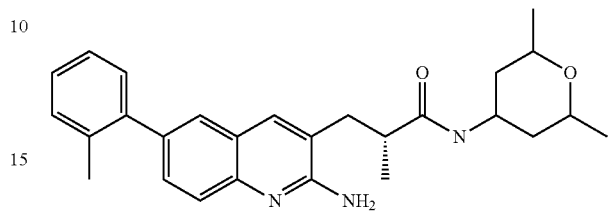

Synthesis of (2R)-3-(2-amino-6-o-tolylquinolin-3-yl)-N-(cis-2,6-dimethyltetrahydro-2H-pyran-4-yl)-2-methylpropanamide Step 1:
A solution of 2,6-dimethyl-4-pyrone (5.0 g, 40.3 mmol) in ethanol was charged with Pd/C (0.86 g, 0.40 mmol). The mixture was subjected to pressurized $H_2$ conditions using a parr hydrogenator (50 psi) and the mixture was shaken overnight. Afterwards, the mixture was filtered through a pad of celite, and the filtrate was concentrated. The crude material was purified by column chromatography using 5% to 60% EtOAc-hexanes eluent. The desired fractions were combined and concentrated to give cis-2,6-dimethyldihydro-2H-pyran-4(3H)-one as a colorless oil.

Step 2:
A solution of cis-2,6-dimethyldihydro-2H-pyran-4(3H)-one (2.05 g, 16.0 mmol) and hydroxylamine chloride (0.73 mL, 17.6 mmol) in methanol was heated to 60° C. for 2 h. After the mixture was cooled to RT, a spatula full of Raney nickel (0.19 g, 3.20 mmol) was added to the reaction mixture. The reaction was subjected to $H_2$ atmosphere using a balloon. The mixture was stirred overnight at 50° C. The reaction mixture was filtered through a pad of celite. The filtrate was acidified with HCl (4.0 mL, 15.99 mmol)-4N in dioxane, and the resulting solution was concentrated. The resulting solid was washed with ether and filtered to give cis-2,6-dimethyltetrahydro-2H-pyran-4-amine hydrochloride as a white solid.

The titled compound was prepared by following the procedure described in Example 10, Step 2 to give (2R)-3-(2-amino-6-o-tolylquinolin-3-yl)-N-(cis-2,6-dimethyltetrahydro-2H-pyran-4-yl)-2-methylpropanamide. MS (ESI, pos. ion) m/z: 433 (M+1).

The following examples 1-79 in Table I were prepared by methods and Steps analogous to those described in Examples 1-12 above. Additional examples 80-171 were prepared according to the scheme indicated. Provided also is the mass spectral data and BACE enzyme and cell-based assay data ($IC_{50}$'s in uM ranges) for each example, where available.

TABLE 1

| Ex. No. | Compound Name | Method | Observed MS | BACE 1 FRET assay (uM) | HEK cell assay (uM) |
|---|---|---|---|---|---|
| 1 | 3-(2-amino-6-o-tolylquinolin-3-yl)-N-(cyclohexylmethyl)-N-methylpropanamide | | 402 | + | ++++ |
| 13 | 3-(2-amino-6-o-tolylquinolin-3-yl)-N-cyclohexylpropanamide | | 388 | ++++ | +++ |

TABLE 1-continued

| Ex. No. | Compound Name | Method | Observed MS | BACE 1 FRET assay (uM) | HEK cell assay (uM) |
|---|---|---|---|---|---|
| 14 | 3-(2-amino-6-o-tolylquinolin-3-yl)-N-(cyclohexylmethyl)propanamide | | 402 | ++++ | +++ |
| 15 | 3-(2-amino-6-o-tolylquinolin-3-yl)-N-(tetrahydro-2H-pyran-4-yl)propanamide | | 390 | ++++ | + |
| 16 | 3-(2-amino-6-o-tolylquinolin-3-yl)-N-(tetrahydro-2H-pyran-4-yl)propanamide | | 348 | ++ | ++ |
| 17 | 3-(2-amino-6-o-tolylquinolin-3-yl)-N-((tetrahydrofuran-2-yl)methyl)propanamide | | 390 | ++++ | + |
| 18 | 3-(2-amino-6-o-tolylquinolin-3-yl)-N-(2-methoxyethyl)propanamide | | 364 | ++++ | + |
| 19 | 3-(2-amino-6-o-tolylquinolin-3-yl)-N-((tetrahydro-2H-pyran-4-yl)methyl)propanamide | | 404 | ++++ | ++ |
| 20 | 3-(2-amino-6-o-tolylquinolin-3-yl)-N-(3,3-dimethylbutyl)propanamide | | 390 | ++++ | +++ |
| 21 | 3-(2-amino-6-o-tolylquinolin-3-yl)-N-neopentylpropanamide | | 376 | ++++ | + |
| 22 | 3-(2-amino-6-o-tolylquinolin-3-yl)-N-(cyclohexylmethyl)-2-methylpropanamide | | 416 | ++++ | ++++ |
| 23 | 3-(2-amino-6-o-tolylquinolin-3-yl)-N-benzylpropanamide | | 396 | ++++ | ++++ |
| 24 | 3-(2-amino-6-o-tolylquinolin-3-yl)-N-(2-cyclohexylethyl)propanamide | | 416 | ++++ | ++++ |
| 25 | 3-(2-amino-6-o-tolylquinolin-3-yl)-N-phenylpropanamide | | 382 | ++++ | +++ |
| 26 | 3-(3-amino-7-o-tolylnaphthalen-2-yl)-N-(2-methoxybutyl)propanamide | | 392 | ++++ | ++ |
| 27 | N-(2-fluorobenzyl)-3-(3-amino-7-o-tolylnaphthalen-2-yl)propanamide | | 414 | ++++ | ++ |
| 28 | 3-(3-amino-7-o-tolylnaphthalen-2-yl)-N-(2-fluorophenyl)propanamide | | 400 | +++ | ++ |
| 29 | 3-(3-amino-7-o-tolylnaphthalen-2-yl)-N-(2-methoxy-2-methylpropyl)propanamide | | 392 | +++ | ++ |
| 30 | 3-(3-amino-7-o-tolylnaphthalen-2-yl)-N-(1-phenylethyl)propanamide | | 410 | ++++ | ++ |
| 31 | 3-(3-amino-7-o-tolylnaphthalen-2-yl)-N-((R)-1-cyclohexylethyl)propanamide | | 416 | ++++ | + |
| 32 | 2-((2-amino-6-o-tolylquinolin-3-yl)methyl)-N-(cyclohexylmethyl)pentanamide | | 444 | ++++ | |
| 33 | 2-((2-amino-6-o-tolylquinolin-3-yl)methyl)-N-(cyclohexylmethyl)-N-methylpentanamide | | 444 | ++++ | + |
| 2 | 3-(2-amino-6-(thiazol-4-yl)quinolin-3-yl)-N-(cyclohexylmethyl)propanamide | | 395 | ++ | + |
| 33 | 3-(2-amino-6-(3-methylpyridin-2-yl)quinolin-3-yl)-N-(cyclohexylmethyl)propanamide | | 403 | ++++ | ++ |
| 34 | 3-(2-amino-6-(pyridin-3-yl)quinolin-3-yl)-N-(cyclohexylmethyl)propanamide | | 389 | _++ | ++ |
| 35 | 3-(3-amino-7-o-tolylnaphthalen-2-yl)-N-((S)-1-cyclohexylethyl)propanamide | | 416 | ++++ | + |
| 36 | 3-(3-amino-7-o-tolylnaphthalen-2-yl)-N-(pyridin-2-ylmethyl)propanamide | | 397 | ++++ | ++ |
| 37 | 3-(3-amino-7-o-tolylnaphthalen-2-yl)-N-(pyridin-3-ylmethyl)propanamide | | 397 | ++++ | ++ |
| 38 | 3-(2-amino-6-(2-methylpyridin-3-yl)quinolin-3-yl)-N-(cyclohexylmethyl)propanamide | | 403 | +++ | + |
| 39 | 3-(2-amino-6-o-tolylquinolin-3-yl)-N-(1-methylpiperidin-3-yl)propanamide | | 403 | ++ | ++ |
| 40 | 3-(2-amino-6-o-tolylquinolin-3-yl)-N-((tetrahydro-2H-pyran-2-yl)methyl)propanamide | | 404 | ++++ | ++ |
| 3 | 3-(2-amino-6-(2-chlorophenyl)quinolin-3-yl)-N-(cyclohexylmethyl)propanamide | | 422 | ++++ | ++ |
| 41 | 3-(2-amino-6-(2-cyanophenyl)quinolin-3-yl)-N-(cyclohexylmethyl)propanamide | | 413 | ++++ | ++ |
| 42 | 3-(2-amino-6-(2-fluorophenyl)quinolin-3-yl)-N-(cyclohexylmethyl)propanamide | | 406 | ++++ | + |
| 43 | 3-(2-amino-6-(3-fluorophenyl)quinolin-3-yl)-N-(cyclohexylmethyl)propanamide | | 406 | +++ | ++ |
| 44 | 3-(2-amino-6-(2-methoxyphenyl)quinolin-3-yl)-N-(cyclohexylmethyl)propanamide | | 418 | ++++ | ++ |
| 45 | 3-(2-amino-6-phenylquinolin-3-yl)-N-(cyclohexylmethyl)propanamide | | 388 | +++ | + |
| 46 | 3-(2-amino-6-(4-methylpyridin-3-yl)quinolin-3-yl)-N-(cyclohexylmethyl)propanamide | | 403 | ++ | + |
| 47 | 3-(2-amino-6-o-tolylquinolin-3-yl)-N-((R)-1-cyclohexylethyl)-2-methylpropanamide | | 430 | ++++ | ++ |
| 48 | N-(3-(2-amino-6-o-tolylquinolin-3-yl)propyl)cyclohexanecarboxamide | | 402 | ++++ | ++ |

TABLE 1-continued

| Ex. No. | Compound Name | Method | Observed MS | BACE 1 FRET assay (uM) | HEK cell assay (uM) |
|---|---|---|---|---|---|
| 49 | 3-(2-amino-6-(2-ethylphenyl)quinolin-3-yl)-N-(cyclohexylmethyl)propanamide | | 416 | ++++ | ++ |
| 50 | 2-((2-amino-6-o-tolylquinolin-3-yl)methyl)-N-(2-fluorophenyl)butanamide | | 428 | ++++ | + |
| 51 | 3-(2-amino-6-o-tolylquinolin-3-yl)-2-methyl-N-phenylpropanamide | | 396 | ++++ | ++ |
| 52 | 3-(2-amino-6-o-tolylquinolin-3-yl)-N-benzyl-2-methylpropanamide | | 410 | ++++ | ++ |
| 53 | 3-(2-amino-6-o-tolylquinolin-3-yl)-N-(2-fluoro-4-methylphenyl)propanamide | | 414 | ++ | ++ |
| 54 | 3-(2-amino-6-o-tolylquinolin-3-yl)-N-((1-methyl-1H-pyrazol-3-yl)methyl)propanamide | | 400 | ++ | + |
| 55 | 3-(3-amino-7-o-tolylnaphthalen-2-yl)-N-((R)-1-(2-fluorophenyl)ethyl)propanamide | | 428 | ++++ | ++ |
| 56 | 3-(3-amino-7-o-tolylnaphthalen-2-yl)-N-(1-(pyridin-2-yl)ethyl)propanamide | | 411 | ++++ | ++ |
| 57 | 3-(3-amino-7-o-tolylnaphthalen-2-yl)-N-(2,3-dihydro-1H-inden-1-yl)propanamide | | 422 | ++++ | ++ |
| 58 | 3-(2-amino-6-o-tolylquinolin-3-yl)-N-((3-methyloxetan-3-yl)methyl)propanamide | | 390 | ++ | + |
| 59 | 3-(2-amino-6-o-tolylquinolin-3-yl)-N-((1-ethyl-1H-pyrazol-3-yl)methyl)propanamide | | 414 | ++++ | ++ |
| 60 | 2-((2-amino-6-o-tolylquinolin-3-yl)methyl)-N-(cyclohexylmethyl)butanamide | | 430 | ++++ | + |
| 5 | 3-(2-amino-6-(3-methylpyridin-2-yl)quinolin-3-yl)-N-(3,3-dimethylbutyl)-2-methylpropanamide | | 405 | ++++ | +++ |
| 61 | N-(2-methoxybenzyl)-3-(3-amino-7-o-tolylnaphthalen-2-yl)propanamide | | 426 | ++ | + |
| 62 | 3-(2-amino-6-o-tolylquinolin-3-yl)-N-((1R,2R)-2-methoxycyclopentyl)propanamide | | 404 | ++++ | ++ |
| 63 | 3-(2-amino-6-o-tolylquinolin-3-yl)-N-(thiazol-2-ylmethyl)propanamide | | 403 | ++++ | ++ |
| 64 | 3-(2-amino-6-o-tolylquinolin-3-yl)-2-methyl-N-(1-methylpiperidin-3-yl)propanamide | | 417 | ++++ | ++++ |
| 65 | 3-(2-amino-6-(4-fluorophenyl)quinolin-3-yl)-N-(cyclohexylmethyl)propanamide | | 406 | ++++ | + |
| 66 | 2-((2-amino-6-o-tolylquinolin-3-yl)methyl)-N-(cyclohexylmethyl)-3-methylbutanamide | | 444 | ++++ | ++ |
| 6 | 3-(2-amino-6-o-tolylquinolin-3-yl)-N-(cyclohexylmethyl)butanamide | | 416 | ++++ | + |
| 67 | 3-(2-amino-6-o-tolylquinolin-3-yl)-N-(oxazol-2-ylmethyl)propanamide | | 387 | ++++ | ++ |
| 68 | N-(2-fluoro-4-methylbenzyl)-3-(2-amino-6-o-tolylquinolin-3-yl)propanamide | | 428 | ++ | + |
| 7 | 3-(2-amino-6-(2-methylcyclopropyl)quinolin-3-yl)-N-(3,3-dimethylbutyl)-2-methylpropanamide | | 368 | ++++ | ++ |
| 69 | 3-(3-amino-7-o-tolylnaphthalen-2-yl)-2-methyl-N-(pyridin-3-ylmethyl)propanamide | | 411 | ++++ | +++ |
| 70 | 3-(3-amino-7-o-tolylnaphthalen-2-yl)-N-(1-(2-methoxyphenyl)ethyl)-2-methylpropanamide | | 454 | ++++ | ++ |
| 71 | 3-(2-amino-6-o-tolylquinolin-3-yl)-N-(cyclohexylmethyl)-2-methoxypropanamide | | 432 | ++++ | ++ |
| 72 | 3-(2-amino-6-(2-isopropylphenyl)quinolin-3-yl)-N-(cyclohexylmethyl)propanamide | | 430 | ++++ | + |
| 7 | 3-(2-amino-6-(2-methylcyclopropyl)quinolin-3-yl)-N-(3,3-dimethylbutyl)-2-methylpropanamide | | 368 | ++++ | ++ |
| 73 | 3-(3-amino-7-o-tolylnaphthalen-2-yl)-N-(6,7-dihydro-5H-cyclopenta[b]pyridin-7-yl)-2-methylpropanamide | | 437 | ++++ | ++ |
| 4 | 3-(2-amino-6-(2-methyl-1H-imidazol-1-yl)quinolin-3-yl)-N-(cyclohexylmethyl)propanamide | | 392 | + | + |
| 74 | (R)-3-(2-amino-6-o-tolylquinolin-3-yl)-N-((R)-1-(2-methoxyphenyl)ethyl)-2-methylpropanamide | | 454 | ++ | + |
| 75 | (S)-3-(2-amino-6-o-tolylquinolin-3-yl)-N-((R)-1-(2-methoxyphenyl)ethyl)-2-methylpropanamide | | 454 | ++++ | ++ |
| 76 | 3-(2-amino-6-o-tolylquinolin-3-yl)-N-((R)-1-(2-methoxyphenyl)ethyl)-2-methylpropanamide | | 454 | ++++ | ++ |
| 77 | 3-(2-amino-6-o-tolylquinolin-3-yl)-N-((R)-1-(2-(difluoromethoxy)phenyl)ethyl)-2-methylpropanamide | | 490 | ++++ | ++ |
| 78 | 3-(2-amino-6-o-tolylquinolin-3-yl)-N-((R)-1-(pyridin-3-yl)ethyl)propanamide | | 411 | ++ | + |
| 79 | 3-(2-amino-6-(3-methylpyridin-2-yl)quinolin-3-yl)-N-((R)-1-(pyridin-3-yl)ethyl)propanamide | | 412 | | |

TABLE 1-continued

| Ex. No. | Compound Name | Method | Observed MS | BACE 1 FRET assay (uM) | HEK cell assay (uM) |
|---|---|---|---|---|---|
| 80 | (R)-3-(2-amino-6-o-tolylquinolin-3-yl)-2-methyl-N-(pyrazin-2-ylmethyl)propanamide | V | 412 | ++++ | ++++ |
| 81 | (R)-3-(2-amino-6-o-tolylquinolin-3-yl)-2-methyl-N-(pyridazin-3-ylmethyl)propanamide | V | 412 | ++++ | +++ |
| 82 | 3-(2-amino-6-(3-chloropyridin-2-yl)quinolin-3-yl)-2-methyl-N-(((S)-tetrahydro-2H-pyran-2-yl)methyl)propanamide | V | 439 | +++ | ++ |
| 83 | 3-(2-amino-6-(3-chloropyridin-2-yl)quinolin-3-yl)-2-methyl-N-(((R)-tetrahydro-2H-pyran-2-yl)methyl)propanamide | V | 439 | ++++ | ++ |
| 84 | (R)-3-(2-amino-6-o-tolylquinolin-3-yl)-2-methyl-N-(pyrimidin-4-ylmethyl)propanamide | V | 412 | ++++ | ++++ |
| 85 | (R)-3-(2-amino-6-o-tolylquinolin-3-yl)-2-methyl-N-(pyrimidin-2-ylmethyl)propanamide | V | 412 | ++++ | ++++ |
| 86 | 3-(2-amino-6-(3-methylpyridin-2-yl)quinolin-3-yl)-2-methyl-N-(((R)-tetrahydro-2H-pyran-3-yl)methyl)propanamide | V | 419 | ++++ | ++++ |
| 87 | (R)-3-(2-amino-6-o-tolylquinolin-3-yl)-2-methyl-N-((tetrahydro-2H-pyran-4-yl)methyl)propanamide | V | 418 | ++++ | ++++ |
| 88 | 3-(2-amino-6-(3-methylpyridin-2-yl)quinolin-3-yl)-2-methyl-N-((tetrahydro-2H-pyran-4-yl)methyl)propanamide | V | 419 | ++++ | +++ |
| 89 | 3-(2-amino-6-(3-methylpyridin-2-yl)quinolin-3-yl)-2-methyl-N-(((S)-tetrahydro-2H-pyran-3-yl)methyl)propanamide | V | 419 | ++++ | +++ |
| 90 | 3-(2-amino-6-o-tolylquinolin-3-yl)-N-(3,3-dimethylbutyl)-2-methylpropanamide | V | 404 | ++++ | ++++ |
| 91 | 3-(2-amino-6-o-tolylquinolin-3-yl)-2-methyl-N-((tetrahydrofuran-3-yl)methyl)propanamide | V | 404 | ++++ | ++ |
| 92 | 3-(2-amino-6-o-tolylquinolin-3-yl)-2-methyl-N-((tetrahydro-2H-pyran-3-yl)methyl)propanamide | V | 418 | ++++ | ++++ |
| 93 | 3-(2-amino-6-o-tolylquinolin-3-yl)-2-methyl-N-(thiazol-5-ylmethyl)propanamide | V | 417 | ++++ | ++++ |
| 94 | 3-(2-amino-6-o-tolylquinolin-3-yl)-2-methyl-N-((1-methyl-1H-pyrazol-4-yl)methyl)propanamide | V | 414 | ++++ | ++ |
| 95 | 3-(2-amino-7-methyl-6-(2-methylphenyl)-3-quinolinyl)-N-(cyclohexylmethyl)propanamide | VIII | 416 | ++++ | + |
| 96 | 3-(2-amino-7-fluoro-6-(2-methylphenyl)-3-quinolinyl)-N-(cyclohexylmethyl)propanamide | VIII | 420 | ++++ | ++ |
| 97 | 3-(2-amino-7-fluoro-6-(3-methyl-2-pyridinyl)-3-quinolinyl)-2-methyl-N-(tetrahydro-2H-pyran-4-ylmethyl)propanamide | VIII | 437 | ++++ | ++ |
| 98 | 3-(2-amino-7-fluoro-6-(3-methyl-2-pyridinyl)-3-quinolinyl)-N-(3,3-dimethylbutyl)-2-methylpropanamide | VIII | 423 | ++++ | ++++ |
| 99 | 3-(6-(3-chloropyridin-2-yl)quinolin-3-yl)-N-((4,4-difluorocyclohexyl)methyl)-2-methylpropanamide | V | 473 | ++++ | ++ |
| 100 | N-(4-fluoro-4-methylpentan-2-yl)-2-methyl-3-(6-(3-methylpyridin-2-yl)quinolin-3-yl)propanamide | V | 423 | +++ | ++ |
| 101 | N-(3-fluoro-3-methylbutyl)-2-methyl-3-(6-(3-methylpyridin-2-yl)quinolin-3-yl)propanamide | V | 409 | ++++ | ++++ |
| 102 | 3-(2-amino-6-(3-methylpyridin-2-yl)quinolin-3-yl)-2-methyl-N-(2-(1-methylcyclopropyl)ethyl)propanamide | V | 403 | ++++ | ++++ |
| 103 | 3-(2-amino-6-(2-butoxyphenyl)quinolin-3-yl)-N-(cyclohexylmethyl)-2-methylpropanamide | V | 474 | ++++ | ++++ |
| 104 | 3-(2-amino-6-o-tolylquinolin-3-yl)-N-(1-(2-methoxyphenyl)ethyl)-2-methylpropanamide | V | 454 | ++++ | ++ |
| 105 | 3-(2-amino-6-o-tolylquinolin-3-yl)-N-(1-(2-methoxyphenyl)ethyl)propanamide | I | 440 | ++++ | ++ |
| 106 | 3-(2-amino-6-o-tolylquinolin-3-yl)-N-(1-(2-fluorophenyl)ethyl)-2-methylpropanamide | V | 442 | ++++ | + |
| 107 | 3-(2-amino-6-(2-fluoro-6-methylpyridin-3-yl)quinolin-3-yl)-N-(cyclohexylmethyl)-2-methylpropanamide | V | 435 | ++ | ++ |
| 108 | 3-(2-amino-6-(2-((dimethylamino)methyl)phenyl)quinolin-3-yl)-N-(cyclohexylmethyl)-2-methylpropanamide | V | 459 | ++++ | ++++ |
| 109 | 3-(2-amino-6-(3-methylpyridin-2-yl)quinolin-3-yl)-N-isopentyl-2-methylpropanamide | V | 391 | ++++ | ++++ |
| 110 | 3-(2-amino-6-(3-methylpyridin-2-yl)quinolin-3-yl)-2-methyl-N-(2,2,2-trifluoroethyl)propanamide | V | 403 | +++ | +++ |
| 111 | 3-(2-amino-6-(3-methylpyridin-2-yl)quinolin-3-yl)-N-(2-cyclopropylethyl)-2-methylpropanamide | V | 389 | ++++ | ++ |

TABLE 1-continued

| Ex. No. | Compound Name | Method | Observed MS | BACE 1 FRET assay (uM) | HEK cell assay (uM) |
|---|---|---|---|---|---|
| 112 | 3-(2-amino-6-(3-methylpyridin-2-yl)quinolin-3-yl)-2-methyl-N-(3,3,3-trifluoropropyl)propanamide | V | 417 | ++++ | +++ |
| 113 | 3-(2-amino-6-(3-methylpyridin-2-yl)quinolin-3-yl)-2-methyl-N-(2-(tetrahydrofuran-2-yl)ethyl)propanamide | V | 419 | +++ | ++ |
| 114 | 3-(2-amino-6-(3-methylpyridin-2-yl)quinolin-3-yl)-2-methyl-N-((R)-1,1,1-trifluoropropan-2-yl)propanamide | V | 417 | ++ | ++ |
| 115 | 3-(2-amino-6-o-tolylquinolin-3-yl)-N-(2-cyclopropylethyl)propanamide | I | 374 | ++++ | ++ |
| 116 | 3-(2-amino-6-(3-chloropyridin-2-yl)quinolin-3-yl)-2-methyl-N-(3,3,3-trifluoropropyl)propanamide | V | 436.9 | ++ | + |
| 117 | 3-(2-amino-6-(3-methylpyridin-2-yl)quinolin-3-yl)-N-((4,4-difluorocyclohexyl)methyl)-2-methylpropanamide | V | 453 | ++++ | +++ |
| 118 | 3-(2-amino-6-(3-methylpyridin-2-yl)quinolin-3-yl)-1-(2-ethylazetidin-1-yl)-2-methylpropan-1-one | V | 389 | + | + |
| 119 | 3-(2-amino-6-(2-(methoxymethyl)cyclopropyl)quinolin-3-yl)-N-(3,3-dimethylbutyl)-2-methylpropanamide | VIII | 398 | + | + |
| 120 | 3-(2-amino-6-(2-ethylcyclopropyl)quinolin-3-yl)-N-(3,3-dimethylbutyl)-2-methylpropanamide | VIII | 382 | +++ | + |
| 121 | 3-(2-amino-6-((1S,2R)-2-methylcyclopropyl)quinolin-3-yl)-N-(3,3-dimethylbutyl)-2-methylpropanamide | VIII | 368 | +++ | + |
| 122 | 3-(2-amino-6-(pyridin-2-yl)quinolin-3-yl)-N-(3,3-dimethylbutyl)-2-methylpropanamide | VIII | 391 | ++++ | +++ |
| 123 | 3-(2-amino-6-(3-(2-morpholinoethyl)pyridin-2-yl)quinolin-3-yl)-N-(3,3-dimethylbutyl)-2-methylpropanamide | V | 504 | ++++ | ++++ |
| 124 | 3-(2-amino-6-(3-(2-(4-methylpiperazin-1-yl)ethyl)pyridin-2-yl)quinolin-3-yl)-N-(3,3-dimethylbutyl)-2-methylpropanamide | V | 517 | +++ | ++++ |
| 125 | 3-(2-amino-6-(3-(2-(pyrrolidin-1-yl)ethyl)pyridin-2-yl)quinolin-3-yl)-N-(3,3-dimethylbutyl)-2-methylpropanamide | V | 488 | ++++ | ++++ |
| 126 | (R)-3-(2-amino-6-(3-methylpyridin-2-yl)quinolin-3-yl)-N-(3,3-dimethylbutyl)-2-methylpropanamide | V | 405 | ++++ | ++++ |
| 127 | 3-(2-amino-6-(3-(2-(dimethylamino)ethyl)pyridin-2-yl)quinolin-3-yl)-N-(3,3-dimethylbutyl)-2-methylpropanamide | V | 462 | ++++ | ++++ |
| 128 | (R)-3-(2-amino-6-(3-chloropyridin-2-yl)quinolin-3-yl)-N-(3,3-dimethylbutyl)-2-methylpropanamide | V | 425 | ++++ | ++++ |
| 129 | 3-(2-amino-6-o-tolylquinolin-3-yl)-N-((R)-1-(2-methoxyphenyl)ethyl)-2-methylpropanamide | V | 454 | ++++ | ++ |
| 130 | 3-(2-amino-6-o-tolylquinolin-3-yl)-N-((R)-1-(2-(difluoromethoxy)phenyl)ethyl)-2-methylpropanamide | V | 490 | ++++ | ++ |
| 131 | (R)-3-(2-amino-6-o-tolylquinolin-3-yl)-N-(1-(pyridin-3-yl)ethyl)propanamide | I | 411 | ++++ | ++ |
| 132 | (R)-3-(2-amino-6-(3-methylpyridin-2-yl)quinolin-3-yl)-N-(1-(pyridin-3-yl)ethyl)propanamide | I | 412 | ++ | + |
| 133 | (R)-3-(2-amino-6-(3-methylpyridin-2-yl)quinolin-3-yl)-N-(1-(2-(difluoromethoxy)phenyl)ethyl)propanamide | I | 477 | ++ | + |
| 134 | 3-(2-amino-6-o-tolylquinolin-3-yl)-1-(3,3-difluoropyrrolidin-1-yl)propan-1-one | I | 396 | ++ | + |
| 135 | 3-(2-amino-6-o-tolyl-1,7-naphthyridin-3-yl)-N-(3,3-dimethylbutyl)propanamide | IX | 391 | ++++ | + |
| 136 | 3-(2-amino-6-o-tolyl-1,7-naphthyridin-3-yl)-N-benzyl-2-methylpropanamide | IX | 411 | ++++ | ++ |
| 137 | 3-(2-amino-6-o-tolyl-1,7-naphthyridin-3-yl)-2-methyl-N-(3,3,3-trifluoropropyl)propanamide | IX | 417 | ++++ | + |
| 138 | 3-(2-amino-6-o-tolyl-1,7-naphthyridin-3-yl)-N-(3,3-dimethylbutyl)-2-methylpropanamide | IX | 405 | ++++ | ++++ |

TABLE 1-continued

| Ex. No. | Compound Name | Method | Observed MS | BACE 1 FRET assay (uM) | HEK cell assay (uM) |
|---|---|---|---|---|---|
| 139 | 3-(2-amino-6-o-tolylquinolin-3-yl)-N-(pyridazin-4-ylmethyl)propanamide | I | 398 | ++ | + |
| 140 | 3-(3-amino-7-(2-methylphenyl)-2-quinoxalinyl)-N-(cyclohexylmethyl)propanamide | X | 403 | ++++ | ++ |
| 141 | 3-(2-amino-6-(2-methylphenyl)-3-quinolinyl)-N-(3-hydroxy-3-methylbutyl)propanamide | I | 392 | ++++ | +++ |
| 142 | 3-(2-amino-6-(2-cyanophenyl)-3-quinolinyl)-N-(2,2-dimethyltetrahydro-2H-pyran-4-yl)-2-methylpropanamide | V | 444 | ++++ | ++++ |
| 143 | 3-(6-(2-acetylphenyl)-2-amino-3-quinolinyl)-N-(2,2-dimethyltetrahydro-2H-pyran-4-yl)-2-methylpropanamide | V | 461 | ++++ | ++++ |
| 144 | 3-(2-amino-6-(2-methylphenyl)-3-quinolinyl)-N-(2-hydroxy-2-methylpropyl)propanamide | I | 379 | ++ | ++ |
| 12 | (2R)-3-(2-amino-6-o-tolylquinolin-3-yl)-N-(cis-2,6-dimethyltetrahydro-2H-pyran-4-yl)-2-methylpropanamide | V | 433 | ++++ | ++++ |
| 145 | 3-(2-amino-6-(2-methyl-6-(1-pyrrolidinylcarbonyl)phenyl)-3-quinolinyl)-N-(2,2-dimethyltetrahydro-2H-pyran-4-yl)-2-methylpropanamide | V | 553 | ++++ | ++++ |
| 146 | 3-(2-amino-6-(2-((2-methoxyphenyl)carbonyl)phenyl)-3-quinolinyl)-N-(2,2-dimethyltetrahydro-2H-pyran-4-yl)-2-methylpropanamide | V | 553 | ++++ | ++++ |
| 147 | 3-(2-amino-6-(2-(cyclohexylcarbonyl)phenyl)-3-quinolinyl)-N-(2,2-dimethyltetrahydro-2H-pyran-4-yl)-2-methylpropanamide | V | 529 | ++++ | ++++ |
| 148 | 3-(2-Amino-6-(2-methyl-6-(pyrrolidine-1-carbonyl)phenyl)quinolin-3-yl)-N,2-dimethylpropanamide | V | 431 | ++++ | ++++ |
| 149 | 3-(2-amino-6-(2-methyl-6-(pyrrolidine-1-carbonyl)phenyl)quinolin-3-yl)-2-methyl-N-(pyridin-2-ylmethyl)propanamide | V | 508 | ++++ | ++++ |
| 150 | 3-(2-amino-6-(2-methyl-6-(pyrrolidine-1-carbonyl)phenyl)quinolin-3-yl)-N-cyclopropyl-2-methylpropanamide | V | 457 | ++++ | ++++ |
| 151 | 3-(2-amino-6-(2-methyl-6-(pyrrolidine-1-carbonyl)phenyl)quinolin-3-yl)-N-benzyl-2-methylpropanamide | V | 507 | ++++ | ++++ |
| 152 | 3-(6-(2-acetylphenyl)-2-aminoquinolin-3-yl)-2-methyl-N-phenylpropanamide | V | 424 | ++++ | ++++ |
| 153 | 3-(2-amino-6-(2-methyl-6-(pyrrolidine-1-carbonyl)phenyl)quinolin-3-yl)-2-methyl-N-phenylpropanamide | V | 493 | ++++ | ++++ |
| 154 | 3-(6-(2-acetylphenyl)-2-aminoquinolin-3-yl)-N,2-dimethylpropanamide | V | 362 | + | + |
| 155 | (S) 3-(2-amino-6-(2-methyl-6-(pyrrolidine-1-carbonyl)phenyl)quinolin-3-yl)-N,2-dimethylpropanamide | V | 431 | ++ | ++ |
| 9 | (R)-3-(2-amino-6-(2-methyl-6-(pyrrolidine-1-carbonyl)phenyl)quinolin-3-yl)-N,2-dimethylpropanamide | V | 431 | ++++ | ++++ |
| 156 | 3-(6-(2-acetylphenyl)-2-aminoquinolin-3-yl)-N-(3,3-dimethylbutyl)-2-methylpropanamide | V | 432 | ++++ | ++++ |
| 157 | 3-(2-amino-6-(2-(cyclohexanecarbonyl)phenyl)quinolin-3-yl)-N,2-dimethylpropanamide | V | 430 | ++++ | +++ |
| 158 | (2R)-3-(2-amino-6-o-tolylquinolin-3-yl)-2-methyl-N-(2-methyltetrahydro-2H-pyran-4-yl)propanamide | V | 418 | ++++ | ++++ |
| 159 | 3-(2-amino-6-(2,3-dichlorophenyl)quinolin-3-yl)-N-(2,2-dimethyltetrahydro-2H-pyran-4-yl)-2-methylpropanamide | V | 486 | ++++ | ++++ |
| 160 | (R)-3-(2-amino-6-o-tolylquinolin-3-yl)-N-(cis-2-ethynyltetrahydro-2H-pyran-4-yl)-2-methylpropanamide | V | 428 | ++++ | ++++ |
| 161 | 3-(2-amino-6-(2,3-dichlorophenyl)quinolin-3-yl)-2-methyl-N-(5-oxaspiro[3.5]nonan-8-yl)propanamide | V | 498 | ++++ | ++++ |

TABLE 1-continued

| Ex. No. | Compound Name | Method | Observed MS | BACE 1 FRET assay (uM) | HEK cell assay (uM) |
|---|---|---|---|---|---|
| 162 | (2R)-3-(2-amino-6-(2-methylphenyl)-3-quinolinyl)-N-(3,3-dimethylcyclohexyl)-2-methylpropanamide | V | 430.2 | ++++ | ++++ |
| 10 | 3-(2-amino-6-(2-methylphenyl)-3-quinolinyl)-N-(3,3-dimethylcyclohexyl)propanamide | I | 416.2 | ++++ | ++++ |
| 163 | 3-(2-amino-6-(2-methylphenyl)-3-quinolinyl)-N-(-2,2-dimethyltetrahydro-2H-pyran-4-yl)propanamide | I | 418.2 | ++++ | ++++ |
| 164 | (2R)-3-(2-amino-6-o-tolylquinolin-3-yl)-N-(2,2-dimethyltetrahydro-2H-pyran-4-yl)-2-methylpropanamide | V | 432.1 | ++++ | ++++ |
| 165 | 3-(2-amino-6-(2-(1-pyrrolidinylcarbonyl)phenyl)-3-quinolinyl)-N-(3,3-dimethylbutyl)propanamide | II | 473.2 | ++++ | ++ |
| 166 | 3-(2-amino-6-(2-chloro-4-fluorophenyl)-3-quinolinyl)-N-(2,2-dimethyltetrahydro-2H-pyran-4-yl)-2-methylpropanamide | V | 470.1 | ++++ | ++ |
| 167 | 3-(2-amino-6-(4-fluorophenyl)-3-quinolinyl)-N-(2,2-dimethyltetrahydro-2H-pyran-4-yl)-2-methylpropanamide | V | 436.1 | ++ | + |
| 168 | 3-(2-amino-6-(4-chlorophenyl)-3-quinolinyl)-N-(2,2-dimethyltetrahydro-2H-pyran-4-yl)-2-methylpropanamide | V | 452 | ++++ | ++++ |
| 169 | 3-(2-amino-6-(3-chlorophenyl)-3-quinolinyl)-N-(2,2-dimethyltetrahydro-2H-pyran-4-yl)-2-methylpropanamide | V | 452 | ++++ | ++++ |
| 170 | (2R)-3-(2-amino-6-(2-methylphenyl)-3-quinolinyl)-2-methyl-N-(5-oxaspiro[35]non-8-yl)propanamide | V | 444.2 | ++++ | ++++ |
| 11 | 3-(2-amino-6-(3-chlorophenyl)-3-quinolinyl)-2-methyl-N-(5-oxaspiro[3,5]non-8-yl)propanamide | V | 464.1 | ++++ | ++++ |
| 171 | 3-(2-amino-6-(2-chlorophenyl)-3-quinolinyl)-2-methyl-N-(5-oxaspiro[3,5]non-8-yl)propanamide | V | 464.1 | ++++ | ++++ |

The present invention also provides methods for making compounds of Formulas I, I-A and I-B. In another embodiment of the invention, there is provided a method of making a compound of Formula I, the method comprising the step of (a) reacting a compound 17

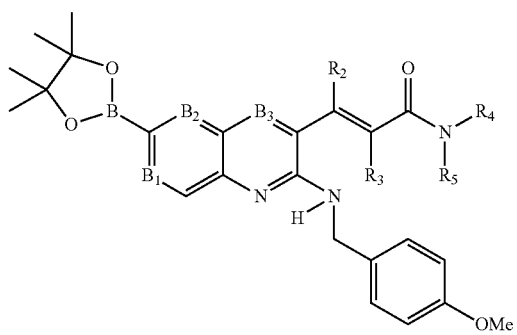

wherein $B^1$, $B^2$, $B^3$, $R^2$, $R^3$, $R^4$ and $R^5$ of Formula I are as defined herein, with a compound having the structure wherein ring A, $R^1$ and m are as defined herein to make a compound 18 of the formula

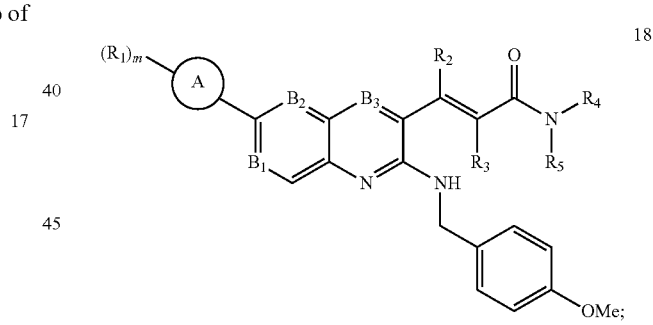

(b) reducing compound 18 to make a compound 19 of formula

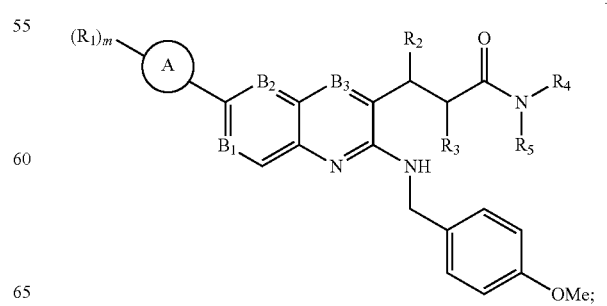

and (c) removing the

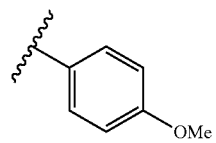 [SMILES: *c1ccc(OC)cc1]

protecting group from compound 19, to make a compound of Formula I.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, CHCl$_3$ and CCl$_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, H$_2$SO$_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I, I-A and I-B, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

Biological Evaluation

The compounds of the invention may be modified by appending appropriate functionalities to enhance selective biological properties. Surprisingly, the compounds of the present invention exhibit improved pharmacokinetics and pharmacodynamics, which relate, directly and indirectly, to the ability of the compound to be effective for its intended use. For example, the compounds have been found to possess favorable clearance and efflux properties, which readily lend themselves to projecting in-vivo PK and PD properties, which in turn assist in projection of therapeutic target coverage for the compounds and projected efficacious dosages via in-vivo absorption, distribution, metabolism and excretion properties. Increased biological penetration into a given biological compartment (e.g., blood, lymphatic system, central nervous system), increase oral availability, increase solubility to allow administration by injection and alter clearance, metabolism and/or rate of excretion are important factors for discovering which compound may be a useful drug and which may not.

Although the pharmacological properties of the compounds of the invention (Formulas I-III) vary with structural change, in general, activity possessed by compounds of Formulas I-III may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (Fluorescence Resonance Energy Transfer) Assay (Enzyme Assay Data in Table 1)

The assay buffer used in this screen is 0.05 M acetate, pH 4.2, 10% DMSO final, 100 uM genapol (which is a nonionic detergent, below its Critical Micelle Concentration). The Beta Secretase enzyme (0.2 nM) is pre-incubated for one hour with inhibitors, typically in about 1 uL of DMSO according to a serial dilution, are added thereto. The assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Of the compounds tested, the in-vitro BACE FRET enzyme data for each of Examples 1-171, where available at the time of filing this application, is provided in Table 1. Data key for the in-vitro BACE FRET assay is as follows:

"+" means the compound example has an $IC_{50}$ value of >5.0 uM;

"++" means the compound example has an $IC_{50}$ value in the range from 1.0 uM-5.0 uM;

"+++" means the compound example has an $IC_{50}$ value in the range from 500 nM-1.0 uM;

"++++" means the compound example has an $IC_{50}$ value in the range less than 500 nM.

A majority of the exemplary compounds tested had $IC_{50}$'s for the enzyme BACE of less than 50 nM. For instance, example numbers 81, 84, 87, 90-93, 96, 98, 103, 106, 126, 128-130, 135, 136, 138, 12, 145-151, 153, 9, 156, 10, 158-164, 11 and 169-171 each exhibited an $IC_{50}$ value of less than 50 nM in the FRET BACE enzyme assay.

In Vitro BACE Cell-Based Assay:

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal concentration for the pAb40 antibody was 3 μg/ml in Superblock/TBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Of the compounds tested, the cell based assay data for each of Examples 1-171 is provided in Table 1. Data key for the cell-based assay is as follows:

"+" means the compound example has an $IC_{50}$ value of >5.0 uM;

"++" means the compound example has an $IC_{50}$ value in the range from 1.0 uM-5.0 uM;

"+++" means the compound example has an $IC_{50}$ value in the range from 500 nM-1.0 uM;

"++++" means the compound example has an $IC_{50}$ value in the range less than 500 nM.

A majority of the exemplary compounds tested had $IC_{50}$'s for the enzyme BACE of less than 100 nM. For instance, example numbers 108, 123-128, 12, 145-148, 150-151, 153, 9, 163 and 169 each exhibited an $IC_{50}$ value of less than 100 nM in the BACE cell-based in-vitro assay.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry*, 76, 173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics*, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of Abeta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, Abeta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2
IV: 5% EtOH, 45% Propylene glycol in 5% Dextrose The compounds of the invention may be shown to reduce the formation and/or deposition of A-beta peptide in the brain or in the cerebrospinal fluid of a mouse or rat.

Indications

Accordingly, compounds of the invention are useful for, but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide and/or plaque on the brain. In one embodiment of the invention, there is provided a method of treating a disorder related to a beta-secretase enzyme in a subject, the method comprising administering to the subject an effective dosage amount of a compound of Formulas I, I-A and I-B. In another embodiment, there is provided a method of reducing production of amyloid beta, and of reducing plaque formation. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I, I-A and I-B. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients and the like as described herein. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the compound is administered by administering a portion of the composition. Alternatively, a pharmaceutical composition in which two or more unit dosages, such as in tablets, capsules and the like, are required to administer an effective amount of the compound may be administered in less than an effective amount for one or more periods of time, for example to ascertain the effective dose for an individual subject, to desensitize an individual subject to potential side effects, to permit effective dosing readjustment or depletion of one or more other therapeutics administered to an individual subject, and/or the like.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I, I-A and I-B with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I, I-A and I-B with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I, I-A and I-B may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of Formula I:

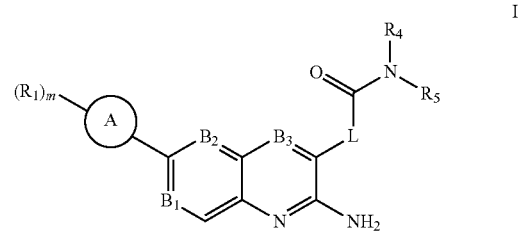

or a stereoisomer or pharmaceutically acceptable salt thereof, wherein

A is a phenyl, pyridine, pyrimidine, triazine or thiophene ring;

each of $B^1$, $B^2$ and $B^3$, independently, is —CF, —CCH$_3$ or CH;

L is —CR$^2$R$^2$—(CR$^3$R$^3$)$_o$— wherein
  each R$^2$, independently, is H, C$_{1-3}$alkyl or halo; and
  each R$^3$, independently, is H, C$_{1-6}$alkyl, C$_{3-6}$cycloalkyl, —OH, —OC$_{1-4}$alkyl, halo, haloalkyl, CN, —NH$_2$ or —NHC$_{1-6}$alkyl and o is 1;

each R$^1$, independently, is F, Cl, Br, CF$_3$, OCF$_3$, C$_{1-6}$-alkyl, CN, OH, —OC$_{1-6}$-alkyl, C$_{1-6}$-alkenyl, C$_{1-6}$-alkynyl, —S(O)$_n$C$_{1-6}$-alkyl, —NH$_2$, CN, —NHC$_{1-6}$-alkyl, —C(O)C$_{1-6}$-alkyl, —C(O)-aryl, —C(O)-heteroaryl, —C(O)-heterocyclyl, —C(O)—C$_{3-8}$-cycloalkyl or —C(O)NR$^a$R$^b$ wherein R$^a$ is H or C$_{1-6}$alkyl and R$^b$ is R$^6$;
alternatively, R$^a$ and R$^b$ taken together with the nitrogen atom to which they are attached form a 4-7 membered monocyclic or 6-10 membered bicyclic heterocycle,
wherein the C$_{1-6}$-alkyl, the C$_{1-6}$-alkyl portion of the —OC$_{1-6}$-alkyl, the C$_{3-8}$-cycloalkyl of the —C(O)—

$C_{3-8}$-cycloalkyl, and the monocyclic and bicyclic heterocycle are optionally substituted with 1-3 substituents of $R^6$;

$R^4$ is H;

$R^5$ is $C_{1-6}$-alkyl, $C_{3-8}$-cycloalkyl or a ring selected from phenyl, pyridyl, pyrimidyl, thienyl, furanyl, pyrrolidinyl, pyrazolyl, imidazolyl, triazolyl, tetrazolyl, thiazolyl, oxazolyl, isothiazolyl, isoxazolyl, diazolyl, thiodiazolyl, oxadiazolyl, oxazolinyl, isoxazolinyl, thiazolinyl, pyranyl, pyrazinyl, pyridazinyl, morpholinyl, piperidinyl and piperazinyl, wherein the $C_{1-6}$-alkyl, $C_{3-8}$-cycloalkyl and ring are optionally substituted, independently, with 1-5 substituents of $R^6$;

each $R^6$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

m is 0, 1, 2, 3, 4 or 5; and n is 0, 1 or 2.

2. The compound of claim 1, or a stereoisomer or pharmaceutically acceptable salt thereof, wherein each of $B^1$, $B^2$ and $B^3$, independently, is CH; and L is —$CH_2CHR^3$— wherein $R^3$ is H, methyl, ethyl, propyl, cyclopropyl, cyclobutyl, cyclopentyl, cyclohexyl, —OH, —$OCH_3$, F, Cl, Br, —$OCF_3$, CN, —$NH_2$ or —$NHC_{1-3}$alkyl.

3. The compound of claim 2, or a stereoisomer or pharmaceutically acceptable salt thereof, wherein each $R^1$, independently, is F, Cl, $CF_3$, $OCF_3$, methyl, ethyl, CN, OH, —$OCH_3$, —$OCF_3$, —$NH_2$, $NHCH_3$ or —$C(O)CH_3$; and m is 1 or 2.

4. The compound of claim 1 of formula I-A

I-A or a stereoisomer or pharmaceutically acceptable salt thereof, wherein $A^1$ is $CR^1$ or N;
$A^2$ is $CR^1$ or N;
$A^3$ is $CR^1$ or N;
$A^4$ is $CR^1$ or N;
$A^5$ is $CR^1$ or N, provided no more than two of $A^1$, $A^2$, $A^3$, $A^4$ and $A^5$ is N;

each $R^1$, independently, is H, F, Cl, Br, $CF_3$, $OCF_3$, $C_{1-6}$-alkyl, CN, OH, —$OC_{1-6}$-alkyl, $C_{1-6}$-alkenyl, $C_{1-6}$-alkynyl, —$S(O)_n C_{1-6}$-alkyl, —$NH_2$, CN, —$NHC_{1-6}$-alkyl, —$C(O)C_{1-6}$-alkyl, —C(O)-aryl, —C(O)-heteroaryl, —C(O)-heterocyclyl, —C(O)—$C_{3-8}$-cycloalkyl or —$C(O)NR^a R^b$ wherein $R^a$ is H or $C_{1-6}$alkyl and $R^b$ is $R^6$, wherein the $C_{1-6}$-alkyl, the $C_{1-6}$-alkyl portion of the —$OC_{1-6}$-alkyl, and the $C_{3-8}$-cycloalkyl of the —C(O)—$C_{3-8}$-cycloalkyl are optionally substituted with 1-3 substituents of $R^6$;

$R^c$ is H, —$CH_3$ or F;

$R^2$ is H or F;

$R^3$ is H, $C_{1-6}$alkyl, $C_{3-6}$cycloalkyl, —OH, —$OC_{1-4}$alkyl, halo, haloalkyl, CN, —$NH_2$ or —$NHC_{1-6}$alkyl;

$R^4$ is H;

$R^5$ is $C_{1-6}$-alkyl, $C_{3-8}$-cycloalkyl or a ring selected from phenyl, pyridyl, pyrimidyl, thienyl, furanyl, pyrrolidinyl, pyrazolyl, imidazolyl, triazolyl, tetrazolyl, thiazolyl, oxazolyl, isothiazolyl, isoxazolyl, diazolyl, thiodiazolyl, oxadiazolyl, oxazolinyl, isoxazolinyl, thiazolinyl, pyranyl, pyrazinyl, pyridazinyl, morpholinyl, piperidinyl and piperazinyl, wherein the $C_{1-6}$-alkyl, $C_{3-8}$-cycloalkyl and ring are optionally substituted, independently, with 1-5 substituents of $R^6$; and each $R^6$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted, independently, with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl.

5. The compound of claim 4, or a stereoisomer or pharmaceutically acceptable salt thereof, wherein one of $A^1$ and $A^2$ is N and the other of $A^1$ and $A^2$ is $CR^1$;
$A^3$ is $CR^1$;
$A^4$ is $CR^1$; and
$A^5$ is $CR^1$.

6. The compound of claim 5, or a stereoisomer or pharmaceutically acceptable salt thereof, wherein $R^4$ is H; and $R^5$ is $C_{1-4}$alkyl substituted with 1-3 substituents of F, Cl, Br, I, $CF_3$, $C_2F_5$, $C_{1-6}$-alkyl, CN, OH, $C_{1-10}$-alkoxyl or $C_{3-10}$cycloalkyl, or fully unsaturated 3-8 membered monocyclic or a 6-12 membered bicyclic ring system, said ring system formed of carbon atoms optionally including 1-3 heteroatoms if monocyclic or 1-6 heteroatoms if bicyclic, said heteroatoms selected from O, N, or S, wherein the cycloalkyl or the ring system is optionally substituted, independently, with 1-5 substituents of F, Cl, Br, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-4}$-alkylamino-, $C_{1-4}$-dialkylamino- or $C_{1-4}$-thioalkoxyl.

7. The compound of claim 1, or a stereoisomer or pharmaceutically acceptable salt thereof, selected from 3-(2-amino-6-o-tolylquinolin-3-yl)-N-cyclohexylpropanamide;
3-(2-amino-6-o-tolylquinolin-3-yl)-N-(3,3-dimethylbutyl)propanamide;
3-(2-amino-6-o-tolylquinolin-3-yl)-N-(cyclohexylmethyl)-2-methylpropanamide;
3-(2-amino-6-o-tolylquinolin-3-yl)-N-benzylpropanamide;
3-(2-amino-6-o-tolylquinolin-3-yl)-N-(2-cyclohexylethyl)propanamide;
3-(2-amino-6-(3-methylpyridin-2-yl)quinolin-3-yl)-N-(3,3-dimethylbutyl)-2-methylpropanamide;
3-(2-amino-6-o-tolylquinolin-3-yl)-2-methyl-N-(1-methylpiperidin-3-yl)propanamide;
(R)-3-(2-amino-6-o-tolylquinolin-3-yl)-2-methyl-N-(pyrazin-2-ylmethyl)propanamide;
(R)-3-(2-amino-6-o-tolylquinolin-3-yl)-2-methyl-N-(pyridazin-3-ylmethyl)propanamide;
(R)-3-(2-amino-6-o-tolylquinolin-3-yl)-2-methyl-N-(pyrimidin-4-ylmethyl)propanamide;
(R)-3-(2-amino-6-o-tolylquinolin-3-yl)-2-methyl-N-(pyrimidin-2-ylmethyl)propanamide;
3-(2-amino-6-(3-methylpyridin-2-yl)quinolin-3-yl)-2-methyl-N—(((R)-tetrahydro-2H-pyran-3-yl)methyl)propanamide;
(R)-3-(2-amino-6-o-tolylquinolin-3-yl)-2-methyl-N-((tetrahydro-2H-pyran-4-yl)methyl)propanamide;
3-(2-amino-6-(3-methylpyridin-2-yl)quinolin-3-yl)-2-methyl-N-((tetrahydro-2H-pyran-4-yl)methyl)propanamide;
3-(2-amino-6-(3-methylpyridin-2-yl)quinolin-3-yl)-2-methyl-N—(((S)-tetrahydro-2H-pyran-3-yl)methyl)propanamide;
3-(2-amino-6-o-tolylquinolin-3-yl)-N-(3,3-dimethylbutyl)-2-methylpropanamide;
3-(2-amino-6-o-tolylquinolin-3-yl)-2-methyl-N-((tetrahydro-2H-pyran-3-yl)methyl)propanamide;
3-(2-amino-6-o-tolylquinolin-3-yl)-2-methyl-N-(thiazol-5-ylmethyl)propanamide;
3-(2-amino-7-fluoro-6-(3-methyl-2-pyridinyl)-3-quinolinyl)-N-(3,3-dimethylbutyl)-2-methylpropanamide;
N-(3-fluoro-3-methylbutyl)-2-methyl-3-(6-(3-methylpyridin-2-yl)quinolin-3-yl)propanamide;
3-(2-amino-6-(3-methylpyridin-2-yl)quinolin-3-yl)-2-methyl-N-(2-(1-methylcyclopropyl)ethyl)propanamide;
3-(2-amino-6-(2-butoxyphenyl)quinolin-3-yl)-N-(cyclohexylmethyl)-2-methylpropanamide;
3-(2-amino-6-(2-((dimethylamino)methyl)phenyl)quinolin-3-yl)-N-(cyclohexylmethyl)-2-methylpropanamide;
3-(2-amino-6-(3-methylpyridin-2-yl)quinolin-3-yl)-N-isopentyl-2-methylpropanamide;
3-(2-amino-6-(3-methylpyridin-2-yl)quinolin-3-yl)-2-methyl-N-(3,3,3-trifluoropropyl)propanamide;
3-(2-amino-6-(3-methylpyridin-2-yl)quinolin-3-yl)-N-((4,4-difluorocyclohexyl)methyl)-2-methylpropanamide;
3-(2-amino-6-(pyridin-2-yl)quinolin-3-yl)-N-(3,3-dimethylbutyl)-2-methylpropanamide;
3-(2-amino-6-(3-(2-morpholinoethyl)pyridin-2-yl)quinolin-3-yl)-N-(3,3-dimethylbutyl)-2-methylpropanamide;
3-(2-amino-6-(3-(2-(4-methylpiperazin-1-yl)ethyl)pyridin-2-yl)quinolin-3-yl)-N-(3,3-dimethylbutyl)-2-methylpropanamide;
3-(2-amino-6-(3-(2-(pyrrolidin-1-yl)ethyl)pyridin-2-yl)quinolin-3-yl)-N-(3,3-dimethylbutyl)-2-methylpropanamide;
(R)-3-(2-amino-6-(3-methylpyridin-2-yl)quinolin-3-yl)-N-(3,3-dimethylbutyl)-2-methylpropanamide;
3-(2-amino-6-(3-(2-(dimethylamino)ethyl)pyridin-2-yl)quinolin-3-yl)-N-(3,3-dimethylbutyl)-2-methylpropanamide;
(R)-3-(2-amino-6-(3-chloropyridin-2-yl)quinolin-3-yl)-N-(3,3-dimethylbutyl)-2-methylpropanamide;
3-(2-amino-6-(2-methylphenyl)-3-quinolinyl)-N-(3-hydroxy-3-methylbutyl)propanamide;
3-(2-amino-6-(2-cyanophenyl)-3-quinolinyl)-N-(2,2-dimethyltetrahydro-2H-pyran-4-yl)-2-methylpropanamide;
3-(6-(2-acetylphenyl)-2-amino-3-quinolinyl)-N-(2,2-dimethyltetrahydro-2H-pyran-4-yl)-2-methylpropanamide;
(2R)-3-(2-amino-6-o-tolylquinolin-3-yl)-N-(cis-2,6-dimethyltetrahydro-2H-pyran-4-yl)-2-methylpropanamide;
3-(2-amino-6-(2-methyl-6-(1-pyrrolidinylcarbonyl)phenyl)-3-quinolinyl)-N-(2,2-dimethyltetrahydro-2H-pyran-4-yl)-2-methylpropanamide;
3-(2-amino-6-(2-((2-methoxyphenyl)carbonyl)phenyl)-3-quinolinyl)-N-(2,2-dimethyltetrahydro-2H-pyran-4-yl)-2-methylpropanamide;
3-(2-amino-6-(2-(cyclohexylcarbonyl)phenyl)-3-quinolinyl)-N-(2,2-dimethyltetrahydro-2H-pyran-4-yl)-2-methylpropanamide;
3-(2-amino-6-(2-methyl-6-(pyrrolidine-1-carbonyl)phenyl)quinolin-3-yl)-N,2-dimethylpropanamide;
3-(2-amino-6-(2-methyl-6-(pyrrolidine-1-carbonyl)phenyl)quinolin-3-yl)-2-methyl-N-(pyridin-2-ylmethyl)propanamide;
3-(2-amino-6-(2-methyl-6-(pyrrolidine-1-carbonyl)phenyl)quinolin-3-yl)-N-cyclopropyl-2-methylpropanamide;
3-(2-amino-6-(2-methyl-6-(pyrrolidine-1-carbonyl)phenyl)quinolin-3-yl)-N-benzyl-2-methylpropanamide;
3-(6-(2-acetylphenyl)-2-aminoquinolin-3-yl)-2-methyl-N-phenylpropanamide;
3-(2-amino-6-(2-methyl-6-(pyrrolidine-1-carbonyl)phenyl)quinolin-3-yl)-2-methyl-N-phenylpropanamide;
(2R)-3-(2-amino-6-o-tolylquinolin-3-yl)-2-methyl-N-(2-methyltetrahydro-2H-pyran-4-yl)propanamide;
3-(2-amino-6-(2,3-dichlorophenyl)quinolin-3-yl)-N-(2,2-dimethyltetrahydro-2H-pyran-4-yl)-2-methylpropanamide;
(R)-3-(2-amino-6-o-tolylquinolin-3-yl)-N-(cis-2-ethynyltetrahydro-2H-pyran-4-yl)-2-methylpropanamide;
(2R)-3-(2-amino-6-(2-methylphenyl)-3-quinolinyl)-N-(3,3-dimethylcyclohexyl)-2-methylpropanamide;
3-(2-amino-6-(2-methylphenyl)-3-quinolinyl)-N-(3,3-dimethylcyclohexyl)propanamide;
3-(2-amino-6-(2-methylphenyl)-3-quinolinyl)-N-(-2,2-dimethyltetrahydro-2H-pyran-4-yl)propanamide;
(2R)-3-(2-amino-6-o-tolylquinolin-3-yl)-N-(2,2-dimethyltetrahydro-2H-pyran-4-yl)-2-methylpropanamide;
3-(2-amino-6-(4-chlorophenyl)-3-quinolinyl)-N-(2,2-dimethyltetrahydro-2H-pyran-4-yl)-2-methylpropanamide; and 3-(2-amino-6-(3-chlorophenyl)-3-quinolinyl)-N-(2,2-dimethyltetrahydro-2H-pyran-4-yl)-2-methylpropanamide.

8. A pharmaceutical composition comprising a compound according to claim 1 and a pharmaceutically acceptable excipient.

9. A process for preparing a compound according to claim 1, the process comprising the step of (a) reacting a compound 17

17

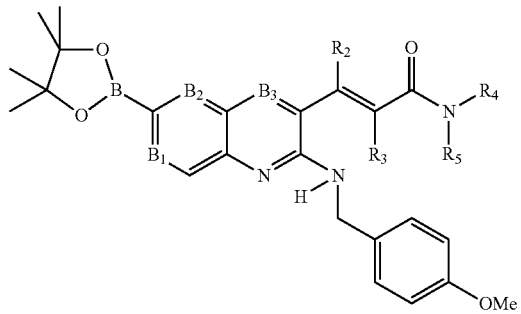

wherein $B^1$, $B^2$, $B^3$, $R^2$, $R^3$, $R^4$ and $R^5$ of Formula I are as defined herein, with a compound having the structure

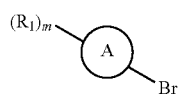

wherein ring A, $R^1$ and m are as defined herein to make a compound 18 of the formula

18

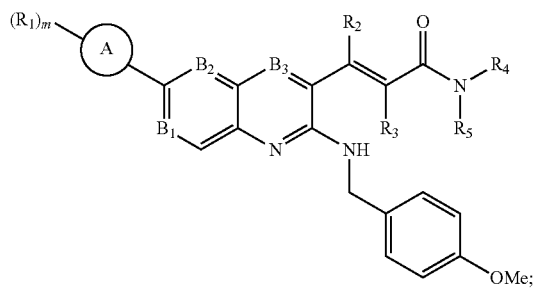

(b) reducing compound 18 to make a compound 19 of formula

19

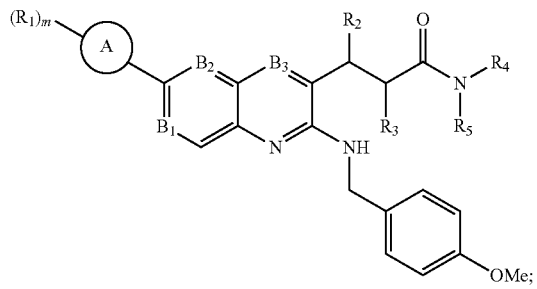

and (c) removing the

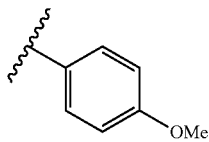 [SMILES: *c1ccc(OC)cc1]

protecting group from compound 19, to make a compound of claim 1.

10. The compound of claim 1, or a stereoisomer or pharmaceutically acceptable salt thereof, selected from
3-(2-amino-6-(2-chlorophenyl)quinolin-3-yl)-N-(cyclohexylmethyl)propanamide;
3-(2-amino-6-o-tolylquinolin-3-yl)-N-(cyclohexylmethyl)butanamide;
(R)-3-(2-amino-6-(2-methyl-6-(pyrrolidine-1-carbonyl)phenyl)quinolin-3-yl)-N,2-dimethylpropanamide;
3-(2-amino-6-o-tolylquinolin-3-yl)-N-(cyclohexylmethyl)propanamide;
3-(2-amino-6-o-tolylquinolin-3-yl)-N-(tetrahydro-2H-pyran-4-yl)propanamide;
3-(2-amino-6-o-tolylquinolin-3-yl)-N-(tetrahydro-2H-pyran-4-yl)propanamide;
3-(2-amino-6-o-tolylquinolin-3-yl)-N-((tetrahydrofuran-2-yl)methyl)propanamide;
3-(2-amino-6-o-tolylquinolin-3-yl)-N-(2-methoxyethyl)propanamide;
3-(2-amino-6-o-tolylquinolin-3-yl)-N-((tetrahydro-2H-pyran-4-yl)methyl)propanamide;
3-(2-amino-6-o-tolylquinolin-3-yl)-N-neopentylpropanamide;
3-(2-amino-6-o-tolylquinolin-3-yl)-N-phenylpropanamide;
2-((2-amino-6-o-tolylquinolin-3-yl)methyl)-N-(cyclohexylmethyl)pentanamide;
3-(2-amino-6-(3-methylpyridin-2-yl)quinolin-3-yl)-N-(cyclohexylmethyl)propanamide;
3-(2-amino-6-(pyridin-3-yl)quinolin-3-yl)-N-(cyclohexylmethyl)propanamide;
3-(2-amino-6-(2-methylpyridin-3-yl)quinolin-3-yl)-N-(cyclohexylmethyl)propanamide;
3-(2-amino-6-o-tolylquinolin-3-yl)-N-(1-methylpiperidin-3-yl)propanamide;
3-(2-amino-6-o-tolylquinolin-3-yl)-N-((tetrahydro-2H-pyran-2-yl)methyl)propanamide;
3-(2-amino-6-(2-cyanophenyl)quinolin-3-yl)-N-(cyclohexylmethyl)propanamide;
3-(2-amino-6-(2-fluorophenyl)quinolin-3-yl)-N-(cyclohexylmethyl)propanamide;
3-(2-amino-6-(3-fluorophenyl)quinolin-3-yl)-N-(cyclohexylmethyl)propanamide;
3-(2-amino-6-(2-methoxyphenyl)quinolin-3-yl)-N-(cyclohexylmethyl)propanamide;
3-(2-amino-6-phenylquinolin-3-yl)-N-(cyclohexylmethyl)propanamide;
3-(2-amino-6-(4-methylpyridin-3-yl)quinolin-3-yl)-N-(cyclohexylmethyl)propanamide;
3-(2-amino-6-o-tolylquinolin-3-yl)-N—((R)-1-cyclohexylethyl)-2-methylpropanamide;
3-(2-amino-6-(2-ethylphenyl)quinolin-3-yl)-N-(cyclohexylmethyl)propanamide;
2-((2-amino-6-o-tolylquinolin-3-yl)methyl)-N-(2-fluorophenyl)butanamide;

3-(2-amino-6-o-tolylquinolin-3-yl)-2-methyl-N-phenylpropanamide;
3-(2-amino-6-o-tolylquinolin-3-yl)-N-benzyl-2-methylpropanamide;
3-(2-amino-6-o-tolylquinolin-3-yl)-N-(2-fluoro-4-methylphenyl)propanamide;
3-(2-amino-6-o-tolylquinolin-3-yl)-N-((1-methyl-1H-pyrazol-3-yl)methyl)propanamide;
3-(2-amino-6-o-tolylquinolin-3-yl)-N-((3-methyloxetan-3-yl)methyl)propanamide;
3-(2-amino-6-o-tolylquinolin-3-yl)-N-((1-ethyl-1H-pyrazol-3-yl)methyl)propanamide;
2-((2-amino-6-o-tolylquinolin-3-yl)methyl)-N-(cyclohexylmethyl)butanamide;
3-(2-amino-6-o-tolylquinolin-3-yl)-N-(thiazol-2-ylmethyl)propanamide;
3-(2-amino-6-(4-fluorophenyl)quinolin-3-yl)-N-(cyclohexylmethyl)propanamide;
2-((2-amino-6-o-tolylquinolin-3-yl)methyl)-N-(cyclohexylmethyl)-3-methylbutanamide;
3-(2-amino-6-o-tolylquinolin-3-yl)-N-(oxazol-2-ylmethyl)propanamide;
N-(2-fluoro-4-methylbenzyl)-3-(2-amino-6-o-tolylquinolin-3-yl)propanamide;
3-(2-amino-6-o-tolylquinolin-3-yl)-N-(cyclohexylmethyl)-2-methoxypropanamide;
3-(2-amino-6-(2-isopropylphenyl)quinolin-3-yl)-N-(cyclohexylmethyl)propanamide;
(R)-3-(2-amino-6-o-tolylquinolin-3-yl)-N—((R)-1-(2-methoxyphenyl)ethyl)-2-methylpropanamide;
(S)-3-(2-amino-6-o-tolylquinolin-3-yl)-N—((R)-1-(2-methoxyphenyl)ethyl)-2-methylpropanamide;
3-(2-amino-6-o-tolylquinolin-3-yl)-N—((R)-1-(2-methoxyphenyl)ethyl)-2-methylpropanamide;
3-(2-amino-6-o-tolylquinolin-3-yl)-N—((R)-1-(2-(difluoromethoxy)phenyl)ethyl)-2-methylpropanamide;
3-(2-amino-6-o-tolylquinolin-3-yl)-N—((R)-1-(pyridin-3-yl)ethyl)propanamide;
3-(2-amino-6-(3-methylpyridin-2-yl)quinolin-3-yl)-N—((R)-1-(pyridin-3-yl)ethyl)propanamide;
3-(2-amino-6-(3-chloropyridin-2-yl)quinolin-3-yl)-2-methyl-N—(((S)-tetrahydro-2H-pyran-2-yl)methyl)propanamide;
3-(2-amino-6-(3-chloropyridin-2-yl)quinolin-3-yl)-2-methyl-N—(((R)-tetrahydro-2H-pyran-2-yl)methyl)propanamide;
3-(2-amino-6-o-tolylquinolin-3-yl)-2-methyl-N-((tetrahydrofuran-3-yl)methyl)propanamide;
3-(2-amino-6-o-tolylquinolin-3-yl)-2-methyl-N-((1-methyl-1H-pyrazol-4-yl)methyl)propanamide;
3-(2-amino-7-methyl-6-(2-methylphenyl)-3-quinolinyl)-N-(cyclohexylmethyl)propanamide;
3-(2-amino-7-fluoro-6-(2-methylphenyl)-3-quinolinyl)-N-(cyclohexylmethyl)propanamide;
3-(2-amino-7-fluoro-6-(3-methyl-2-pyridinyl)-3-quinolinyl)-2-methyl-N-(tetrahydro-2H-pyran-4-ylmethyl)propanamide;
3-(6-(3-chloropyridin-2-yl)quinolin-3-yl)-N-((4,4-difluorocyclohexyl)methyl)-2-methylpropanamide;
N-(4-fluoro-4-methylpentan-2-yl)-2-methyl-3-(6-(3-methylpyridin-2-yl)quinolin-3-yl)propanamide;
3-(2-amino-6-o-tolylquinolin-3-yl)-N-(1-(2-methoxyphenyl)ethyl)-2-methylpropanamide;
3-(2-amino-6-o-tolylquinolin-3-yl)-N-(1-(2-methoxyphenyl)ethyl)propanamide;
3-(2-amino-6-o-tolylquinolin-3-yl)-N-(1-(2-fluorophenyl)ethyl)-2-methylpropanamide;
3-(2-amino-6-(2-fluoro-6-methylpyridin-3-yl)quinolin-3-yl)-N-(cyclohexylmethyl)-2-methylpropanamide;
3-(2-amino-6-(3-methylpyridin-2-yl)quinolin-3-yl)-2-methyl-N-(2,2,2-trifluoroethyl)propanamide;
3-(2-amino-6-(3-methylpyridin-2-yl)quinolin-3-yl)-N-(2-cyclopropylethyl)-2-methylpropanamide;
3-(2-amino-6-(3-methylpyridin-2-yl)quinolin-3-yl)-2-methyl-N-(2-(tetrahydrofuran-2-yl)ethyl)propanamide;
3-(2-amino-6-(3-methylpyridin-2-yl)quinolin-3-yl)-2-methyl-N—((R)-1,1,1-trifluoropropan-2-yl)propanamide;
3-(2-amino-6-o-tolylquinolin-3-yl)-N-(2-cyclopropylethyl)propanamide;
3-(2-amino-6-(3-chloropyridin-2-yl)quinolin-3-yl)-2-methyl-N-(3,3,3-trifluoropropyl)propanamide;
3-(2-amino-6-o-tolylquinolin-3-yl)-N—((R)-1-(2-methoxyphenyl)ethyl)-2-methylpropanamide;
3-(2-amino-6-o-tolylquinolin-3-yl)-N—((R)-1-(2-(difluoromethoxy)phenyl)ethyl)-2-methylpropanamide;
(R)-3-(2-amino-6-o-tolylquinolin-3-yl)-N-(1-(pyridin-3-yl)ethyl)propanamide;
(R)-3-(2-amino-6-(3-methylpyridin-2-yl)quinolin-3-yl)-N-(1-(pyridin-3-yl)ethyl)propanamide;
(R)-3-(2-amino-6-(3-methylpyridin-2-yl)quinolin-3-yl)-N-(1-(2-(difluoromethoxy)phenyl)ethyl)propanamide;
3-(2-amino-6-o-tolylquinolin-3-yl)-N-(pyridazin-4-ylmethyl)propanamide;
3-(2-amino-6-(2-methylphenyl)-3-quinolinyl)-N-(2-hydroxy-2-methylpropyl)propanamide;
3-(2-Amino-6-(2-methyl-6-(pyrrolidine-1-carbonyl)phenyl)quinolin-3-yl)-N,2-dimethylpropanamide;
3-(6-(2-acetylphenyl)-2-aminoquinolin-3-yl)-N,2-dimethylpropanamide;
(S) 3-(2-amino-6-(2-methyl-6-(pyrrolidine-1-carbonyl)phenyl)quinolin-3-yl)-N,2-dimethylpropanamide;
3-(6-(2-acetylphenyl)-2-aminoquinolin-3-yl)-N-(3,3-dimethylbutyl)-2-methylpropanamide;
3-(2-amino-6-(2-(cyclohexanecarbonyl)phenyl)quinolin-3-yl)-N,2-dimethylpropanamide;
3-(2-amino-6-(2-(1-pyrrolidinylcarbonyl)phenyl)-3-quinolinyl)-N-(3,3-dimethylbutyl)propanamide;
3-(2-amino-6-(2-chloro-4-fluorophenyl)-3-quinolinyl)-N-(2,2-dimethyltetrahydro-2H-pyran-4-yl)-2-methylpropanamide; and
3-(2-amino-6-(4-fluorophenyl)-3-quinolinyl)-N-(2,2-dimethyltetrahydro-2H-pyran-4-yl)-2-methylpropanamide.

11. A compound or a stereoisomer or a pharmaceutically acceptable salt thereof selected from
3-(2-amino-6-o-tolylquinolin-3-yl)-N-(cyclohexylmethyl)-N-methylpropanamide;
3-(2-amino-6-(thiazol-4-yl)quinolin-3-yl)-N-(cyclohexylmethyl)propanamide;
3-(2-amino-6-(2-methyl-1H-imidazol-1-yl)quinolin-3-yl)-N-(cyclohexylmethyl)propanamide;
3-(2-amino-6-(2-methylcyclopropyl)quinolin-3-yl)-N-(3,3-dimethylbutyl)-2-methylpropanamide;
3-(2-amino-6-(3-chlorophenyl)-3-quinolinyl)-2-methyl-N-(5-oxaspiro[3,5]non-8-yl)propanamide;
2-((2-amino-6-o-tolylquinolin-3-yl)methyl)-N-(cyclohexylmethyl)-N-methylpentanamide;
N-(3-(2-amino-6-o-tolylquinolin-3-yl)propyl)cyclohexanecarboxamide;
3-(2-amino-6-(3-methylpyridin-2-yl)quinolin-3-yl)-1-(2-ethylazetidin-1-yl)-2-methylpropan-1-one;
3-(2-amino-6-(2-(methoxymethyl)cyclopropyl)quinolin-3-yl)-N-(3,3-dimethylbutyl)-2-methylpropanamide;

3-(2-amino-6-(2-ethylcyclopropyl)quinolin-3-yl)-N-(3,3-dimethylbutyl)-2-methylpropanamide;

3-(2-amino-6-((1S,2R)-2-methylcyclopropyl)quinolin-3-yl)-N-(3,3-dimethylbutyl)-2-methylpropanamide;

3-(2-amino-6-o-tolylquinolin-3-yl)-1-(3,3-difluoropyrrolidin-1-yl)propan-1-one;

3-(2-amino-6-(2,3-dichlorophenyl)quinolin-3-yl)-2-methyl-N-(5-oxaspiro[3.5]nonan-8-yl)propanamide;

(2R)-3-(2-amino-6-(2-methylphenyl)-3-quinolinyl)-2-methyl-N-(5-oxaspiro[3.5]non-8-yl)propanamide; and 3-(2-amino-6-(2-chlorophenyl)-3-quinolinyl)-2-methyl-N-(5-oxaspiro[3.5]non-8-yl)propanamide.

12. A pharmaceutical composition comprising a compound according to claim 7 and a pharmaceutically acceptable excipient.

13. A pharmaceutical composition comprising a compound according to claim 10 and a pharmaceutically acceptable excipient.

14. A pharmaceutical composition comprising a compound according to claim 11 and a pharmaceutically acceptable excipient.

* * * * *